(12) United States Patent
Bauer et al.

(10) Patent No.: US 9,079,877 B2
(45) Date of Patent: Jul. 14, 2015

(54) PROCESS FOR PREPARING CHIRAL COMPOUNDS

(71) Applicant: Pfizer Inc., Groton, CT (US)

(72) Inventors: David W Bauer, Portage, MI (US);
Padraig M O'Neill, Ringaskiddy (IE);
Timothy J Watson, Waterford, CT (US);
Shanghui Hu, Cranbury, NJ (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/135,753

(22) Filed: Dec. 20, 2013

(65) Prior Publication Data

US 2014/0187794 A1    Jul. 3, 2014

Related U.S. Application Data

(62) Division of application No. 12/671,752, filed as application No. PCT/IB2008/002016 on Jul. 23, 2008, now Pat. No. 8,642,783.

(60) Provisional application No. 60/953,725, filed on Aug. 3, 2007.

(51) Int. Cl.
| | |
|---|---|
| *C07D 405/06* | (2006.01) |
| *C07D 209/48* | (2006.01) |
| *C07D 319/08* | (2006.01) |
| *C12P 7/62* | (2006.01) |
| *C12P 13/00* | (2006.01) |
| *C12P 13/02* | (2006.01) |
| *C12P 17/10* | (2006.01) |

(52) U.S. Cl.
CPC ............ *C07D 405/06* (2013.01); *C07D 209/48* (2013.01); *C07D 319/08* (2013.01); *C12P 7/62* (2013.01); *C12P 13/001* (2013.01); *C12P 13/02* (2013.01); *C12P 17/10* (2013.01)

(58) Field of Classification Search
None
See application file for complete search history.

(56) References Cited

U.S. PATENT DOCUMENTS

| | | |
|---|---|---|
| 5,155,251 A | 10/1992 | Butler et al. |
| 5,795,749 A | 8/1998 | Wong et al. |
| 2005/0287650 A1 | 12/2005 | Kierkels et al. |
| 2009/0062553 A1 | 3/2009 | Moody et al. |
| 2009/0209001 A1 | 8/2009 | Shuermann et al. |

FOREIGN PATENT DOCUMENTS

| | | |
|---|---|---|
| WO | 2004027075 | 4/2004 |
| WO | 2006134482 | 12/2006 |
| WO | WO 2008075165 A1 * | 6/2008 |

OTHER PUBLICATIONS

Baumann, K. L., et al., The Convergent Synthesis of Cl-981, an Optically Active, Highly Potent, Tissue Selective Inhibitor of HMG-CoA Reductase, Tetrahedron Letters, vol. 33, No. 17, pp. 2283-2284, 1982.
Bertolini, G., et al., Synthesis and Reactivity of Mevinolin-Like Lactone Precursors, Synthetic Communications, vol. 24, No. 13, pp. 1833-1845, 1994.
Calveras, J., et al., Influence of N-amino protecting group an aldolase-catalyzed aldol additions of dihydroxyacetone phosphate to amino aldehyde, Tetrahedron, vol. 62, pp. 2648-2656, (2006).
Database UniProt (Online), Dec. 1, 2001, Phosphodeoxyriboaldolase; Deoxyriboaldolase; DERA.
Database UniProt (Online), Jun. 1, 2003, Dexyribose-phosphate Aldolase.
Database UniProt (Online), Oct. 1, 2000, Dexyribose-phosphate Aldolase; EC=4.1.2.4; Phosphodeoxyriboaldolase; Deoxyriboaldolase; DERA.
Database UniProt (Online), Dec. 15, 2003, Deoxyribose-phosphate Aldolase.
Database UniProt (Online), Dec. 20, 2005, Deoxyribose-phoshate Aldolase. EC=4.1.2.4.
Database UniProt (Online), Apr. 3, 2007, Putative Deoxyribose-phosphate Aldolase.
Database UniProt (Online), Apr. 4, 2006, Phosphodeoxyriboaldolase; Deoxyriboaldolase; DERA.
Database UniProt (Online), Feb. 6, 2007, Deoxyribose-phosphate Aldolase.
Gijsen, H.J.M, et al. Sequential Three- and Four-Substrate Aldol Reactions Catalyzed by Aldolases, Journal of American Chemical Society, vol. 117, No. 29, pp. 7585-7591, 1995.
Gijsen, H.J.M., et al. Unprecedented Asymmetric Aldol Reactions with Three Aldehyde Substrates Catalyzed by 2-Deoxyribose-5-phosphate Aldolase, vol. 116, pp. 8422-8423.
Greenberg, W.A., et al. Development of an efficient, scalable, aldolase-catalyzed process for enantioselective synthesis of statin intermediates, PNAS, vol. 101, No. 16, pp. 5788-5793, 2004.
Jennewein, S., et al., Directed evolution of an inductrial biocatalyst: 2-deoxy-D-ribose-5-phosphate aldolase Biotechnol. J., vol. 1, pp. 537-548, 2006.
Liu, J., et al., Sequential aldol condensation catalyzed by DERA mutant SER238Asp and a formal total synthesis of atorvastatin, Tetrahedron Letters, vol. 45, pp. 2439-2441, 2004.
Sakuraba, H. et al. The First Crystal Structure of Archaeal Aldolase, Journal of Biological Chemistry, vol. 278, No. 12, pp. 10799-10806, 2003.

* cited by examiner

*Primary Examiner* — Michael Barker
(74) *Attorney, Agent, or Firm* — Francis J. Tinney

(57) ABSTRACT

The present invention is directed to a 2-deoxyribose-5-phosphate aldolase (DERA) chemoenzymatic process for making chiral compounds.

13 Claims, 6 Drawing Sheets

SEQUENCE LISTING

<160> NUMBER OF SEQ ID NOS: 30

<210> SEQ ID NO 1
<211> LENGTH: 780
<212> TYPE: DNA
<213> ORGANISM: Escherichia coli

<400> SEQUENCE: 1

```
atgactgatc tgaaagcaag cagcctgcgt gcactgaaat tgatggacct gaccaccctg      60
aatgacgacg acaccgacga gaaagtgatc gccctgtgtc atcaggccaa aactccggtc     120
ggcaataccg ccgctatctg tatctatcct cgctttatcc cgattgctcg caaaactctg     180
aaagagcagg gcaccccgga aatccgtatc gctacggtaa ccaacttccc acacggtaac     240
gacgacatcg acatcgcgct ggcagaaacc cgtgcggcaa tcgcctacgg tgctgatgaa     300
gttgacgttg tgttcccgta ccgcgcgctg atggcgggta acgagcaggt tggttttgac     360
```

```
ctggtgaaag cctgtaaaga ggcttgcgcg gcagcgaatg tactgctgaa agtgatcatc    420
gaaaccggcg aactgaaaga cgaagcgctg atccgtaaag cgtctgaaat ctccatcaaa    480
gcgggtgcgg acttcatcaa aacctctacc ggtaaagtgg ctgtgaacgc gacgccggaa    540
agcgcgcgca tcatgatgga agtgatccgt gatatgggcg tagaaaaaac cgttggtttc    600
aaaccggcgg gcggcgtgcg tactgcggaa gatgcgcaga atatctcgc cattgcagat     660 gaactgttcg gtgctgactg gcagatgcg cgtcactacc gctttggcgc ttccagcctg     720
ctggcaagcc tgctgaaagc gctgggtcac ggcgacggta agagcgccag cagctactaa    780
```

<210> SEQ ID NO 2
<211> LENGTH: 669
<212> TYPE: DNA
<213> ORGANISM: Artificial Sequence
<220> FEATURE:
<223> OTHER INFORMATION: random DNA isolated from an environmental
      sample

<400> SEQUENCE: 2

```
atgggtaata tcgcgaaaat gattgatcac accctcttaa aacccgaagc aaccgaacaa     60
caaattgtac aattatgcac ggaagcgaaa caatatggct ttgcagcagt atgcgtaaat    120
ccgacatggg ttaaaaccgc cgcacgtgaa ttaagcggga cagacgttcg tgtgtgtact    180
gtaattggat ttcccttggg cgctacgact ccagaaacta agcattcga aactactaac     240 gcgattgaaa atggagcacg ggaagtagat atggtaatta atattggtgc attgaaatct    300
ggacaagatg aactggtgga acgtgatatt cgtgccgttg ttgaagctgc agcaggccgc    360
gcgcttgtga agtaattgt agaaacagcc cttcttactg atgaagaaaa agttcgcgct     420
tgtcaattag cagtaaaagc gggtgccgat tatgtgaaga cgtcgacagg atttagcggt    480
ggtggtgcaa cggtggaaga tgtggcttta atgcggaaaa cggttggtga tcgtgcaggg    540
gtcaaagcaa gcgcggagt acgtgactgg aaaacagcag aagcaatgat taacgcagga    600
gcaacgcgca ttggcacaag ttctggagta gcaatcgtaa caggtggaac cggccgggca    660
gactattaa                                                            669
```

<210> SEQ ID NO 3
<211> LENGTH: 663
<212> TYPE: DNA
<213> ORGANISM: Deinococcus radiodurans

<400> SEQUENCE: 3

```
atgggactcg cctcctacat cgaccacacg ctgcttaagg ccaccgccac gctcgccgac     60
atccgcacgc tgtgtgagga agcccgcgag cactcgttct acgcggtgtg catcaacccg    120
gtctttattc cccacgcccg cgcctggctc gaaggcagca acgtgaaggt cgccaccgtc    180
tgcggctttc ccctcggcgc catcagctcc gagcagaaag ctctggaagc ccgcctgagc    240
gccgaaacgg gcgccgacga atcgatatg gtcatccaca tcggctcggc gcttgccggc    300
gactgggacg cggtggaagc cgacgtgcgg gcagtgcgcc gcgcggtgcc cgagcaggtg    360
ctcaaggtga ttatcgaaac ctgctacctg accgacgagc aaaagcgctt ggcgactgag    420
gtcgccgtac agggcggcgc cgacttcgtg aagacgagca caggcttcgg caccggcggc    480
gccaccgtgg acgacgtgcg cctgatggcg gaagtgatcg ggggccgcgc cggactcaag    540
gcggcgggcg cgtccgcac tcctgccgac gcgcaagcca tgatcgaggc gggcgcgacc    600
cggctgggca cctcgggcgg cgtgggtctg gtgtcgggcg gcgaaaacgg agccggctac    660
```

| tga | 663 |

<210> SEQ ID NO 4
<211> LENGTH: 672
<212> TYPE: DNA
<213> ORGANISM: Listeria monocytogenes

<400> SEQUENCE: 4

| atgggaattg ctaaaatgat cgatcacact gctttaaaac cagacacaac gaaagaacaa | 60 |
| attttaacac taacaaaaga agcaagagaa tacggttttg cttccgtatg cgtaaatcca | 120 |
| acttgggtaa aactatccgc tgaacaactt gctggagcag aatctgtagt atgtactgtt | 180 |
| atcggtttcc cactaggagc gaatacccct gaagtaaaag catttgaagt aaaagatgct | 240 |
| atccaaaacg gtgcaaaaga agtggatatg gttattaata tcggcgcact aaaagacaaa | 300 |
| gacgacgaac tagtagaacg tgatattcgc gctgtagtcg atgctgccaa aggaaaagca | 360 |
| ttagtaaaag taattatcga aacttgccta ttaacagacg aagaaaaagt tcgcgcatgt | 420 |
| gaaatcgctg taaaagcggg aacagacttc gttaaaacat ccactggatt ctccacaggt | 480 |
| ggcgcaactc ccgaagatat cgccttaatg cgtaaaactg taggaccaaa catcggcgta | 540 |
| aaagcatctg gtggggttcg tacgaaagaa gacgtagaaa aaatgatcga agcaggcgca | 600 |
| actcgtattg gcgcaagtgc aggtgtcgca attgtttccg gcgaaaaacc agccaaacca | 660 |
| gataattact aa | 672 |

<210> SEQ ID NO 5
<211> LENGTH: 672
<212> TYPE: DNA
<213> ORGANISM: Haemophilus influenzae

<400> SEQUENCE: 5

| atgacatcaa atcaacttgc tcaatatatc gatcacaccg cacttaccgc agaaaaaaat | 60 |
| gaacaagata tttcgacact ctgtaatgaa gcgattgaac acggatttta ttctgtatgt | 120 |
| atcaattctg cttatattcc actcgctaaa gaaaaacttg ctggctcaaa tgtaaaaatt | 180 |
| tgcaccgtag ttggattccc tttggggggcg aatttaaccct cagtcaaagc atttgaaacg | 240 |
| caagaatcta ttaaagcggg tgcaaatgaa attgatatgg tgattaatgt aggttggata | 300 |
| aaaatcgcaaa aatgggatga agtaaaacaa gatattcaag cggtatttaa tgcttgtaat | 360 |
| ggcacgccat taaaagtgat tttagaaact tgtttgctca ctaaagatga aatagtgaaa | 420 |
| gcctgcgaaa tttgtaaaga aatcggtgta gcttttgtta aaacatcaac aggctttaat | 480 |
| aaaggtggtg cgaccgtaga agatgttgca ttgatgaaaa acacggtcgg caatattggt | 540 |
| gttaaagcat caggtggtgt gcgtgatact gaaactgcac ttgcaatgat taaggcgggt | 600 |
| gcgactcgca ttggtgcaag cgctggcatt gcgattatta gcggtactca agacactcaa | 660 |
| agcacttact aa | 672 |

<210> SEQ ID NO 6
<211> LENGTH: 747
<212> TYPE: DNA
<213> ORGANISM: Thermotoga maritima

<400> SEQUENCE: 6

| atgatagagt acaggattga ggaggcagta gcgaagtaca gagagttcta cgaattcaag | 60 |
| cccgtcagag aaagcgcagg tattgaagat gtgaaaagtg ctatagagca cacgaatctg | 120 |

| | |
|---|---|
| aaaccgtttg ccacaccaga cgatataaaa aaactctgtc ttgaagcaag ggaaaatcgt | 180 |
| ttccatggag tctgtgtgaa tccgtgttat gtgaaactgg ctcgtgaaga actcgaagga | 240 |
| accgatgtga aagtcgtcac cgttgttggt tttccactgg gagcgaacga aactcggacg | 300 |
| aaagcccatg aggcgatttt cgctgttgag agtggagccg atgagatcga tatggtcatc | 360 |
| aacgttggca tgctcaaggc aaaggagtgg gagtacgttt acgaggatat aagaagtgtt | 420 |
| gtcgaatcgg tgaaaggaaa agttgtgaag gtgatcatcg aaacgtgcta tctggatacg | 480 |
| gaagagaaga tagcggcgtg tgtcatttcc aaacttgctg gagctcattt cgtgaagact | 540 |
| tccacgggat ttggaacagg aggggcgacc gcagaagacg ttcatctcat gaaatggatc | 600 |
| gtgggagatg agatgggtgt aaaagcttcc ggagggatca gaaccttcga ggacgctgtt | 660 |
| aaaatgatca tgtacggtgc tgatagaata ggaacgagtt cgggagttaa gatcgttcag | 720 |
| gggggagaag agagatatgg aggttga | 747 |

<210> SEQ ID NO 7
<211> LENGTH: 708
<212> TYPE: DNA
<213> ORGANISM: Aeropyrum pernix

<400> SEQUENCE: 7

| | |
|---|---|
| atgccgtcgg ccagggatat actgcagcag gtctagaca ggctagggag ccctgaggac | 60 |
| ctcgcctcga ggatagactc tacgctacta agccctaggg ctacggagga ggacgttagg | 120 |
| aatcttgtga gagaggcgtc ggactacggg tttagatgcg cggttctgac tccagtgtac | 180 |
| acagtaaaga tttctgggct ggctgagaag cttggtgtga agctatgtag cgttataggc | 240 |
| tttccctgg gccaggcccc gctcgaggta agctagttg aggcacaaac tgttttagag | 300 |
| gctgggcta ctgagcttga tgttgtcccc catctctcac taggccccga agctgtttac | 360 |
| agggaggtct cagggatagt gaagttggcg aaaagctatg gagccgttgt gaaagtaata | 420 |
| ttagaagcgc cactctggga tgacaaaacg ctctccctcc tggtggactc gtcgaggagg | 480 |
| gcggggcgg atatagtgaa gacaagcacc ggggtctata caagggtgg tgatccagta | 540 |
| acggtcttca ggctggccag tcttgccaag cccttggta tgggtgtaaa ggcaagcggc | 600 |
| ggtataagga gtggcatcga cgccgtcctc ccgtaggag ctggcgcgga tatcataggg | 660 |
| acaagcagtg ctgtaaaggt tttggagagc ttcaaatccc tagtctaa | 708 |

<210> SEQ ID NO 8
<211> LENGTH: 870
<212> TYPE: DNA
<213> ORGANISM: Porphyromonas gingivalis

<400> SEQUENCE: 8

| | |
|---|---|
| atggctgcaa acaaatatga atggccttc gcacagttcg atccagctga aagcgaagaa | 60 |
| cgcatcctgc tgaaaactga ccagatcatt cgtgaccact attcccgttt cgacactcca | 120 |
| gaaactaaaa agttcctgca tggcgttatc gatctgacgt ctctgaacgc caccgactct | 180 |
| gaggaatcta tcactaaatt caccgaatct gtaaacgatt tcgaagatac cgacccgact | 240 |
| atccctagcg ttgcggcgat ctgcgtttat ccgaactttg tcagcaccgt gcgtgaaacc | 300 |
| ctgactgccg agaatgtgaa agttgcaagc gtcagcggtt gcttcccggc ctcccagagc | 360 |
| ttcatcgaag tgaaactggc agaaaccgca ctggcggtta cgacggtgc ggatgaaatt | 420 |
| gacattgttc tgaacatggg taattcctg tccggtgatt acgaggccgc agccactgag | 480 |
| atcgaggaac agatcgctgc ggcgaagggt gcgaccgtaa aagttatcct ggagactggt | 540 |

```
gctctgaaga cgccggaaaa cattcgccgc gcaaccatcc tgtctctgtt ttgtggcgcc    600
catttcgtta aaacctctac tggcaaaggc tacccgggcg cctctctgga agcagcttac    660
actatgtgta aagtcctgaa acagtactac ggcctgttcg gtgaagttcg tggcatcaag    720
ctgagcggcg gtatccgtac caccgaagac gcggttaagt actactgcct gatcgaaacg    780
ctgctgggca agaatggct  gaccccggcg tacttccgca tcggcgcctc ctctctggtt    840
gatgctctgc gccaggatat tatggtttaa                                     870
```

```
<210> SEQ ID NO 9
<211> LENGTH: 669
<212> TYPE: DNA
<213> ORGANISM: Enterococcus faecalis

<400> SEQUENCE: 9
atggaactga accgcatgat tgaccacact attctgaaac cggaagccac cgaggcggct    60
gtgcagaaaa ttatcgatga agctaaagaa tacaacttct tcagcgtctg tatcaacccg   120
tgttgggttg cttttgcctc cgagcagctg gctgatactg atgttgccgt ctgtaccgta   180
atcggtttcc cgctgggcgc gaacacgccg gaggttaaag cgtacgaagc agctgacgcc   240
attaaaaacg gtgctaatga ggtggatatg gtgatcaata ttggtgctct gaaatcccaa   300
cagtacgact acgtgcgcca agacatccag ggtgtggttg acgccgcaaa aggtaaagca   360
ctggttaaag ttatcatcga aactgccctg ctgaccgatg aagagaaagt taaggcttgc   420
gaactggcga agaagcagg  cgctgatttc gtgaaaacca gcaccggttt ttccactggc   480
ggtgcaaaag ttgctgacat tcgtctgatg cgcgaaaccg tgggtccgga tatgggcgtt   540
aaagcatccg gtggcgtaca caacgcagaa gaagcactgg ccatgatcga agcgggcgca   600
actcgtatcg gcgcttccac cggtgtagcc atcgtaagcg gtgctactgg tgagggtacc   660
aaatggtaa                                                           669
```

```
<210> SEQ ID NO 10
<211> LENGTH: 1014
<212> TYPE: DNA
<213> ORGANISM: unknown
<220> FEATURE:
<223> OTHER INFORMATION: marine actinobacterium

<400> SEQUENCE: 10
atgactattg aatccgctat cgcgctggca cctgcagaac gtgctgttaa cctgattggt    60
agcgacctga ccgaaaaatc tctgaaactg cacctgtctg gtgtcgacgcg              120 gttggtctgg aacagcgtgc tgccggtctg tccacccgct ctatcaaaac cacctccaaa   180
gcttgggccc tggacaccat catcaaactg atcgatctga ctactctgga gggcgcagat   240
actccgggca aggttcgttc tctggctgcg aaagcaatgc tgccggacgc ctctgatgtg   300
tccgctccgc aggtggcagc tgtgtgcgtt acggtgata tggtgccata cgcggcggaa    360
gcactgggct cctcttggtc taatggttct gacaacggca ttaacgttgc tgcggtggca   420
actgcgttcc catccggtcg cagctccctg ccaatcaaaa tcgctgacac caaggaagcc   480
gttgcccacg tgctgacga  aatcgacatg gtaatcgatc gtggtgcgtt cctgagcggc   540
aaatacggtg ttgtgttcga ccagatcgta gctgtgaaag aagcttgccg ccgcgaaaac   600
ggcacttacg cgcacctgaa agttatcctg gaaaccggcg aactgaacac ctatgacaac   660
gtccgccgtg cctcctggct ggcgatcctg gcgggtggtg actttgtgaa aacctctacc   720
```

-continued

| | |
|---|---|
| ggcaaggtta gcccggccgc aaccctgccg gttacgctgc tgatgctgga agtcgttcgc | 780 |
| gattggcatg tgctgactgg cgagaaaatc ggtgtgaaac cagccggtgg tatccgctcc | 840 |
| tccaaagacg cgattaaata cctggtcacc gtggcggaaa ccgtaggtga agagtggctg | 900 |
| caaccgcacc tgtttcgctt tggcgcctcc tccctgctga cgacgttct gatgcagcgt | 960 |
| cagaagctgt ctaccggcca ctactccggc ccagattacg tgaccatcga ctaa | 1014 |

<210> SEQ ID NO 11
<211> LENGTH: 975
<212> TYPE: DNA
<213> ORGANISM: Nocardioides species

<400> SEQUENCE: 11

| | |
|---|---|
| atgtcttcta ctccaactat tctggatccg gcgtttgagg acgttacccg ttctgaagca | 60 |
| tctctgcgcc gtttcctgca cggcctgccg ggtgtcgatc aggtgggcgc agaggcccgt | 120 |
| gccgctggtc tggcaacccg ttccattaaa acgtccgcaa agaatttgc actggacctg | 180 |
| gcgattcgta tggttgacct gaccacgctg gagggccagg atacgccggg taaggttcgt | 240 |
| gccctgagcg cgaaagcaat gcgtccggat ccgtctgatc caacctgtcc tgctactgct | 300 |
| gctgtatgtg tttaccccgga catggttggc atcgcgaaac aggcgctggg tactagcggc | 360 |
| gtacacgtag ctgctgtggc tactgctttc ccgtctggcc gtgccgctct ggacatcaaa | 420 |
| ctggcggacg ttcgtgatgc ggtggacgca ggcgctgacg aaatcgatat ggttatcgac | 480 |
| cgcggtgctt ttctggctgg tcgttaccaa cacgtatacg acgaaattgt tgcggtgcgc | 540 |
| gaagcctgcc gccgtgaaaa cggtgaaggc gctcacctga aggtaatctt cgagactggt | 600 |
| gagctgcaga cctacgacaa cgttcgccgt gcgagctggc tggcgatgat ggctggtgca | 660 |
| cacttcgtta aaacgtccac cggcaaagtc cagccggcag ctaccctgcc ggttaccctg | 720 |
| gttatgctgc aggccgtacg tgactttcgt ggcgcaacgg gccgtatggt tggcgttaaa | 780 |
| cctgctggcg gtatccgtac cgccaaggac gcaatcaaat acctggttat ggtaaacgag | 840 |
| gtagcgggcg aagattggct ggacccggac tggtttcgtt ttggtgcatc tactctgctg | 900 |
| aacgacctgc tgatgcagcg tacgaagatg aaaaccggcc gttacagcgg cccagactac | 960 |
| tttaccctgg actaa | 975 |

<210> SEQ ID NO 12
<211> LENGTH: 828
<212> TYPE: DNA
<213> ORGANISM: Geobacillus kaustophilus

<400> SEQUENCE: 12

| | |
|---|---|
| atggaactga tcactcagcc gtcttgttgg gtatttttccg tcttttttccg ccgtcagtac | 60 |
| ggctggctgg ttttttgtgga aggtgcttgg tacgatggtc gccgtcaaac tttccacctg | 120 |
| gatggtaacg gccgcaaagg cttcctgcgc atgactatga atatcgcaaa aatgatcgat | 180 |
| cacaccctgc tgaaaccgga agcgactgag cagcagatcg tacaactgtg caccgaagct | 240 |
| aaacagtatg gttttgcttc cgtttgtgtg aaccctacgt gggtgaaaac cgccgcacgc | 300 |
| gaactgtctg gtaccgacgt tcgtgtttgt accgtaattg gcttcccgct gggcgcgact | 360 |
| accccagaaa ccaaagcgtt cgaaactacc aacgcgatcg aaaacggcgc tcgtgaagtc | 420 |
| gacatggtaa tcaacattgg cgctctgaaa tctggtcagg acgaactggt agagcgtgac | 480 |
| atccgcgccg tcgtagaagc tgcggcaggc cgtgcactgg taaaagtaat cgttgaaacc | 540 |
| gctctgctga ctgatgaaga gaaagttcgt gcgtgtcagc tggcggttaa agctggtgca | 600 |

```
gattacgtga aaacgagcac tggtttctcc ggtggtggcg ctactgtcga agacgtggcg    660
ctgatgcgta aaaccgtagg cgatcgcgca ggcgttaaag cgagcggcgg tgttcgtgat    720
tggaagactg ccgaagctat gattaacgca ggcgcgactc gtatcggcac ttctagcggc    780
gtggcaattg ttactggcgg caccggtcgc gctgacacta atggtaa                  828
```

<210> SEQ ID NO 13
<211> LENGTH: 678
<212> TYPE: DNA
<213> ORGANISM: Listeria innocua

<400> SEQUENCE: 13

```
atgactatcg ctaaaatgat tgatcacacg gcgctgaagc cagataccac caaagaacaa    60
atcctgacgc tgaccaaaga agcacgtgaa tatggctttg ctagcgtctg tgtgaatccg    120
acttgggtga aactgtctgc ggaacagctg agcggcgctg aatctgtggt gtgcaccgtc    180
atcggttttc gctgggcgc gaatactccg gaagtgaagg cattcgaagt aaaaaacgct    240
atcgaaaacg gcgcgaagga gtagatatg gttatcaaca ttggtgctct gaaggataag    300
gacgacgaac tggtggaacg tgatatccgt gccgtcgtgg atgctgctaa aggtaaagcg    360
ctggtgaaag tcattatcga aacctgcctg ctgaccgatg aagagaaggt ccgtgcttgc    420
gaaatcgccg tgaaagctgg cactgatttc gttaaaactt ctactggctt ttctactggt    480
ggcgcgactg cagaagacat cgcactgatg cgtaagactg tcggtccgaa catcggtgta    540
aaagcgtccg gtggtgttcg tactaaagaa gacgttgaga agatgatcga agcgggtgcc    600
acccgtatcg gcgcttctgc aggtgtggca atcgtatccg gtgaaaaacc ggcgaaacct    660
gacaacacca agtggtaa                                                  678
```

<210> SEQ ID NO 14
<211> LENGTH: 723
<212> TYPE: DNA
<213> ORGANISM: Bacillus halodurans

<400> SEQUENCE: 14

```
atgtctcgct ctattgcaca aatgatcgat cacaccctgc tgaaacctaa taccaccgaa    60
gaccagatcg tgaaactgtg cgaagaggct aaagaatact cttttcgcct cgtatgcgtc    120
aacccaacgt gggtcgcgct ggcagcgcag ctgctgaaag acgctcctga tgtgaaagtg    180
tgcactgtta tcggcttccc actgggtgca accacgcctg aagtaaaagc gtttgaaacc    240
actaacgcaa tcgagaacgg cgcaacggag gttgatatgg ttatcaacat cggtgccctg    300
aaggacaaac agtacgaact ggttggtcgt gatatccagg ctgttgtgaa ggcagcagaa    360
ggcaaagccc tgaccaaagt gattatcgaa acctccctgc tgaccgaaga agaaaagaag    420
gcggcttgtg aactggcggt aaaagcaggt gctgatttcg tcaaaacgtc taccggtttc    480
tctggtggcg gtgcaaccgc agaagacatt gccctgatgc gtaaggttgt tggtcctaac    540
ctgggcgtta aggccagcgg cggtgtgcgt gacctgtctg acgcgaaggc gatgattgac    600
gcgggcgcga ctcgtatcgg cgcttccgca ggtgttgcga tcgttaatgg tgaacgctct    660
gaaggttcca cgaaatggac cgcagctggt gcggcgacga cgtgcgcttg tacgggcggc    720
taa                                                                  723
```

<210> SEQ ID NO 15
<211> LENGTH: 669
<212> TYPE: DNA

<213> ORGANISM: Streptococcus suis

<400> SEQUENCE: 15

```
atgaaactga acaaatacat cgatcacacc atcctgaaac cggaaacgac tcaggaacag      60
gtggagaaaa tcctggctga agcgaaagaa tacgatttcg cgtccgtctg cgttaacccg     120
acgtgggtag ctctggcagc tgaaagcctg aaagatagcg acgtcaaagt ctgcactgtc     180
atcggcttcc cgctgggcgc taacactccg gcagtgaagg cgttcgaaac taaagacgct     240
attagcaacg gcgcggatga aatcgacatg gtgattaaca tcggcgcact gaaaacgggt     300
aactacgatc tggttctgga agatattaag gctgtcgttg cagcaagcgg cgataaactg     360
gtaaaggtaa tcatcgaagc gtgcctgctg accgacgatg aaaaggttaa agcgtgccag     420
ctgtctcagg aagcgggcgc tgactacgtc aagacgagca ctggcttctc taccggcggt     480
gcgacggtcg cagatgttgc tctgatgcgt aaaactgttg gcccggacat gggcgtaaaa     540
gcgtctggcg gtgcgcgctc ttacgaagac gctatcgcgt tcattgaagc tggcgcaagc     600
cgtattggcg ccagctctgg cgtggcgatc atgaatggtg cgcaggctga tggcgacacc     660
aagtggtaa                                                             669
```

<210> SEQ ID NO 16
<211> LENGTH: 259
<212> TYPE: PRT
<213> ORGANISM: Escherichia coli

<400> SEQUENCE: 16

```
Met Thr Asp Leu Lys Ala Ser Ser Leu Arg Ala Leu Lys Leu Met Asp
1               5                   10                  15

Leu Thr Thr Leu Asn Asp Asp Thr Asp Glu Lys Val Ile Ala Leu
            20                  25                  30

Cys His Gln Ala Lys Thr Pro Val Gly Asn Thr Ala Ala Ile Cys Ile
            35                  40                  45

Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Glu Gln Val Gly Phe Asp Leu Val Lys Ala Cys Lys Glu Ala
            115                 120                 125

Cys Ala Ala Ala Asn Val Leu Leu Lys Val Ile Ile Glu Thr Gly Glu
    130                 135                 140

Leu Lys Asp Glu Ala Leu Ile Arg Lys Ala Ser Glu Ile Ser Ile Lys
145                 150                 155                 160

Ala Gly Ala Asp Phe Ile Lys Thr Ser Thr Gly Lys Val Ala Val Asn
                165                 170                 175

Ala Thr Pro Glu Ser Ala Arg Ile Met Met Glu Val Ile Arg Asp Met
            180                 185                 190

Gly Val Glu Lys Thr Val Gly Phe Lys Pro Ala Gly Gly Val Arg Thr
            195                 200                 205

Ala Glu Asp Ala Gln Lys Tyr Leu Ala Ile Ala Asp Glu Leu Phe Gly
    210                 215                 220

Ala Asp Trp Ala Asp Ala Arg His Tyr Arg Phe Gly Ala Ser Ser Leu
```

```
225                 230                 235                 240
Leu Ala Ser Leu Leu Lys Ala Leu Gly His Gly Asp Gly Lys Ser Ala
                245                 250                 255

Ser Ser Tyr

<210> SEQ ID NO 17
<211> LENGTH: 222
<212> TYPE: PRT
<213> ORGANISM: Artificial Sequence
<220> FEATURE:
<223> OTHER INFORMATION: random DNA isolated from an environmental
      sample

<400> SEQUENCE: 17

Met Gly Asn Ile Ala Lys Met Ile Asp His Thr Leu Leu Lys Pro Glu
1               5                   10                  15

Ala Thr Glu Gln Gln Ile Val Gln Leu Cys Thr Glu Ala Lys Gln Tyr
                20                  25                  30

Gly Phe Ala Ala Val Cys Val Asn Pro Thr Trp Val Lys Thr Ala Ala
            35                  40                  45

Arg Glu Leu Ser Gly Thr Asp Val Arg Val Cys Thr Val Ile Gly Phe
50                  55                  60

Pro Leu Gly Ala Thr Thr Pro Glu Thr Lys Ala Phe Glu Thr Thr Asn
65                  70                  75                  80

Ala Ile Glu Asn Gly Ala Arg Glu Val Asp Met Val Ile Asn Ile Gly
                85                  90                  95

Ala Leu Lys Ser Gly Gln Asp Glu Leu Val Glu Arg Asp Ile Arg Ala
            100                 105                 110

Val Val Glu Ala Ala Gly Arg Ala Leu Val Lys Val Ile Val Glu
            115                 120                 125

Thr Ala Leu Leu Thr Asp Glu Glu Lys Val Arg Ala Cys Gln Leu Ala
130                 135                 140

Val Lys Ala Gly Ala Asp Tyr Val Lys Thr Ser Thr Gly Phe Ser Gly
145                 150                 155                 160

Gly Gly Ala Thr Val Glu Asp Val Ala Leu Met Arg Lys Thr Val Gly
                165                 170                 175

Asp Arg Ala Gly Val Lys Ala Ser Gly Gly Val Arg Asp Trp Lys Thr
            180                 185                 190

Ala Glu Ala Met Ile Asn Ala Gly Ala Thr Arg Ile Gly Thr Ser Ser
        195                 200                 205

Gly Val Ala Ile Val Thr Gly Gly Thr Gly Arg Ala Asp Tyr
    210                 215                 220

<210> SEQ ID NO 18
<211> LENGTH: 220
<212> TYPE: PRT
<213> ORGANISM: Deinococcus radiodurans

<400> SEQUENCE: 18

Met Gly Leu Ala Ser Tyr Ile Asp His Thr Leu Leu Lys Ala Thr Ala
1               5                   10                  15

Thr Leu Ala Asp Ile Arg Thr Leu Cys Glu Glu Ala Arg Glu His Ser
                20                  25                  30

Phe Tyr Ala Val Cys Ile Asn Pro Val Phe Ile Pro His Ala Arg Ala
            35                  40                  45

Trp Leu Glu Gly Ser Asp Val Lys Val Ala Thr Val Cys Gly Phe Pro
        50                  55                  60
```

```
Leu Gly Ala Ile Ser Ser Glu Gln Lys Ala Leu Glu Ala Arg Leu Ser
 65                  70                  75                  80

Ala Glu Thr Gly Ala Asp Glu Ile Asp Met Val Ile His Ile Gly Ser
                 85                  90                  95

Ala Leu Ala Gly Asp Trp Asp Ala Val Glu Ala Asp Val Arg Ala Val
            100                 105                 110

Arg Arg Ala Val Pro Glu Gln Val Leu Lys Val Ile Glu Thr Cys
        115                 120                 125

Tyr Leu Thr Asp Glu Gln Lys Arg Leu Ala Thr Glu Val Ala Val Gln
    130                 135                 140

Gly Gly Ala Asp Phe Val Lys Thr Ser Thr Gly Phe Gly Thr Gly Gly
145                 150                 155                 160

Ala Thr Val Asp Asp Val Arg Leu Met Ala Glu Val Ile Gly Gly Arg
                165                 170                 175

Ala Gly Leu Lys Ala Ala Gly Val Arg Thr Pro Ala Asp Ala Gln
            180                 185                 190

Ala Met Ile Glu Ala Gly Ala Thr Arg Leu Gly Thr Ser Gly Gly Val
        195                 200                 205

Gly Leu Val Ser Gly Gly Glu Asn Gly Ala Gly Tyr
    210                 215                 220
```

<210> SEQ ID NO 19
<211> LENGTH: 223
<212> TYPE: PRT
<213> ORGANISM: Listeria monocytogenes

<400> SEQUENCE: 19

```
Met Gly Ile Ala Lys Met Ile Asp His Thr Ala Leu Lys Pro Asp Thr
  1               5                  10                  15

Thr Lys Glu Gln Ile Leu Thr Leu Thr Lys Glu Ala Arg Glu Tyr Gly
             20                  25                  30

Phe Ala Ser Val Cys Val Asn Pro Thr Trp Val Lys Leu Ser Ala Glu
         35                  40                  45

Gln Leu Ala Gly Ala Glu Ser Val Val Cys Thr Val Ile Gly Phe Pro
     50                  55                  60

Leu Gly Ala Asn Thr Pro Glu Val Lys Ala Phe Glu Val Lys Asp Ala
 65                  70                  75                  80

Ile Gln Asn Gly Ala Lys Glu Val Asp Met Val Ile Asn Ile Gly Ala
                 85                  90                  95

Leu Lys Asp Lys Asp Asp Glu Leu Val Glu Arg Asp Ile Arg Ala Val
            100                 105                 110

Val Asp Ala Ala Lys Gly Lys Ala Leu Val Lys Val Ile Ile Glu Thr
        115                 120                 125

Cys Leu Leu Thr Asp Glu Glu Lys Val Arg Ala Cys Glu Ile Ala Val
    130                 135                 140

Lys Ala Gly Thr Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Ile Gly Val Lys Ala Ser Gly Gly Val Arg Thr Lys Glu Asp Val
            180                 185                 190

Glu Lys Met Ile Glu Ala Gly Ala Thr Arg Ile Gly Ala Ser Ala Gly
        195                 200                 205

Val Ala Ile Val Ser Gly Glu Lys Pro Ala Lys Pro Asp Asn Tyr
```

<210> SEQ ID NO 20
<211> LENGTH: 223
<212> TYPE: PRT
<213> ORGANISM: Haemophilus influenzae

<400> SEQUENCE: 20

Met Thr Ser Asn Gln Leu Ala Gln Tyr Ile Asp His Thr Ala Leu Thr
1               5                   10                  15

Ala Glu Lys Asn Glu Gln Asp Ile Ser Thr Leu Cys Asn Glu Ala Ile
            20                  25                  30

Glu His Gly Phe Tyr Ser Val Cys Ile Asn Ser Ala Tyr Ile Pro Leu
        35                  40                  45

Ala Lys Glu Lys Leu Ala Gly Ser Asn Val Lys Ile Cys Thr Val Val
    50                  55                  60

Gly Phe Pro Leu Gly Ala Asn Leu Thr Ser Val Lys Ala Phe Glu Thr
65                  70                  75                  80

Gln Glu Ser Ile Lys Ala Gly Ala Asn Glu Ile Asp Met Val Ile Asn
                85                  90                  95

Val Gly Trp Ile Lys Ser Gln Lys Trp Asp Glu Val Lys Gln Asp Ile
            100                 105                 110

Gln Ala Val Phe Asn Ala Cys Asn Gly Thr Pro Leu Lys Val Ile Leu
        115                 120                 125

Glu Thr Cys Leu Leu Thr Lys Asp Glu Ile Val Lys Ala Cys Glu Ile
    130                 135                 140

Cys Lys Glu Ile Gly Val Ala Phe Val Lys Thr Ser Thr Gly Phe Asn
145                 150                 155                 160

Lys Gly Gly Ala Thr Val Glu Asp Val Ala Leu Met Lys Asn Thr Val
                165                 170                 175

Gly Asn Ile Gly Val Lys Ala Ser Gly Gly Val Arg Asp Thr Glu Thr
            180                 185                 190

Ala Leu Ala Met Ile Lys Ala Gly Ala Thr Arg Ile Gly Ala Ser Ala
        195                 200                 205

Gly Ile Ala Ile Ile Ser Gly Thr Gln Asp Thr Gln Ser Thr Tyr
    210                 215                 220

<210> SEQ ID NO 21
<211> LENGTH: 248
<212> TYPE: PRT
<213> ORGANISM: Thermotoga maritima

<400> SEQUENCE: 21

Met Ile Glu Tyr Arg Ile Glu Glu Ala Val Ala Lys Tyr Arg Glu Phe
1               5                   10                  15

Tyr Glu Phe Lys Pro Val Arg Glu Ser Ala Gly Ile Glu Asp Val Lys
            20                  25                  30

Ser Ala Ile Glu His Thr Asn Leu Lys Pro Phe Ala Thr Pro Asp Asp
        35                  40                  45

Ile Lys Lys Leu Cys Leu Glu Ala Arg Glu Asn Arg Phe His Gly Val
    50                  55                  60

Cys Val Asn Pro Cys Tyr Val Lys Leu Ala Arg Glu Glu Leu Glu Gly
65                  70                  75                  80

Thr Asp Val Lys Val Val Thr Val Val Gly Phe Pro Leu Gly Ala Asn
                85                  90                  95

Glu Thr Arg Thr Lys Ala His Glu Ala Ile Phe Ala Val Glu Ser Gly

```
                100                 105                 110
Ala Asp Glu Ile Asp Met Val Ile Asn Val Gly Met Leu Lys Ala Lys
            115                 120                 125

Glu Trp Glu Tyr Val Tyr Glu Asp Ile Arg Ser Val Glu Ser Val
130                 135                 140

Lys Gly Lys Val Val Lys Val Ile Glu Thr Cys Tyr Leu Asp Thr
145                 150                 155                 160

Glu Glu Lys Ile Ala Ala Cys Val Ile Ser Lys Leu Ala Gly Ala His
                165                 170                 175

Phe Val Lys Thr Ser Thr Gly Phe Gly Thr Gly Ala Thr Ala Glu
            180                 185                 190

Asp Val His Leu Met Lys Trp Ile Val Gly Asp Glu Met Gly Val Lys
                195                 200                 205

Ala Ser Gly Gly Ile Arg Thr Phe Glu Asp Ala Val Lys Met Ile Met
            210                 215                 220

Tyr Gly Ala Asp Arg Ile Gly Thr Ser Ser Gly Val Lys Ile Val Gln
225                 230                 235                 240

Gly Gly Glu Glu Arg Tyr Gly Gly
                245

<210> SEQ ID NO 22
<211> LENGTH: 235
<212> TYPE: PRT
<213> ORGANISM: Aeropyrum pernix

<400> SEQUENCE: 22

Met Pro Ser Ala Arg Asp Ile Leu Gln Gln Gly Leu Asp Arg Leu Gly
1               5                   10                  15

Ser Pro Glu Asp Leu Ala Ser Arg Ile Asp Ser Thr Leu Leu Ser Pro
            20                  25                  30

Arg Ala Thr Glu Glu Asp Val Arg Asn Leu Val Arg Glu Ala Ser Asp
        35                  40                  45

Tyr Gly Phe Arg Cys Ala Val Leu Thr Pro Val Tyr Thr Val Lys Ile
    50                  55                  60

Ser Gly Leu Ala Glu Lys Leu Gly Val Lys Leu Cys Ser Val Ile Gly
65                  70                  75                  80

Phe Pro Leu Gly Gln Ala Pro Leu Glu Val Lys Leu Val Glu Ala Gln
                85                  90                  95

Thr Val Leu Glu Ala Gly Ala Thr Glu Leu Asp Val Val Pro His Leu
            100                 105                 110

Ser Leu Gly Pro Glu Ala Val Tyr Arg Glu Val Ser Gly Ile Val Lys
        115                 120                 125

Leu Ala Lys Ser Tyr Gly Ala Val Val Lys Val Ile Leu Glu Ala Pro
    130                 135                 140

Leu Trp Asp Asp Lys Thr Leu Ser Leu Leu Val Asp Ser Ser Arg Arg
145                 150                 155                 160

Ala Gly Ala Asp Ile Val Lys Thr Ser Thr Gly Val Tyr Thr Lys Gly
                165                 170                 175

Gly Asp Pro Val Thr Val Phe Arg Leu Ala Ser Leu Ala Lys Pro Leu
            180                 185                 190

Gly Met Gly Val Lys Ala Ser Gly Gly Ile Arg Ser Gly Ile Asp Ala
        195                 200                 205

Val Leu Ala Val Gly Ala Gly Ala Asp Ile Ile Gly Thr Ser Ser Ala
    210                 215                 220
```

```
Val Lys Val Leu Glu Ser Phe Lys Ser Leu Val
225             230             235
```

<210> SEQ ID NO 23
<211> LENGTH: 289
<212> TYPE: PRT
<213> ORGANISM: Porphyromonas gingivalis

<400> SEQUENCE: 23

```
Met Ala Ala Asn Lys Tyr Glu Met Ala Phe Ala Gln Phe Asp Pro Ala
1               5                   10                  15

Glu Ser Glu Glu Arg Ile Leu Leu Lys Thr Asp Gln Ile Ile Arg Asp
                20                  25                  30

His Tyr Ser Arg Phe Asp Thr Pro Glu Thr Lys Lys Phe Leu His Gly
            35                  40                  45

Val Ile Asp Leu Thr Ser Leu Asn Ala Thr Asp Ser Glu Glu Ser Ile
        50                  55                  60

Thr Lys Phe Thr Glu Ser Val Asn Asp Phe Glu Asp Thr Asp Pro Thr
65                  70                  75                  80

Ile Pro Ser Val Ala Ala Ile Cys Val Tyr Pro Asn Phe Val Ser Thr
                85                  90                  95

Val Arg Glu Thr Leu Thr Ala Glu Asn Val Lys Val Ala Ser Val Ser
                100                 105                 110

Gly Cys Phe Pro Ala Ser Gln Ser Phe Ile Glu Val Lys Leu Ala Glu
            115                 120                 125

Thr Ala Leu Ala Val Ser Asp Gly Ala Asp Glu Ile Asp Ile Val Leu
        130                 135                 140

Asn Met Gly Lys Phe Leu Ser Gly Asp Tyr Glu Ala Ala Thr Glu
145                 150                 155                 160

Ile Glu Glu Gln Ile Ala Ala Lys Gly Ala Thr Val Lys Val Ile
                165                 170                 175

Leu Glu Thr Gly Ala Leu Lys Thr Pro Glu Asn Ile Arg Arg Ala Thr
            180                 185                 190

Ile Leu Ser Leu Phe Cys Gly Ala His Phe Val Lys Thr Ser Thr Gly
        195                 200                 205

Lys Gly Tyr Pro Gly Ala Ser Leu Glu Ala Ala Tyr Thr Met Cys Lys
210                 215                 220

Val Leu Lys Gln Tyr Tyr Gly Leu Phe Gly Glu Val Arg Gly Ile Lys
225                 230                 235                 240

Leu Ser Gly Gly Ile Arg Thr Thr Glu Asp Ala Val Lys Tyr Tyr Cys
                245                 250                 255

Leu Ile Glu Thr Leu Leu Gly Lys Glu Trp Leu Thr Pro Ala Tyr Phe
            260                 265                 270

Arg Ile Gly Ala Ser Ser Leu Val Asp Ala Leu Arg Gln Asp Ile Met
        275                 280                 285

Val
```

<210> SEQ ID NO 24
<211> LENGTH: 222
<212> TYPE: PRT
<213> ORGANISM: Enterococcus faecalis

<400> SEQUENCE: 24

```
Met Glu Leu Asn Arg Met Ile Asp His Thr Ile Leu Lys Pro Glu Ala
1               5                   10                  15

Thr Glu Ala Ala Val Gln Lys Ile Ile Asp Glu Ala Lys Glu Tyr Asn
```

```
                       20                  25                  30
Phe Phe Ser Val Cys Ile Asn Pro Cys Trp Val Ala Phe Ala Ser Glu
                35                  40                  45

Gln Leu Ala Asp Thr Asp Val Ala Val Cys Thr Val Ile Gly Phe Pro
 50                  55                  60

Leu Gly Ala Asn Thr Pro Glu Val Lys Ala Tyr Glu Ala Ala Asp Ala
 65                  70                  75                  80

Ile Lys Asn Gly Ala Asn Glu Val Asp Met Val Ile Asn Ile Gly Ala
                85                  90                  95

Leu Lys Ser Gln Gln Tyr Asp Tyr Val Arg Gln Asp Ile Gln Gly Val
               100                 105                 110

Val Asp Ala Ala Lys Gly Lys Ala Leu Val Lys Val Ile Ile Glu Thr
               115                 120                 125

Ala Leu Leu Thr Asp Glu Glu Lys Val Lys Ala Cys Glu Leu Ala Lys
               130                 135                 140

Glu Ala Gly Ala Asp Phe Val Lys Thr Ser Thr Gly Phe Ser Thr Gly
145                 150                 155                 160

Gly Ala Lys Val Ala Asp Ile Arg Leu Met Arg Glu Thr Val Gly Pro
               165                 170                 175

Asp Met Gly Val Lys Ala Ser Gly Gly Val His Asn Ala Glu Glu Ala
               180                 185                 190

Leu Ala Met Ile Glu Ala Gly Ala Thr Arg Ile Gly Ala Ser Thr Gly
               195                 200                 205

Val Ala Ile Val Ser Gly Ala Thr Gly Glu Gly Thr Lys Trp
 210                 215                 220
```

<210> SEQ ID NO 25
<211> LENGTH: 337
<212> TYPE: PRT
<213> ORGANISM: unknown
<220> FEATURE:
<223> OTHER INFORMATION: marine actinobacterium

<400> SEQUENCE: 25

```
Met Thr Ile Glu Ser Ala Ile Ala Leu Ala Pro Ala Glu Arg Ala Val
 1                   5                  10                  15

Asn Leu Ile Gly Ser Asp Leu Thr Glu Lys Ser Leu Lys Leu His Leu
                20                  25                  30

Glu Gly Leu Ser Gly Val Asp Ala Val Gly Leu Glu Gln Arg Ala Ala
                35                  40                  45

Gly Leu Ser Thr Arg Ser Ile Lys Thr Thr Ser Lys Ala Trp Ala Leu
                50                  55                  60

Asp Thr Ile Ile Lys Leu Ile Asp Leu Thr Thr Leu Glu Gly Ala Asp
 65                  70                  75                  80

Thr Pro Gly Lys Val Arg Ser Leu Ala Ala Lys Ala Met Leu Pro Asp
                85                  90                  95

Ala Ser Asp Val Ser Ala Pro Gln Val Ala Ala Val Cys Val Tyr Gly
               100                 105                 110

Asp Met Val Pro Tyr Ala Ala Glu Ala Leu Gly Ser Ser Trp Ser Asn
               115                 120                 125

Gly Ser Asp Asn Gly Ile Asn Val Ala Ala Val Ala Thr Ala Phe Pro
               130                 135                 140

Ser Gly Arg Ser Ser Leu Pro Ile Lys Ile Ala Asp Thr Lys Glu Ala
145                 150                 155                 160

Val Ala His Gly Ala Asp Glu Ile Asp Met Val Ile Asp Arg Gly Ala
```

165                 170                 175
Phe Leu Ser Gly Lys Tyr Gly Val Val Phe Asp Gln Ile Val Ala Val
            180                 185                 190

Lys Glu Ala Cys Arg Arg Glu Asn Gly Thr Tyr Ala His Leu Lys Val
            195                 200                 205

Ile Leu Glu Thr Gly Glu Leu Asn Thr Tyr Asp Asn Val Arg Arg Ala
        210                 215                 220

Ser Trp Leu Ala Ile Leu Ala Gly Gly Asp Phe Val Lys Thr Ser Thr
225                 230                 235                 240

Gly Lys Val Ser Pro Ala Ala Thr Leu Pro Val Thr Leu Leu Met Leu
            245                 250                 255

Glu Val Val Arg Asp Trp His Val Leu Thr Gly Glu Lys Ile Gly Val
            260                 265                 270

Lys Pro Ala Gly Gly Ile Arg Ser Ser Lys Asp Ala Ile Lys Tyr Leu
            275                 280                 285

Val Thr Val Ala Glu Thr Val Gly Glu Glu Trp Leu Gln Pro His Leu
        290                 295                 300

Phe Arg Phe Gly Ala Ser Ser Leu Leu Asn Asp Val Leu Met Gln Arg
305                 310                 315                 320

Gln Lys Leu Ser Thr Gly His Tyr Ser Gly Pro Asp Tyr Val Thr Ile
            325                 330                 335

Asp

<210> SEQ ID NO 26
<211> LENGTH: 324
<212> TYPE: PRT
<213> ORGANISM: Nocardioides species

<400> SEQUENCE: 26

Met Ser Ser Thr Pro Thr Ile Leu Asp Pro Ala Phe Glu Asp Val Thr
1               5                   10                  15

Arg Ser Glu Ala Ser Leu Arg Arg Phe Leu His Gly Leu Pro Gly Val
            20                  25                  30

Asp Gln Val Gly Ala Glu Ala Arg Ala Ala Gly Leu Ala Thr Arg Ser
        35                  40                  45

Ile Lys Thr Ser Ala Lys Glu Phe Ala Leu Asp Leu Ala Ile Arg Met
    50                  55                  60

Val Asp Leu Thr Thr Leu Glu Gly Gln Asp Thr Pro Gly Lys Val Arg
65              70                  75                  80

Ala Leu Ser Ala Lys Ala Met Arg Pro Asp Pro Ser Asp Pro Thr Cys
            85                  90                  95

Pro Ala Thr Ala Ala Val Cys Val Tyr Pro Asp Met Val Gly Ile Ala
            100                 105                 110

Lys Gln Ala Leu Gly Thr Ser Gly Val His Val Ala Ala Val Ala Thr
        115                 120                 125

Ala Phe Pro Ser Gly Arg Ala Leu Asp Ile Lys Leu Ala Asp Val
    130                 135                 140

Arg Asp Ala Val Asp Ala Gly Ala Asp Glu Ile Asp Met Val Ile Asp
145                 150                 155                 160

Arg Gly Ala Phe Leu Ala Gly Arg Tyr Gln His Val Tyr Asp Glu Ile
            165                 170                 175

Val Ala Val Arg Glu Ala Cys Arg Arg Glu Asn Gly Glu Gly Ala His
            180                 185                 190

Leu Lys Val Ile Phe Glu Thr Gly Glu Leu Gln Thr Tyr Asp Asn Val

```
            195                 200                 205
Arg Arg Ala Ser Trp Leu Ala Met Met Ala Gly Ala His Phe Val Lys
210                 215                 220

Thr Ser Thr Gly Lys Val Gln Pro Ala Ala Thr Leu Pro Val Thr Leu
225                 230                 235                 240

Val Met Leu Gln Ala Val Arg Asp Phe Arg Gly Ala Thr Gly Arg Met
                245                 250                 255

Val Gly Val Lys Pro Ala Gly Gly Ile Arg Thr Ala Lys Asp Ala Ile
                260                 265                 270

Lys Tyr Leu Val Met Val Asn Glu Val Ala Gly Glu Asp Trp Leu Asp
                275                 280                 285

Pro Asp Trp Phe Arg Phe Gly Ala Ser Thr Leu Leu Asn Asp Leu Leu
                290                 295                 300

Met Gln Arg Thr Lys Met Lys Thr Gly Arg Tyr Ser Gly Pro Asp Tyr
305                 310                 315                 320

Phe Thr Leu Asp

<210> SEQ ID NO 27
<211> LENGTH: 275
<212> TYPE: PRT
<213> ORGANISM: Geobacillus kaustophilus

<400> SEQUENCE: 27

Met Glu Leu Ile Thr Gln Pro Ser Cys Trp Val Phe Ser Val Phe Phe
1               5                   10                  15

Arg Arg Gln Tyr Gly Trp Leu Val Phe Val Glu Gly Ala Trp Tyr Asp
                20                  25                  30

Gly Arg Arg Gln Thr Phe His Leu Asp Gly Asn Gly Arg Lys Gly Phe
            35                  40                  45

Leu Arg Met Thr Met Asn Ile Ala Lys Met Ile Asp His Thr Leu Leu
50                  55                  60

Lys Pro Glu Ala Thr Glu Gln Gln Ile Val Gln Leu Cys Thr Glu Ala
65                  70                  75                  80

Lys Gln Tyr Gly Phe Ala Ser Val Cys Val Asn Pro Thr Trp Val Lys
                85                  90                  95

Thr Ala Ala Arg Glu Leu Ser Gly Thr Asp Val Arg Val Cys Thr Val
                100                 105                 110

Ile Gly Phe Pro Leu Gly Ala Thr Thr Pro Glu Thr Lys Ala Phe Glu
            115                 120                 125

Thr Thr Asn Ala Ile Glu Asn Gly Ala Arg Glu Val Asp Met Val Ile
130                 135                 140

Asn Ile Gly Ala Leu Lys Ser Gly Gln Asp Glu Leu Val Glu Arg Asp
145                 150                 155                 160

Ile Arg Ala Val Val Glu Ala Ala Gly Arg Ala Leu Val Lys Val
                165                 170                 175

Ile Val Glu Thr Ala Leu Leu Thr Asp Glu Lys Val Arg Ala Cys
                180                 185                 190

Gln Leu Ala Val Lys Ala Gly Ala Asp Tyr Val Lys Thr Ser Thr Gly
            195                 200                 205

Phe Ser Gly Gly Gly Ala Thr Val Glu Asp Val Ala Leu Met Arg Lys
            210                 215                 220

Thr Val Gly Asp Arg Ala Gly Val Lys Ala Ser Gly Gly Val Arg Asp
225                 230                 235                 240

Trp Lys Thr Ala Glu Ala Met Ile Asn Ala Gly Ala Thr Arg Ile Gly
```

```
                    245                 250                 255
Thr Ser Ser Gly Val Ala Ile Val Thr Gly Gly Thr Gly Arg Ala Asp
            260                 265                 270
Thr Lys Trp
        275

<210> SEQ ID NO 28
<211> LENGTH: 225
<212> TYPE: PRT
<213> ORGANISM: Listeria innocua

<400> SEQUENCE: 28

Met Thr Ile Ala Lys Met Ile Asp His Thr Ala Leu Lys Pro Asp Thr
1               5                   10                  15

Thr Lys Glu Gln Ile Leu Thr Leu Thr Lys Glu Ala Arg Glu Tyr Gly
            20                  25                  30

Phe Ala Ser Val Cys Val Asn Pro Thr Trp Val Lys Leu Ser Ala Glu
        35                  40                  45

Gln Leu Ser Gly Ala Glu Ser Val Val Cys Thr Val Ile Gly Phe Pro
    50                  55                  60

Leu Gly Ala Asn Thr Pro Glu Val Lys Ala Phe Glu Val Lys Asn Ala
65                  70                  75                  80

Ile Glu Asn Gly Ala Lys Glu Val Asp Met Val Ile Asn Ile Gly Ala
                85                  90                  95

Leu Lys Asp Lys Asp Glu Leu Val Glu Arg Asp Ile Arg Ala Val
            100                 105                 110

Val Asp Ala Ala Lys Gly Lys Ala Leu Val Lys Val Ile Glu Thr
            115                 120                 125

Cys Leu Leu Thr Asp Glu Glu Lys Val Arg Ala Cys Glu Ile Ala Val
    130                 135                 140

Lys Ala Gly Thr Asp Phe Val Lys Thr Ser Thr Gly Phe Ser Thr Gly
145                 150                 155                 160

Gly Ala Thr Ala Glu Asp Ile Ala Leu Met Arg Lys Thr Val Gly Pro
                165                 170                 175

Asn Ile Gly Val Lys Ala Ser Gly Gly Val Arg Thr Lys Glu Asp Val
            180                 185                 190

Glu Lys Met Ile Glu Ala Gly Ala Thr Arg Ile Gly Ala Ser Ala Gly
        195                 200                 205

Val Ala Ile Val Ser Gly Glu Lys Pro Ala Lys Pro Asp Asn Thr Lys
    210                 215                 220

Trp
225

<210> SEQ ID NO 29
<211> LENGTH: 240
<212> TYPE: PRT
<213> ORGANISM: Bacillus halodurans

<400> SEQUENCE: 29

Met Ser Arg Ser Ile Ala Gln Met Ile Asp His Thr Leu Leu Lys Pro
1               5                   10                  15

Asn Thr Thr Glu Asp Gln Ile Val Lys Leu Cys Glu Glu Ala Lys Glu
            20                  25                  30

Tyr Ser Phe Ala Ser Val Cys Val Asn Pro Thr Trp Val Ala Leu Ala
        35                  40                  45

Ala Gln Leu Leu Lys Asp Ala Pro Asp Val Lys Val Cys Thr Val Ile
```

-continued

```
                 50                  55                  60
Gly Phe Pro Leu Gly Ala Thr Thr Pro Glu Val Lys Ala Phe Glu Thr
 65                  70                  75                  80

Thr Asn Ala Ile Glu Asn Gly Ala Thr Glu Val Asp Met Val Ile Asn
                 85                  90                  95

Ile Gly Ala Leu Lys Asp Lys Gln Tyr Glu Leu Val Gly Arg Asp Ile
            100                 105                 110

Gln Ala Val Val Lys Ala Glu Gly Lys Ala Leu Thr Lys Val Ile
        115                 120                 125

Ile Glu Thr Ser Leu Leu Thr Glu Glu Lys Lys Ala Ala Cys Glu
    130                 135                 140

Leu Ala Val Lys Ala Gly Ala Asp Phe Val Lys Thr Ser Thr Gly Phe
145                 150                 155                 160

Ser Gly Gly Gly Ala Thr Ala Glu Asp Ile Ala Leu Met Arg Lys Val
                165                 170                 175

Val Gly Pro Asn Leu Gly Val Lys Ala Ser Gly Val Arg Asp Leu
            180                 185                 190

Ser Asp Ala Lys Ala Met Ile Asp Ala Gly Ala Thr Arg Ile Gly Ala
        195                 200                 205

Ser Ala Gly Val Ala Ile Val Asn Gly Glu Arg Ser Glu Gly Ser Thr
    210                 215                 220

Lys Trp Thr Ala Ala Gly Ala Ala Thr Cys Ala Cys Thr Gly Gly
225                 230                 235                 240

<210> SEQ ID NO 30
<211> LENGTH: 222
<212> TYPE: PRT
<213> ORGANISM: Streptococcus suis

<400> SEQUENCE: 30

Met Lys Leu Asn Lys Tyr Ile Asp His Thr Ile Leu Lys Pro Glu Thr
 1               5                  10                  15

Thr Gln Glu Gln Val Glu Lys Ile Leu Ala Glu Ala Lys Glu Tyr Asp
            20                  25                  30

Phe Ala Ser Val Cys Val Asn Pro Thr Trp Val Ala Leu Ala Ala Glu
        35                  40                  45

Ser Leu Lys Asp Ser Asp Val Lys Val Cys Thr Val Ile Gly Phe Pro
    50                  55                  60

Leu Gly Ala Asn Thr Pro Ala Val Lys Ala Phe Glu Thr Lys Asp Ala
 65                  70                  75                  80

Ile Ser Asn Gly Ala Asp Glu Ile Asp Met Val Ile Asn Ile Gly Ala
                 85                  90                  95

Leu Lys Thr Gly Asn Tyr Asp Leu Val Leu Glu Asp Ile Lys Ala Val
            100                 105                 110

Val Ala Ala Ser Gly Asp Lys Leu Val Lys Val Ile Glu Ala Cys
        115                 120                 125

Leu Leu Thr Asp Asp Glu Lys Val Lys Ala Cys Gln Leu Ser Gln Glu
    130                 135                 140
```

```
Ala Gly Ala Asp Tyr Val Lys Thr Ser Thr Gly Phe Ser Thr Gly Gly
145                 150                 155                 160

Ala Thr Val Ala Asp Val Ala Leu Met Arg Lys Thr Val Gly Pro Asp
                165                 170                 175

Met Gly Val Lys Ala Ser Gly Gly Ala Arg Ser Tyr Glu Asp Ala Ile
            180                 185                 190

Ala Phe Ile Glu Ala Gly Ala Ser Arg Ile Gly Ala Ser Ser Gly Val
        195                 200                 205

Ala Ile Met Asn Gly Ala Gln Ala Asp Gly Asp Thr Lys Trp
    210                 215                 220
```

PROCESS FOR PREPARING CHIRAL COMPOUNDS

This application is a divisional application of U.S. Ser. No. 12/671,752 filed Feb. 1, 2011, which is a 371 application of PCT/IB2008/002016 filed on Jul. 23, 2008, which claims benefit of provisional application U.S. Ser. No. 60/953,725 filed on Aug. 3, 2007, all of which are incorporated herein by reference in their entirety.

BACKGROUND OF THE INVENTION

The present invention is directed to a 2-deoxyribose-5-phosphate aldolase (DERA) chemoenzymatic process for making chiral compounds.

The use of DERA (deoxyribose aldolase) family of aldolases in chemoenzymatic processes has been described. See U.S. Pat. No. 5,795,749, WO 03/006656, WO 2004/027075, WO 2005/012246; Gijsen, H. J. M., et al. JACS, 1994, 116, 8422-8423; Gijsen, H. J. M., et al., JACS, 1995, 117, 7585-7591; Greenberg, W. A., et al., PNAS, 2004, 101, 5788-5793, U.S. Pat. No. 6,964,863 and Biotechonol J, 101, pgs 537-548 (2006). However, some of the processes provided poor overall yield as well as a mixture of products. In addition, the processes were limited to specific substrates. Accordingly, there exists a need in the art for a chemoenzymatic process that is effective and efficient for alternative substrates.

SUMMARY OF THE INVENTION

The present invention relates to a process comprising the step of reacting acetaldehyde with an N-protected aminoaldehyde substrate selected from the group consisting of 3-phthalimidopropionaldehyde, N-formyl-3-aminopropionaldehyde, 3-succinimido-propionaldehyde or N-diBoc-3-aminopropionaldehyde under aldolase-catalyzed aldol condensation conditions to form the corresponding lactol.

The present invention also relates to a process wherein said aldolase is a 2-deoxyribose-5-phosphate aldolase (DERA) aldolase.

The present invention also relates to a process wherein said aldolase is DERA 04 comprising a nucleotide sequence of SEQ ID NO: 2 or an amino acid sequence of SEQ ID NO: 17;
DERA 06 comprising a nucleotide sequence of SEQ ID NO: 3 or an amino acid sequence of SEQ ID NO: 18;
DERA 101 comprising a nucleotide sequence of SEQ ID NO: 8 or an amino acid sequence of SEQ ID NO: 23;
DERA 102 comprising a nucleotide sequence of SEQ ID NO: 9 or an amino acid sequence of SEQ ID NO: 24;
DERA 103 comprising a nucleotide sequence of SEQ ID NO: 10 or an amino acid sequence of SEQ ID NO: 25;
DERA 104 comprising a nucleotide sequence of SEQ ID NO: 11 or an amino acid sequence of SEQ ID NO: 26;
DERA 105 comprising a nucleotide sequence of SEQ ID NO: 12 or an amino acid sequence of SEQ ID NO: 27;
DERA 106 comprising a nucleotide sequence of SEQ ID NO: 13 or an amino acid sequence of SEQ ID NO: 28;
DERA 107 comprising a nucleotide sequence of SEQ ID NO: 14 or an amino acid sequence of SEQ ID NO: 29;
DERA 108 comprising a nucleotide sequence of SEQ ID NO: 15 or an amino acid sequence of SEQ ID NO: 30;
or an aldolase having an amino acid sequence identity of at least about 20% thereof.

More specifically, the present invention also relates to a process wherein said aldolase is DERA 04 comprising a nucleotide sequence of SEQ ID NO: 2 or an amino acid sequence of SEQ ID NO: 17; DERA 06 comprising a nucleotide sequence of SEQ ID NO: 3 or an amino acid sequence of SEQ ID NO: 18 or DERA 102 comprising a nucleotide sequence of SEQ ID NO: 9 or an amino acid sequence of SEQ ID NO: 24.

More specifically, the present invention also relates to a process wherein said aldolase is DERA 04 comprising a nucleotide sequence of SEQ ID NO: 2 or an amino acid sequence of SEQ ID NO: 17.

More specifically, the present invention also relates to a process wherein said aldolase is DERA 102 comprising a nucleotide sequence of SEQ ID NO: 9 or an amino acid sequence of SEQ ID NO: 24.

The present invention also relates to a process wherein said N-protected aminoaldehyde substrate is 3-phthalimidopropionaldehyde.

The present invention also relates to a process wherein said N-protected aminoaldehyde substrate is N-formyl-3-aminopropionaldehyde or 3-succinimido-propionaldehyde.

The present invention also relates to a process wherein said N-protected aminoaldehyde substrate is N-diBoc-3-aminopropionaldehyde.

The present invention relates to a process comprising the step of:
(a) reacting an aldehyde with an N-protected aminoaldehyde substrate selected from the group consisting of 3-phthalimidopropionaldehyde, N-formyl-3-aminopropionaldehyde, 3-succinimido-propionaldehyde or N-diBoc-3-aminopropionaldehyde under aldolase-catalyzed aldol condensation conditions to form the corresponding lactol;
(b) oxidizing the lactol so formed to yield the corresponding lactone;
(c) reacting the lactone so formed with isopropyl alcohol and acetone under acidic catalysis to yield the corresponding isopropyl acetonide ester;
(d) treating the isopropyl acetonide ester so formed with a base to yield the corresponding amino acetonide isopropyl ester.

The present invention relates to a process comprising the step of:
(a) reacting an aldehyde with an N-protected aminoaldehyde substrate selected from the group consisting of 3-phthalimidopropionaldehyde, N-formyl-3-aminopropionaldehyde, 3-succinimido-propionaldehyde or N-diBoc-3-aminopropionaldehyde under aldolase-catalyzed aldol condensation conditions to form the corresponding lactol;
(b) oxidizing the lactol so formed to yield the corresponding lactone;
(c) reacting the lactone so formed with cyclopentanone to yield the corresponding cyclopentylidene phthalimido isopropyl ester; and
(d) treating the cyclopentylidene phthalimido isopropyl ester so formed with base to yield the corresponding amino cyclopentylidene isopropyl ester.

The present invention relates to a process comprising the steps of:
(a) reacting an aldehyde with an N-protected aminoaldehyde substrate selected from the group consisting of 3-phthalimidopropionaldehyde, N-formyl-3-aminopropionaldehyde, 3-succinimido-propionaldehyde or N-diBoc-3-aminopropionaldehyde under aldolase-catalyzed aldol condensation conditions to form the corresponding lactol;
(b) dehydrogenating the lactol so formed under catalytic dehydrogenation conditions to yield the corresponding heptanoic acid;
(c) treating said 3,5-dihydroxyheptanoic acid so formed with dicyclohexylamine to form the corresponding salt;

(d) reacting the salt so formed with triisopropyl orthoformate and acetone under acidic catalysis to yield the corresponding isopropyl acetonide ester; and (e) treating the isopropyl acetonide ester so formed with base to yield the corresponding amino dicyclohexylamine isopropyl ester.

The present invention relates to a process comprising the steps of:

(a) reacting an aldehyde with an N-protected aminoaldehyde substrate selected from the group consisting of 3-phthalimidopropionaldehyde, N-formyl-3-aminopropionaldehyde, 3-succinimido-propionaldehyde or N-diBoc-3-aminopropionaldehyde under aldolase-catalyzed aldol condensation conditions to form the corresponding lactol;

(b) oxidizing the lactol so formed to yield the corresponding 3,5-dihydroxyheptanoic acid;

(c) treating said 3,5-dihydroxyheptanoic acid with dicyclohexylamine to form the corresponding salt; and (d) reacting the salt so formed with triisopropyl orthoformate to yield the corresponding isopropyl acetonide ester; and (e) treating the isopropyl acetonide ester so formed with base to yield the corresponding amino acetonide isopropyl ester.

The present invention relates to a process comprising the step of reacting an aldehyde with an aminoaldehyde substrate or an N-protected aminoaldehyde substrate under DERA 101, DERA 102, DERA 103, DERA 104, DERA 105, DERA 106, DERA 107 or DERA 108 aldolase-catalyzed aldol condensation conditions to form the corresponding lactol.

The present invention also relates to a process wherein said aminoaldehyde or said N-protected aminoaldehyde is N-Boc-3-aminopropionaldehyde, 3-aminopropionaldehyde, aminoacetaldehyde, N—CBz-3-aminopropionaldehyde, N-acetyl-3-aminopropionaldehyde, N-Fmoc-3-aminopropionaldehyde, or N-Fmoc-aminoacetaldehyde.

More specifically, the present invention also relates to a process wherein said N-protected aminoaldehyde is N-Boc-3-aminopropionaldehyde More specifically, the present invention also relates to a process wherein said aminoaldehyde or said N-protected aminoaldehyde is N—CBz-3-aminopropionaldehyde or N-Fmoc-3-aminopropionaldehyde.

More specifically, the present invention also relates to a process wherein said aminoaldehyde or said N-protected aminoaldehyde is N—CBz-3-aminopropionaldehyde.

The present invention also relates to a process wherein said aldolase is DERA 102.

The present invention relates to a process comprising the step of reacting an aldehyde with an aminoaldehyde substrate or an N-protected aminoaldehyde substrate under DERA 101, DERA 102, DERA 103, DERA 104, DERA 105, DERA 106, DERA 107 or DERA 108 aldolase-catalyzed aldol condensation conditions to form the corresponding lactol, and oxidizing the lactol so formed to yield the corresponding lactone.

The present invention relates to a process comprising the steps of:

(a) reacting an aldehyde with an aminoaldehyde substrate or an N-protected aminoaldehyde substrate under DERA 101, DERA 102, DERA 103, DERA 104, DERA 105, DERA 106, DERA 107 or DERA 108 aldolase-catalyzed aldol condensation conditions to form the corresponding lactol;

(b) dehydrogenating the lactol so formed under catalytic dehydrogenation conditions to yield the corresponding 3,5-dihydroxyheptanoic acid;

(c) treating said 3,5-dihydroxyheptanoic acid so formed with dicyclohexylamine to form the corresponding salt; and (d) reacting the salt so formed with triisopropyl orthoformate to yield the corresponding isopropyl acetonide ester.

The present invention relates to a process comprising the steps of:

(a) reacting an aldehyde with an aminoaldehyde substrate or an N-protected aminoaldehyde substrate under DERA 101, DERA 102, DERA 103, DERA 104, DERA 105, DERA 106, DERA 107 or DERA 108 aldolase-catalyzed aldol condensation conditions to form the corresponding lactol;

(b) oxidizing the lactol so formed to yield the corresponding 3,5-dihydroxyheptanoic acid;

(c) treating said 3,5-dihydroxyheptanoic acid with dicyclohexylamine to form the corresponding salt; and (d) reacting the salt so formed with triisopropyl orthoformate to yield the corresponding isopropyl acetonide ester.

The present invention relates to a process comprising the step of reacting an aldehyde with an aminoaldehyde substrate compound of the general formula (I):

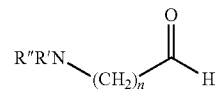

wherein:

n=1, 2, 3 or 4;

R' is hydrogen or an N-protecting group;

R" is hydrogen or an N-protecting group; or R' and R" taken together with nitrogen to which they are attached form a 5- or 6-membered heterocyclic moiety, under DERA 101, DERA 102, DERA 103, DERA 104, DERA 105, DERA 106, DERA 107 or DERA 108 aldolase-catalyzed aldol condensation conditions to form the corresponding lactol.

The present invention also relates to the compound 2-[2-(4,6-Dihydroxy-tetrahydro-pyran-2-yl]-isoindole-1,3-dione.

More specifically, the present invention also relates to a compound of the formula

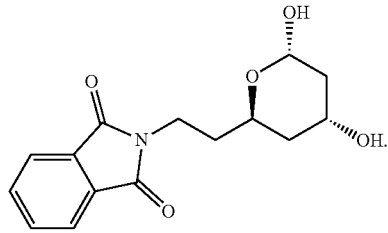 [SMILES: O=C1c2ccccc2C(=O)N1CC[C@@H]1C[C@@H](O)C[C@@H](O)O1]

More specifically, the present invention also relates to a compound of the formula

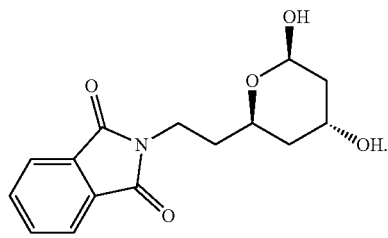 [SMILES: O=C1c2ccccc2C(=O)N1CC[C@@H]1C[C@@H](O)C[C@H](O)O1]

The present invention also relates to the compound of the formula

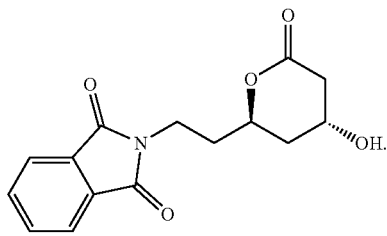 [SMILES: O=C1C[C@H](O)C[C@@H](CCN2C(=O)c3ccccc3C2=O)O1]

The present invention also relates to the compound of the formula

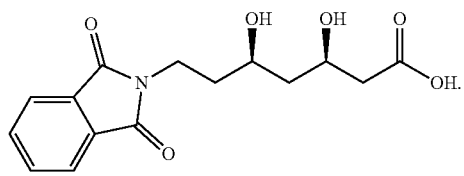 [SMILES: O=C(O)C[C@H](O)C[C@H](O)CCN1C(=O)c2ccccc2C1=O]

The present invention also relates to the compound of the formula

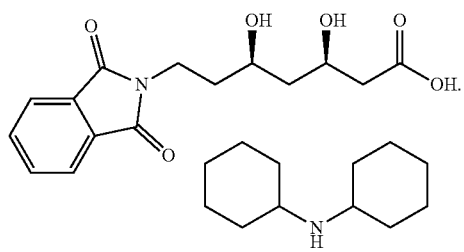

The present invention also relates to the compound of the formula

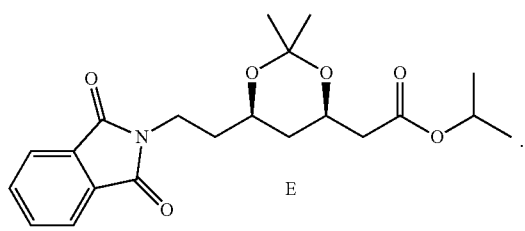 [SMILES: CC(C)OC(=O)C[C@H]1C[C@@H](CCN2C(=O)c3ccccc3C2=O)OC(C)(C)O1]

E

The present invention also relates to the compound of the formula

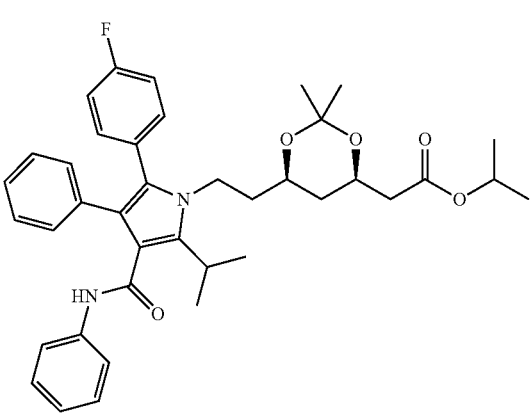 [SMILES: CC(C)OC(=O)C[C@H]1C[C@@H](CCn2c(-c3ccc(F)cc3)c(-c3ccccc3)c(C(=O)Nc3ccccc3)c2C(C)C)OC(C)(C)O1]

The present invention also relates to the compound of the formula

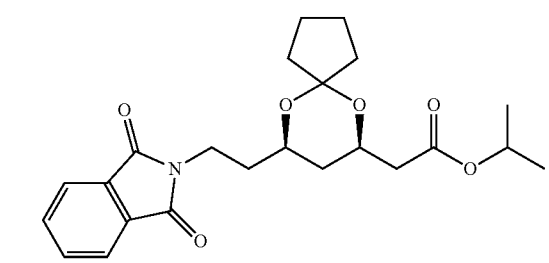 [SMILES: CC(C)OC(=O)C[C@H]1C[C@@H](CCN2C(=O)c3ccccc3C2=O)OC2(CCCC2)O1]

The present invention also relates to the compound of the formula

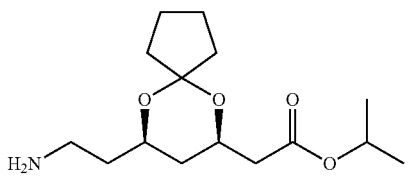 [SMILES: CC(C)OC(=O)C[C@H]1C[C@@H](CCN)OC2(CCCC2)O1]

The present invention also relates to the compound of the formula

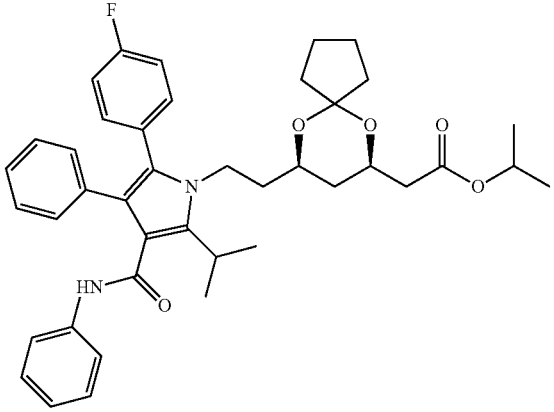 [SMILES: CC(C)OC(=O)C[C@H]1C[C@@H](CCn2c(-c3ccc(F)cc3)c(-c3ccccc3)c(C(=O)Nc3ccccc3)c2C(C)C)OC2(CCCC2)O1]

The present invention relates to a crystalline form of 4-fluoro-alpha-[2-methyl-1-oxopropyl]-gamma-oxo-N, beta-diphenylbenzenebutanamide characterized as having powder X-ray diffraction peaks of about 9.0, 12.7, 20.2, 22.6, and 25.2 degrees two-theta.

The present invention relates to a crystalline form of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide characterized as having powder X-ray diffraction peaks of about 6.3, 12.7, 16.8, 21.1 and 25.5 degrees two-theta.

DETAILED DESCRIPTION OF THE INVENTION

Definitions

Figure 1:
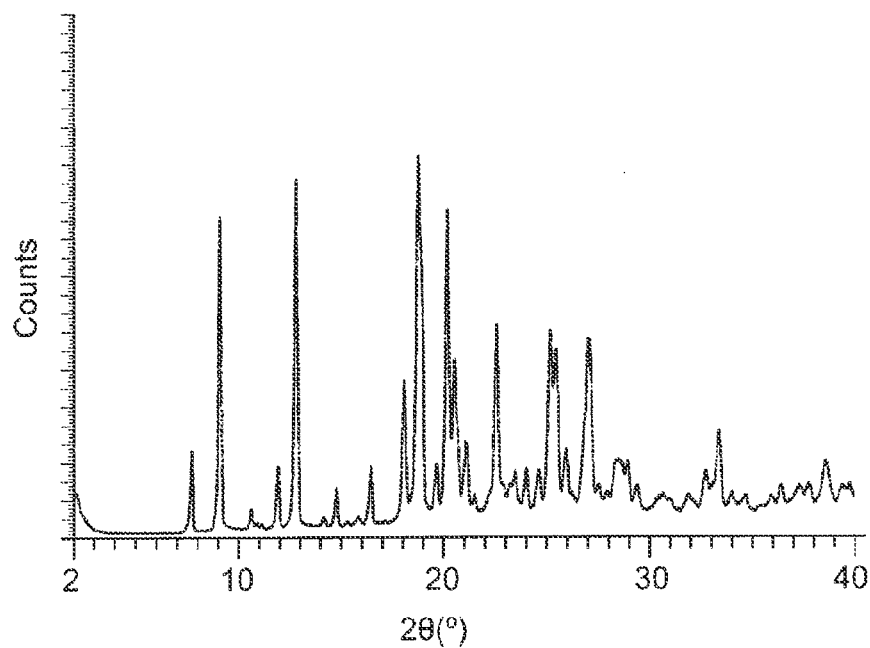
FIG. 1 is an experimental powder X-ray diffraction pattern for 4-fluoro-alpha-[2-methyl-1-oxopropyl]-gamma-oxo-N, beta-diphenylbenzenebutanamide. The scale of the abscissa is degrees two-theta. The ordinate is the intensity of the counts.

Unless indicated otherwise, the following terms are defined as follows:

The article "a" or "an" as used herein refers to both the singular and plural form of the object to which it refers.

The term "aldolase-catalyzed aldol condensation conditions" as used herein refers to any aldol condensation conditions known in the art that can be catalyzed by an aldolase, as described herein.

The aldehyde for use in the present invention may be any aldehyde that will undergo an aldol condensation with a substrate, as described herein, in the presence of an aldolase, as described herein. An example of suitable aldehyde is, but is not limited to, acetaldehyde.

A substrate for use in the present invention may be any aminoaldehyde or N-protected aminoaldehyde. Such an aminoaldehyde or N-protected aminoaldehyde will react with an aldehyde under aldolase-catalyzed aldol condensation conditions, each as described herein.

Suitable N-protecting groups for the aminoaldehyde include, but are not limited to, phthalimido, N-formyl, succinimdo, di-butoxycarbonyl (di-Boc), benzyloxycarbonyl (CBz), butoxycarbonyl (Boc), 9-fluorenylmethoxycarbonyl (Fmoc), benzyl, and dibenzyl.

Examples of a suitable aminoaldehyde substrate include, but are not limited to:

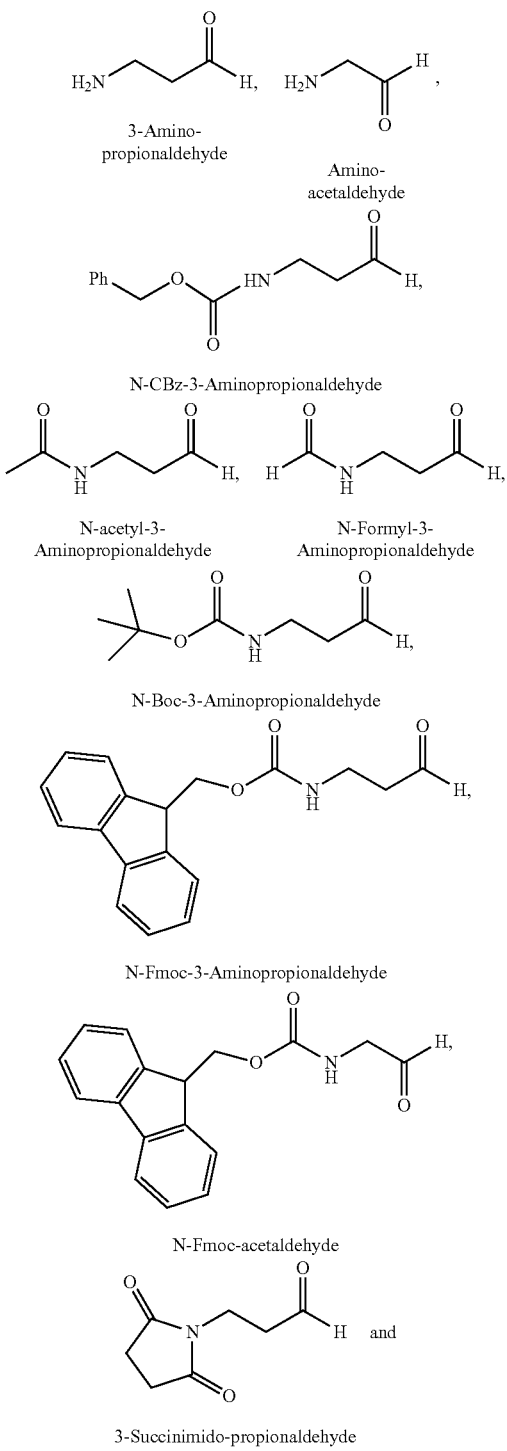

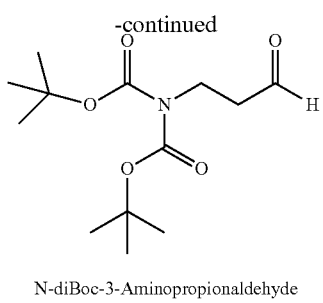

N-diBoc-3-Aminopropionaldehyde

In one embodiment of the invention, the aminoaldehyde substrate is 3-phthalimidopropionaldehyde, N-formyl-3-aminopropionaldehyde, N-Boc-3-aminopropionaldehyde, 3-succinimido-propionaldehyde or N-diBoc-3-aminopropionaldehyde. In another embodiment of the invention, the aminoaldehyde substrate is N—CBz-3-aminopropionaldehyde or N-Fmoc-3-aminopropionaldehyde. In another embodiment of the invention, the aminoaldehyde substrate is 3-amino-propionaldehyde. In another embodiment of the invention, the aminoaldehyde substrate is amino-acetaldehyde. In another embodiment of the invention, the aminoaldehyde substrate is N—CBz-3-aminopropionaldehyde (commercially available from Aldrich). In another embodiment of the invention, the aminoaldehyde substrate is N-acetyl-3-aminopropionaldehyde. In another embodiment of the invention, the aminoaldehyde substrate is N-Fmoc-3-aminopropionaldehyde.

Both N-Fmoc-aminoaldehydes were obtained via standard Dess-Martin oxidation of the corresponding N-Fmoc aminoalcohol.

The N-acetyl-3-aminopropionaldehyde was obtained from 3-amino-1-propanol by a two step procedure: N-acetylation of the 3-amino-1-propanol by methyl actetate followed by Dess-Martin oxidation to give the desired product with the correct ESI-MS $[M+H]^+$ 116.25 and $[M+Na]^+$ 138.20.

An aldolase for use in the present invention may be any enzyme that has aldolase activity towards an aminoaldehyde substrate, N-protected aminoaldehyde substrate, or pyrrole aldehyde substrate, each as described herein. In one embodiment of the invention, the aldolase is a 2-deoxyribose-5-phosphate aldolase (DERA). Examples of a suitable DERA aldolase include, but are not limited to:

DERA 03 (*E. coli*) (commercially available from Sigma Aldrich, St. Louis, Mo.);

DERA 04 (William A. Greenberg, et al., PNAS, (2004), Vol. 101, No. 16, pp. 5788-5793 or a modified version thereof);

DERA 06 (GenBank Accession NP_294929 or a modified version thereof);

DERA 08 (GenBank Accession NP_465519 or a modified version thereof);

DERA 11 (GenBank Accession NP_439273);

DERA 12 (GenBank Accession NP_229359);

DERA 15 (Haruhiko Sakuraba, et al., *Journal of Biological Chemistry* (2003), Vol. 278, No. 12, pp 10799-10806);

DERA 101 (GenBank Accession NP_906068.1 or a modified version thereof);

DERA 102 (GenBank Accession NP_813976.1 or a modified version thereof);

DERA 103 (GenBank Accession NP_01130044.1 or a modified version thereof);

DERA 104 (GenBank Accession YP_924715.1 or a modified version thereof);

DERA 105 (GenBank Accession YP_148352.1 or a modified version thereof);

DERA 106 (GenBank Accession NP_471437.1 or a modified version thereof);

DERA 107 (GenBank Accession NP_242218.1 or a modified version thereof); and

DERA 108 (GenBank Accession ZP_00875069.1 or a modified version thereof).

In one embodiment of the invention, the aldolase is an aldolase having an amino acid sequence identity of at least about 20% thereof; preferably, at least 70% thereof, to a DERA aldolase described herein. In one embodiment of the invention, the DERA aldolase is DERA 04, DERA 06 or DERA 102. In one embodiment of the invention, the DERA aldolase is DERA 102.

According to the invention, DERA 03, DERA 04, DERA 06, DERA 08, DERA 11, DERA 12, DERA 15, DERA 101, DERA 102, DERA 103, DERA 104, DERA 105, DERA 106, DERA 107 and DERA 108 are identified by their nucleotide sequences and amino acid sequences set forth in Examples 1-30.

More specifically, DERA 03 is an aldolase having a nucleotide sequence of SEQ ID NO: 1 and an amino acid sequence of SEQ ID NO: 16.

DERA 04 is an aldolase having a nucleotide sequence of SEQ ID NO: 2 and an amino acid sequence of SEQ ID NO: 17.

DERA 06 is an aldolase having a nucleotide sequence of SEQ ID NO: 3 and an amino acid sequence of SEQ ID NO: 18.

DERA 08 is an aldolase having a nucleotide sequence of SEQ ID NO: 4 and an amino acid sequence of SEQ ID NO: 19.

DERA 11 is an aldolase having a nucleotide sequence of SEQ ID NO: 5 and an amino acid sequence of SEQ ID NO: 20.

DERA 12 is an aldolase having a nucleotide sequence of SEQ ID NO: 6 and an amino acid sequence of SEQ ID NO: 21.

DERA 15 is an aldolase having a nucleotide sequence of SEQ ID NO: 7 and an amino acid sequence of SEQ ID NO: 22.

DERA 101 is an aldolase having a nucleotide sequence of SEQ ID NO: 8 and an amino acid sequence of SEQ ID NO: 23.

DERA 102 is an aldolase having a nucleotide sequence of SEQ ID NO: 9 and an amino acid sequence of SEQ ID NO: 24.

DERA 103 is an aldolase having a nucleotide sequence of SEQ ID NO: 10 and an amino acid sequence of SEQ ID NO: 25.

DERA 104 is an aldolase having a nucleotide sequence of SEQ ID NO: 11 and an amino acid sequence of SEQ ID NO: 26.

DERA 105 is an aldolase having a nucleotide sequence of SEQ ID NO: 12 and an amino acid sequence of SEQ ID NO: 27.

DERA 106 is an aldolase having a nucleotide sequence of SEQ ID NO: 13 and an amino acid sequence of SEQ ID NO: 28.

DERA 107 is an aldolase having a nucleotide sequence of SEQ ID NO: 14 and an amino acid sequence of SEQ ID NO: 29.

DERA 108 is an aldolase having a nucleotide sequence of SEQ ID NO: 15 and an amino acid sequence of SEQ ID NO: 30.

The DERA aldolases described herein can be prepared by any means known in the art, including but not limited to standard protocols for protein expression in recombinant *E. coli* (Sambrook and Russell, Molecular Cloning: A Laboratory Manual, 3$^{rd}$ Ed., Cold Spring Harbor, N.Y. 2001). As would be understood by one of skill in the art, modified versions of known DERA aldolases may be necessary or may result depending on cloning conditions and are encompassed by the present invention.

The following Schemes illustrate the present invention.

Preparation A

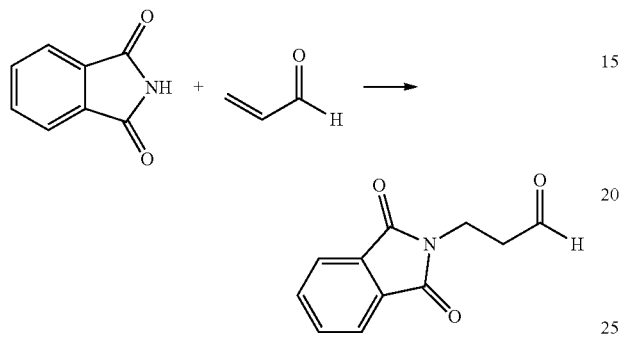

In Preparation A, 3-phthalimidopropionaldehyde is prepared by reacting phthalimide with acrolein in the presence of benzyltrimethyl ammonium hydroxide (Triton-B). The reaction is stirred at a temperature between about 53° C. to about 67.5° C., preferably about 60° C., for a time period between about 30 minutes to about 3 hours, preferably about 90 minutes.

Preparation B

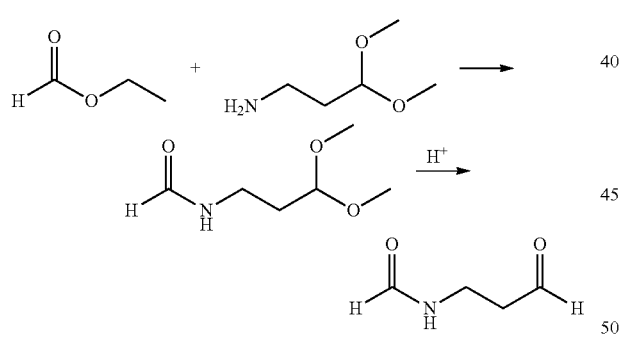

In Preparation B, N-formyl-3-aminopropionaldehyde is prepared by reacting ethyl formate with 1-amino-3,3-dimethoxypropane and treating the amide so formed with acid.

Preparation C

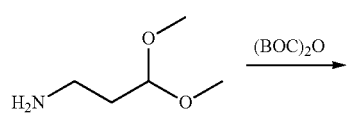

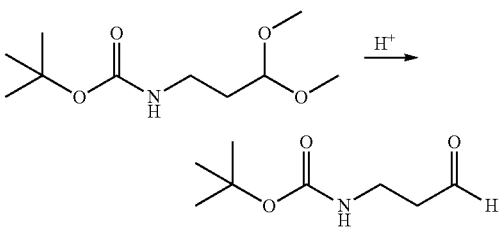

In Preparation C, N-Boc-3-aminopropionaldehyde is prepared by reacting 1-amino-3,3-dimethoxypropane with BOC anhydride and treating the amide so formed with acid.

Preparation D

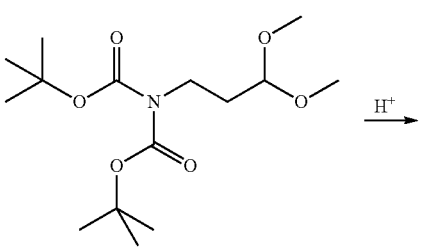

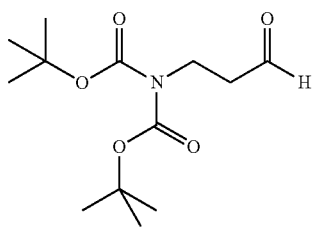

In Preparation D, N-di-Boc-3-aminopropionaldehyde is prepared by reacting 1-amino-3,3-dimethoxypropane with BOC anhydrdride in the presence of 4-di(methylamino)pyridine and treating the amide so formed with acid.

Preparation E 3-succinimidopropionaldehyde

Acrolein is added to a solution of succinimide in the presence of catalytic sodium ethoxide and a polar protic solvent, such as ethanol. The reaction mixture is stirred at a temperature between about 10° C. to about 40° C., preferably about 20-30° C., for a time period between about 20 hours to about 60 hours, preferably about 48 hours.

Scheme 1

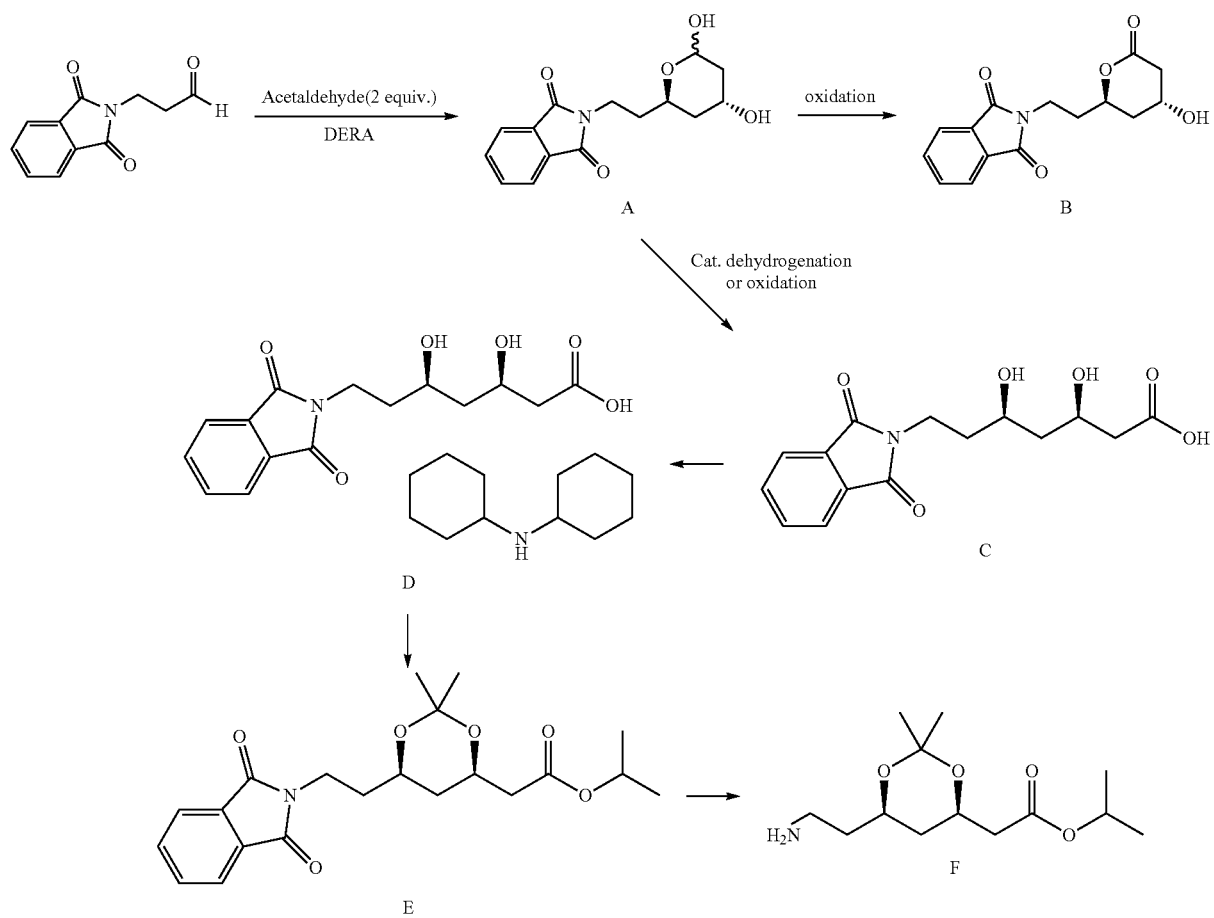

Scheme 1 describes in general a process encompassed by the present invention. As set forth in Scheme 1, a DERA aldolase catalyzes two sequential aldol condensation reactions between 3-phthalimidopropionaldehyde and 2 mol of acetaldehyde in the presence of other suitable solvents such as methyl tert-butyl ether (MTBE) and water to yield the protected desired amino-lactol (A). Suitable DERA aldolases include, but are not limited to, DERA 04, DERA 06, DERA 101, DERA 102, DERA 104, DERA 105, DERA 106, DERA107 and DERA 108, preferably DERA 04 and DERA 102. The acetaldehyde is added to the mixture of 3-phthalimidopropionaldehyde and DERA aldolase over a time period between about 7 hours to about 12 hours, preferably about 10 hours. The mixture so formed is further stirred at a temperature between about 15° C. to about 30° C., preferably about 22° C., for a time period between about 20 hours to about 60 hours, preferably about 48 hours.

The amino-lactol (A) can undergo catalytic (e.g. platinum on carbon or palladium on carbon) dehydrogenation to form carboxylic acid (C), which can then undergo lactonization to form (B).

Any catalytic dehydrogenation means known in the art to convert (A) to (C) are encompassed by the present invention. Examples of suitable catalysts include, but are not limited to, Pt/C, Pd/C, Pt/Bi/C, Pd/Bi/C and any other dehydrogenation catalysts. In one embodiment of the invention, the catalytic dehydrogenation is performed at about pH 7 to about pH 10 using air or oxygen as terminal oxidant.

Any lactonization means known in the art to convert carboxylic acid (C) to lactone (B) are encompassed by the present invention including, but not limited to, the use of acid catalysts such as, but not limited to, hydrochloric acid, sulfuric acid, methanesulfonic acid (MSA), p-toluenesulfonic acid (TSA) and any other lactonization acids known in the art. More specifically, the 7-(1,3-Dioxo-1,3-dihydro-isoindo-2-yl)-3,5-dihydroxy-heptanoic acid (C) is converted to the corresponding 2-[2-(4-Hydroxy-6-oxo-tetrahydro-pyran-2-yl]-isoindole-1,3-dione (B) by treating (C) with anhydrous hydrochloric acid in the presence of ethyl acetate. The reaction is stirred at room temperature for a time period between about 1 hour to about 4 hours, preferably about 2-3 hours.

Alternatively, oxidation of the lactol (A) to lactone (B) or carboxylic acid (C) can be performed by use of any oxidation means known in the art that will achieve the desired transformation. More specifically, 2-[2-(4,6-dihydroxy-tetrahydro-pyran-2-yl]-isoindole-1,3-dione (A) is converted to the corresponding 2-[2-(4-hydroxy-6-oxo-tetrahydro-pyran-2-yl]-isoindole-1,3-dione (B) by oxidizing (A) in the presence of an oxidizing agent, such as sodium chlorite. The reaction is stirred at a temperature between about 10° C. to about 30° C., preferably about 23° C., for a time period between about 2 hours to about 6 hours, preferably about 4 hours. The 2-[2-(4,6-dihydroxy-tetrahydro-pyran-2-yl]-isoindole-1,3-dione (A) can also be converted to the corresponding 7-(1,3-dioxo-1,3-dihydro-isoindo-2-yl)-3,5-dihydroxy-heptanoic acid (C) by oxidizing (A) in the presence of an oxidizing agent, such as sodium chlorite, a phosphate buffer, a polar aprotic solvent, such as dimethyl sulfoxide, and an alcohol, such as isopropanol. The reaction is maintained at room temperature and a pH between about 5 to about 6 for a time period between about 2 hours to about 6 hours, preferably about 4 hours.

The 7-(1,3-dioxo-1,3-dihydro-isoindo-2-yl)-3,5-dihydroxy-heptanoic acid (C) is converted to the corresponding dicyclohexyl amine (DCA) salt (D) by treating (C) with dicyclohexyl amine in the presence of ethyl acetate. The DCA salt (D) is then converted to the phthalimido acetonide isopropyl ester (E) by reacting (D) with DCM, triisopropyl orthoformate in the presence of acetone and methanesulfonic acid.

The phthalimido acetonide isopropyl ester (E) may also be prepared by reacting 2-[2-(4-hydroxy-6-oxo-tetrahydro-pyran-2-yl]-isoindole-1,3-dione (B) with isopropyl alcohol in the presence of acetone and methanesulfonic acid (MSA). The reaction mixture is stirred at room temperature at a pH between about 1 to about 2, preferably about 1.5, for a time period between about 20 hours to about 28 hours, preferably about 24 hours.

The phthalimido acetonide isopropyl ester (E) is deprotected to give the corresponding amino acetonide isopropyl ester (F) by treating (E) with a base, such as primary amine, i.e. an alkylamine, diamine such as ethylene diamine or an hydroxylamine, in the presence of a polar protic solvent, such as methanol. The reaction mixture is stirred at room temperature for a time period between about 30 minutes to about 4 hours, preferably about 2 hours.

The amino acetonide isopropyl ester (F) can be further reacted with 4-fluoro-alpha-[2-methyl-1-oxopropyl]-gamma-oxo-N, beta-diphenylbenzenebutanamide of formula II

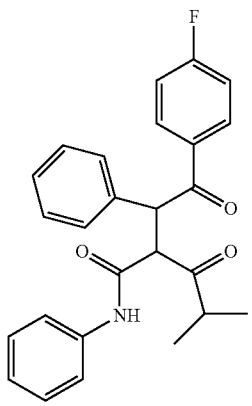

II to give the corresponding pyrrole ring containing acetonide isopropyl ester of formula III below

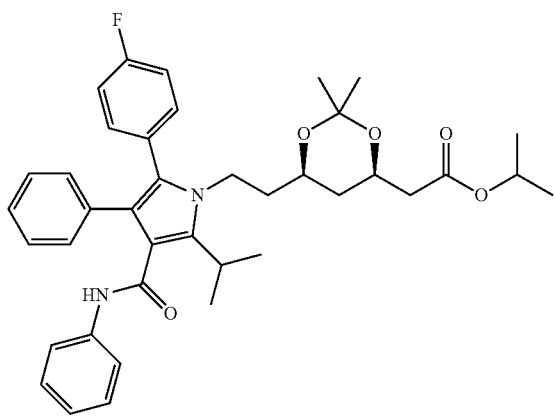

III

According to the invention, as would be understood by one of skill in the art, the stereoselectivity of the enzymatic step can be confirmed via chemical preparation of racemic standards and the development of the related chiral chromatographic methods.

The PXRD pattern for 4-fluoro-alpha-[2-methyl-1-oxopropyl]-gamma-oxo-N, beta-diphenylbenzenebutanamide is shown in FIG. 1.

Figure 2:
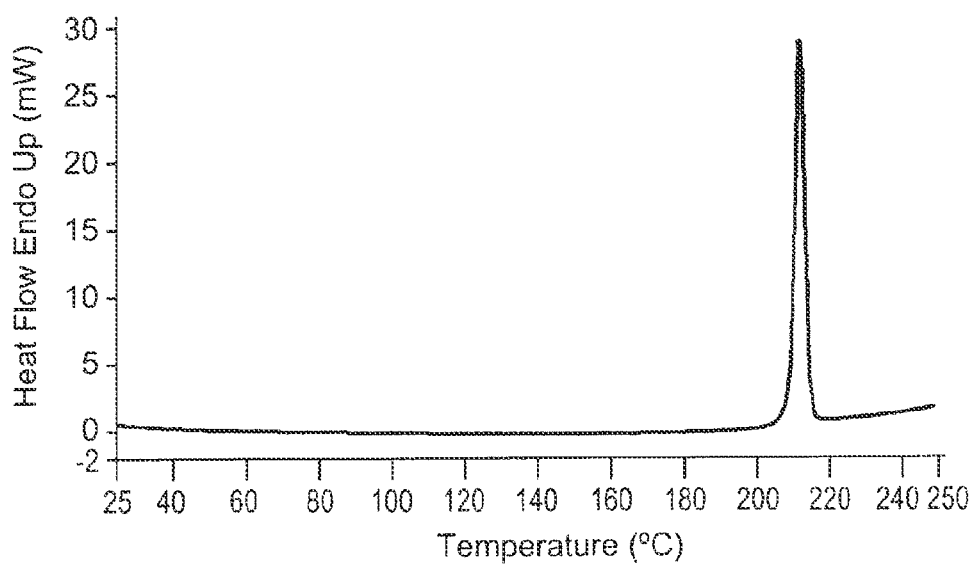
FIG. 2 is the differential scanning calorimetry (DSC) thermogram for 4-fluoro-alpha-[2-methyl-1-oxopropyl]-gamma-oxo-N, beta-diphenylbenzenebutanamide.
Figure 3A:
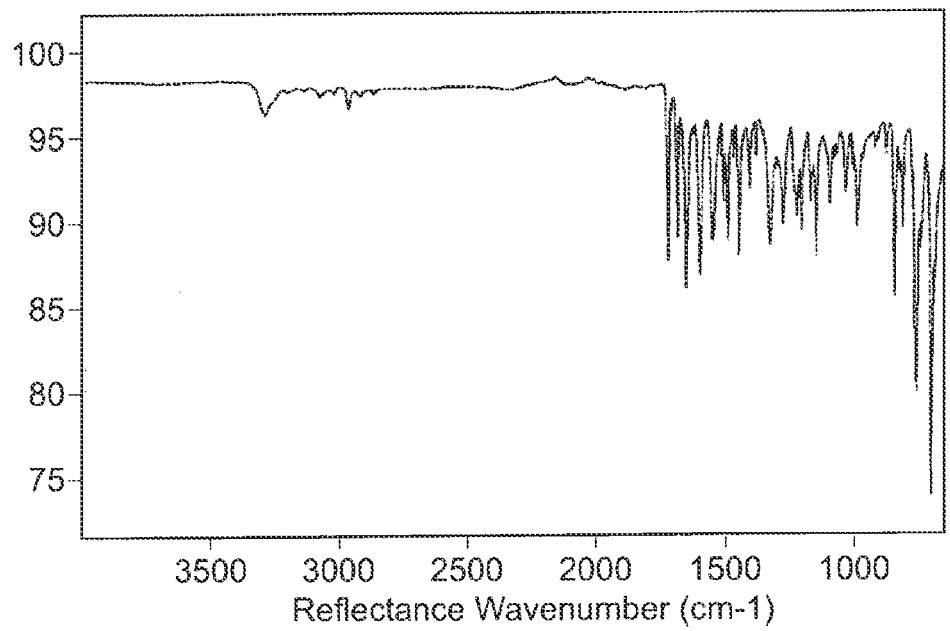
FIG. 3A is the infrared (FTIR) spectrum for 4-fluoro-alpha-[2-methyl-1-oxopropyl]-gamma-oxo-N, beta-diphenylbenzenebutanamide showing reflectance wavenumbers from 3500 to 1000 cm$^{-1}$.
Figure 3B:
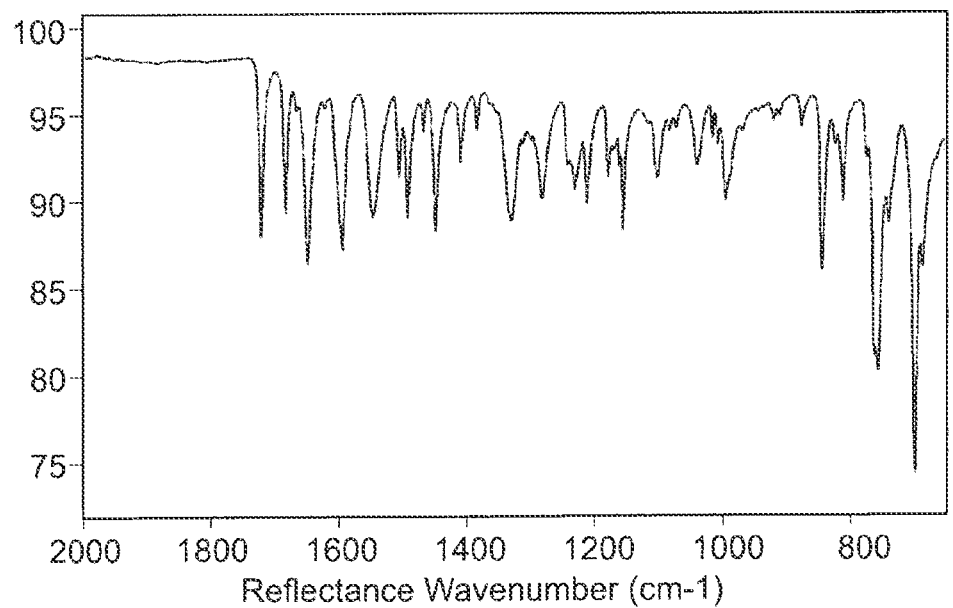
FIG. 3B is the infrared (FTIR) spectrum for 4-fluoro-alpha-[2-methyl-1-oxopropyl]-gamma-oxo-N, beta-diphenylbenzenebutanamide showing reflectance wavenumbers from 2000 to 800 cm$^{-1}$.
Figure 4A:
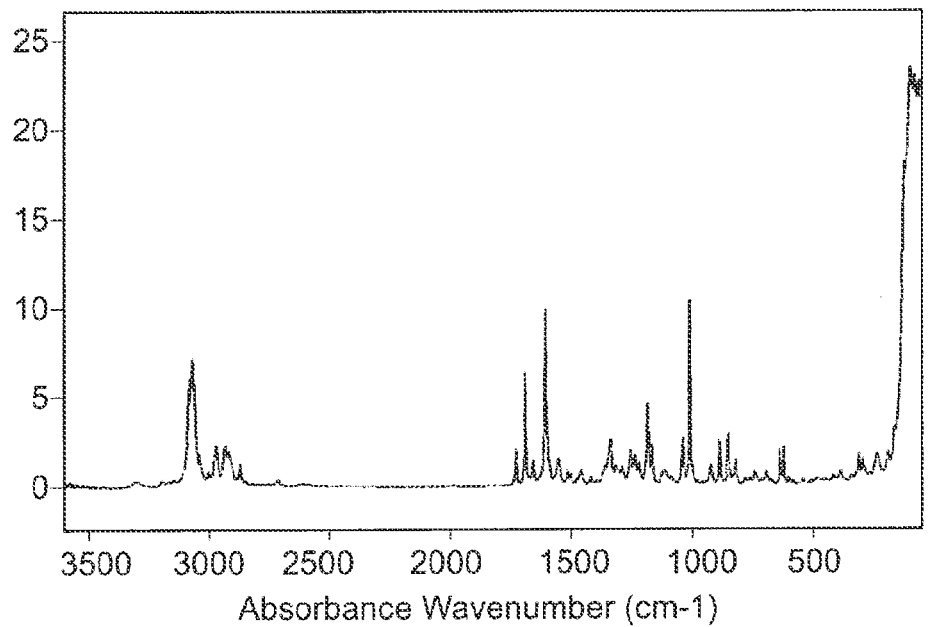
FIG. 4A is the Raman spectrum for 4-fluoro-alpha-[2-methyl-1-oxopropyl]-gamma-oxo-N, beta-diphenylbenzenebutanamide showing absorbance wavenumbers from 3500 to 500 cm$^{-1}$.
Figure 4B:
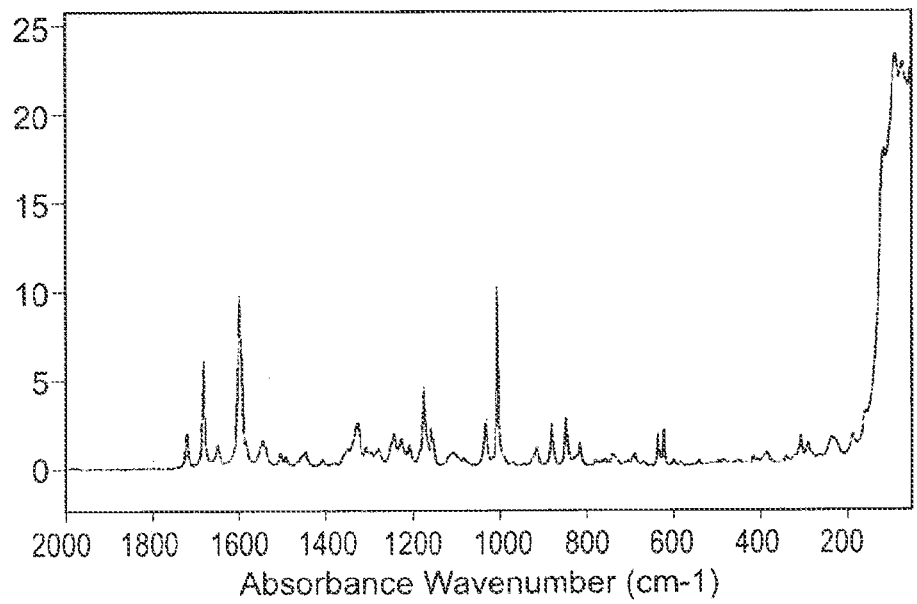
FIG. 4B is the Raman spectrum for 4-fluoro-alpha-[2-methyl-1-oxopropyl]-gamma-oxo-N, beta-diphenylbenzenebutanamide showing absorbance wavenumbers from 2000 to 200 cm$^{-1}$.

The main peaks (greater than 13% relative intensity) are given in Table 1. 4-fluoro-alpha-[2-methyl-1-oxopropyl]-gamma-oxo-N, beta-diphenylbenzenebutanamide displays characteristic diffraction peaks at 9.0, 12.7, 20.2, 22.6 and 25.2 degrees two theta±0.1 degree. The DSC thermogram is shown in FIG. 2. 4-fluoro-alpha-[2-methyl-1-oxopropyl]-gamma-oxo-N, beta-diphenylbenzenebutanamide shows a sharp endothermic peak at 213° C.±2° C. The FT-IR spectrum is illustrated in FIG. 3. The FT-IR peak table is given in Table 2. 4-fluoro-alpha-[2-methyl-1-oxopropyl]-gamma-oxo-N, beta-diphenylbenzenebutanamide displays characteristic peaks at 696, 1492, 1327, 843, 1151 $cm^{-1}$ (in this order). The FT-Raman spectrum is illustrated in FIG. 4. The FT-Raman peak table is given in Table 3. 4-fluoro-alpha-[2-methyl-1-oxopropyl]-gamma-oxo-N, beta-diphenylbenzenebutanamide displays characteristic peaks at 1004, 115, 87, 877, 1601 $cm^{-1}$.

Table 1: Main PXRD Peaks for 4-fluoro-alpha-[2-methyl-1-oxopropyl]-gamma-oxo-N, beta-diphenylbenzenebutanamide

TABLE 1

Main PXRD Peaks for 4-fluoro-alpha-[2-methyl-1-oxopropyl]-gamma-oxo-N, beta-diphenylbenzenebutanamide

| Angle 2-Theta (°) | Relative Intensity (%) |
|---|---|
| 7.6 | 22.8 |
| 9.0 | 84.3 |
| 11.8 | 18.4 |
| 12.7 | 93.8 |
| 14.7 | 12.8 |
| 16.4 | 18.5 |
| 18.0 | 41.1 |
| 18.8 | 100.0 |
| 18.9 | 78.0 |
| 19.6 | 19.0 |
| 20.2 | 86.4 |
| 20.5 | 46.6 |
| 20.7 | 31.1 |
| 21.1 | 25.0 |
| 22.6 | 55.9 |
| 22.9 | 14.2 |
| 23.2 | 14.0 |
| 23.5 | 17.0 |
| 24.0 | 18.0 |
| 24.7 | 17.5 |
| 25.2 | 54.3 |
| 25.5 | 49.2 |
| 26.0 | 23.0 |
| 26.9 | 30.6 |
| 27.1 | 51.8 |
| 27.6 | 13.4 |
| 28.4 | 20.2 |
| 28.5 | 21.4 |
| 28.7 | 21.1 |
| 28.9 | 20.0 |
| 29.4 | 13.3 |
| 32.7 | 17.4 |
| 33.4 | 27.7 |
| 36.4 | 13.6 |
| 37.3 | 13.5 |
| 37.8 | 13.9 |

TABLE 1-continued

Main PXRD Peaks for 4-fluoro-alpha-[2-methyl-1-oxopropyl]-gamma-oxo-N, beta-diphenylbenzenebutanamide

| Angle 2-Theta (°) | Relative Intensity (%) |
|---|---|
| 38.6 | 20.3 |
| 39.4 | 13.6 |
| 39.8 | 13.9 |

TABLE 2

FT-IR Peaks for 4-fluoro-alpha-[2-methyl-1-oxopropyl]-gamma-oxo-N, beta-diphenylbenzenebutanamide Wavenumber (cm$^{-1}$)

3290w*
3083w
3025w
2969w
2927w
2871w
1720m
1683m
1649s
1594m
1546m
1506w
<u>1492m</u>
1466w
1448m
1407w
1381m
<u>1327m</u>
1279m
1227m
1207m
1174w
1151m
1099w
1037w
1012w
992w
875w
<u>843m</u>
809w
754s
736w
<u>696s</u>
683w

Experimental error is ±2 cm$^{-1}$ (w: weak, m: medium, s: strong)

TABLE 3

FT-Raman Peaks for 4-fluoro-alpha-[2-methyl-1-oxopropyl]-gamma-oxo-N, beta-diphenylbenzenebutanamide Wavenumber (cm$^{-1}$)

3301w*
3084s
3069s
3060m
3042w
2975w
2938w
2918w
2871w
1722w
1684s
1652w
<u>1601s</u>
1546w
1449w
1352w
1330w

TABLE 3-continued

FT-Raman Peaks for 4-fluoro-alpha-[2-methyl-1-oxopropyl]-gamma-oxo-N, beta-diphenylbenzenebutanamide Wavenumber (cm$^{-1}$)

1310w
1281w
1245w
1229w
1210w
1176m
1159w
1154w
1033w
<u>1004s</u>
911w
877w
843w
813w
633w
619w
307w
290w
234w
186w
158m
<u>115vs</u>
<u>87vs</u>
70vs

Experimental error is ±2 cm$^{-1}$. (w: weak, m: medium, s: strong, vs: very strong)

Figure 5:
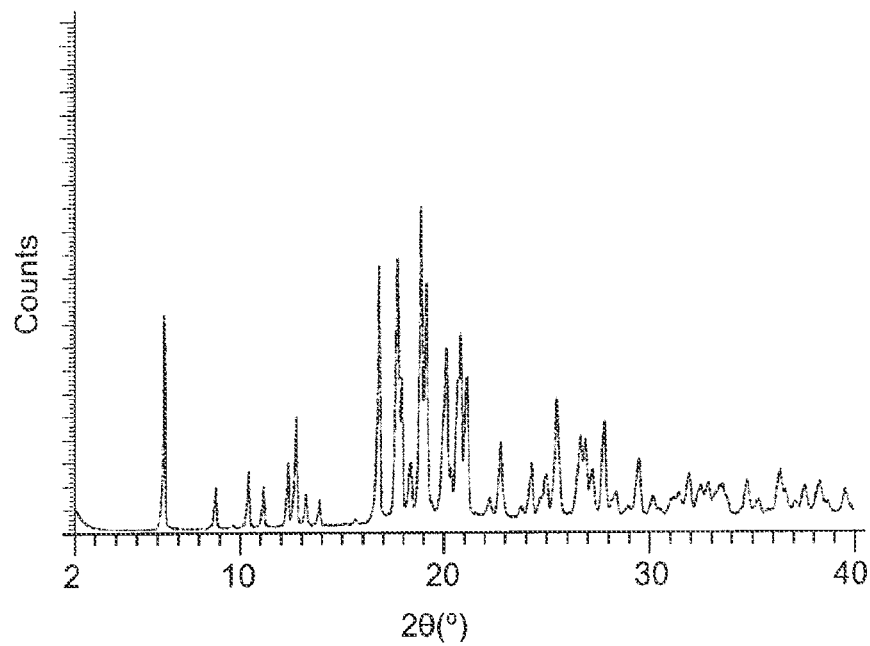
FIG. 5 is an experimental powder X-ray diffraction pattern for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide. The scale of the abscissa is degrees two-theta. The ordinate is the intensity of the counts.
Figure 6:
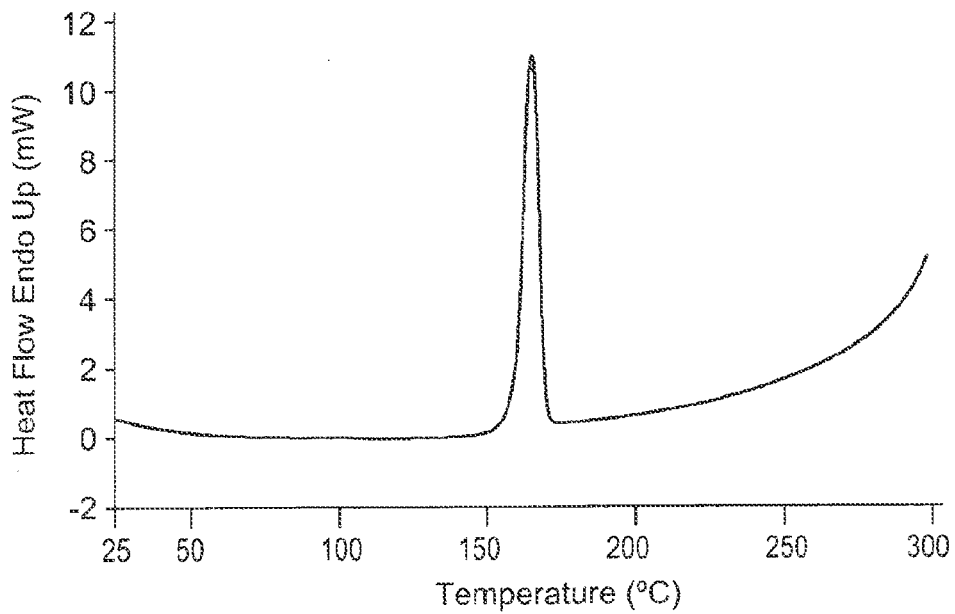
FIG. 6 is the differential scanning calorimetry (DSC) thermogram for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.
Figure 7A:
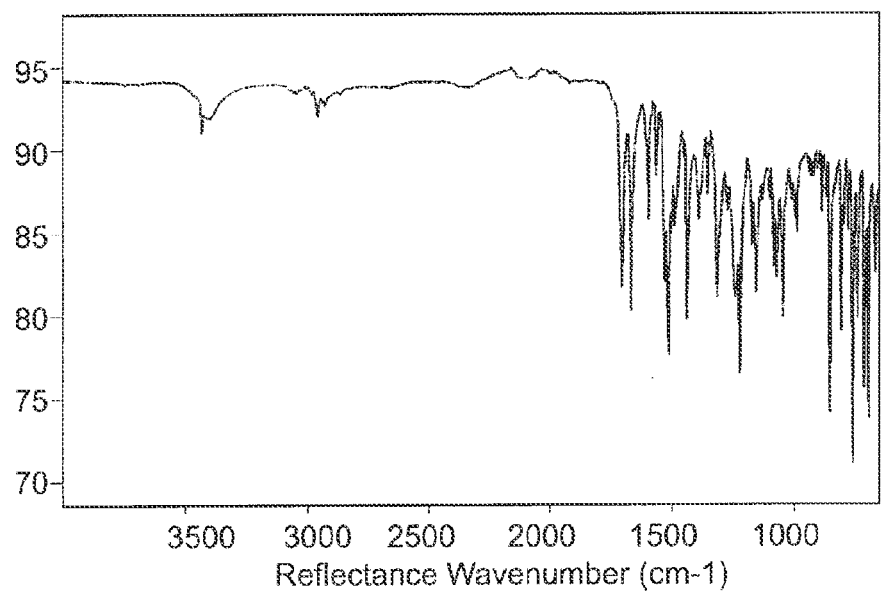
FIG. 7A is the infrared (FTIR) spectrum for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide showing reflectance wavenumbers from 3500 to 1000 cm$^{-1}$.
Figure 7B:
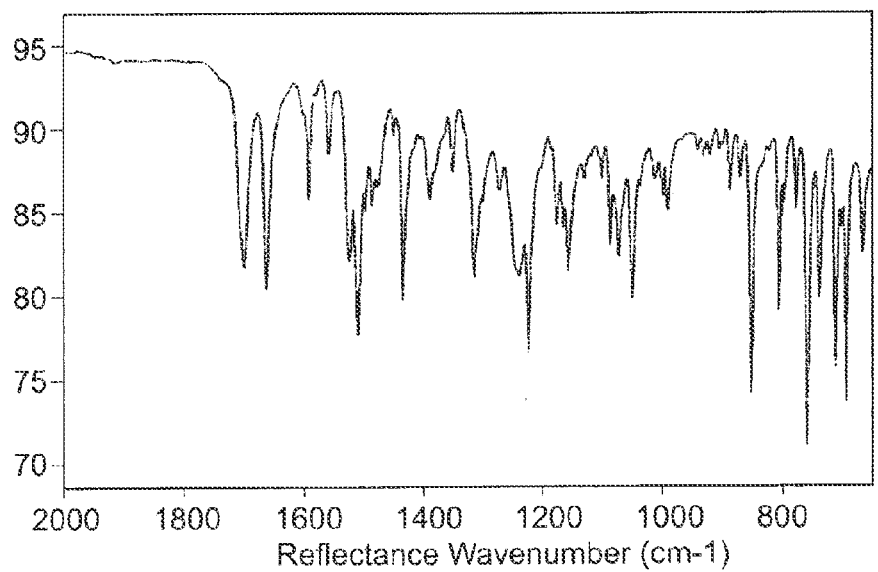
FIG. 7B is the infrared (FTIR) spectrum for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide showing reflectance wavenumbers from 2000 to 800 cm$^{-1}$.
Figure 8A:
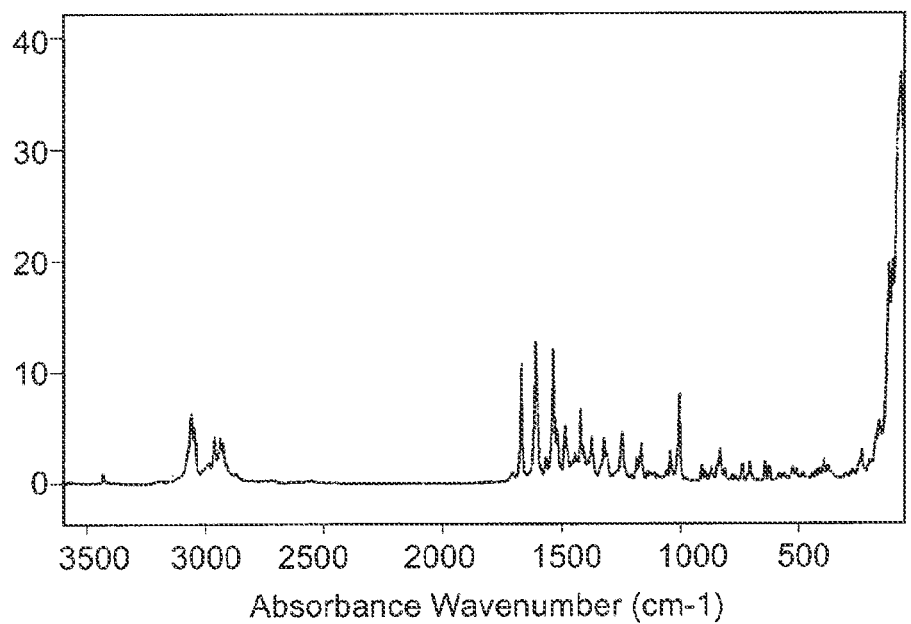
FIG. 8A is the Raman spectrum for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide showing absorbance wavenumbers from 3500 to 500 cm$^{-1}$.
Figure 8B:
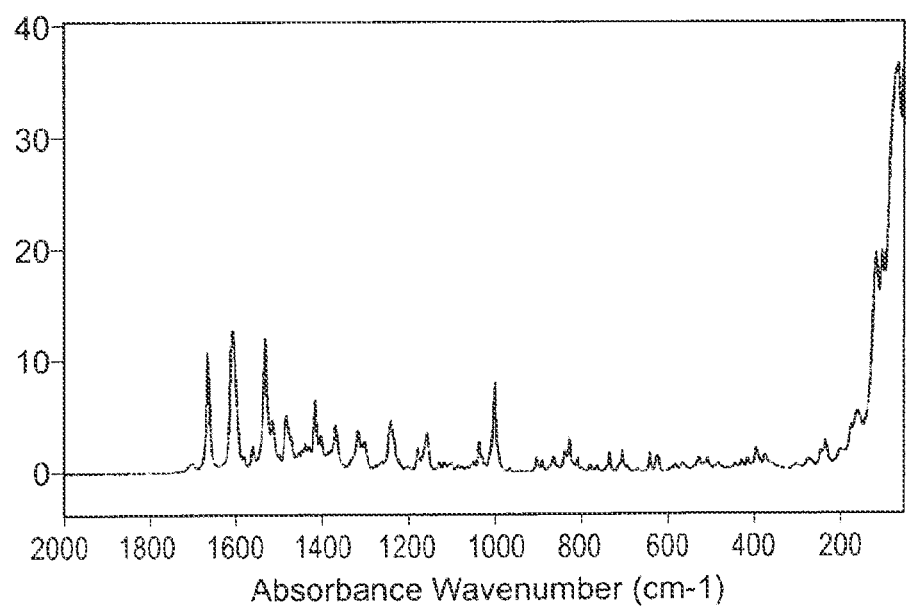
FIG. 8B is the Raman spectrum for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide showing absorbance wavenumbers from 2000 to 200 cm$^{-1}$.

The PXRD pattern for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is shown in FIG. 5. The main peaks (greater than 12% relative intensity) are given in Table 4. (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide displays characteristic diffraction peaks at 6.3, 12.7, 16.8, 21.1 and 25.5 degrees two theta±0.1 degree. The DSC thermogram is shown in FIG. 6. (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide shows a sharp endothermic peak at 166° C.±2° C. The FT-IR spectrum is illustrated in FIG. 7. The FT-IR peak table is given in Table 5. (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide displays characteristic peaks at 851, 1220, 1047, 757, 1153 cm$^{-1}$ (in this order). The FT-Raman spectrum is illustrated in FIG. 8. The FT-Raman peak table is given in Table 6 (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide displays characteristic peaks at 1531, 997, 114, 99, 1605 cm$^{-1}$.

TABLE 4

Main PXRD Peaks for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide

| Angle 2-Theta (°) | Relative Intensity (%) |
|---|---|
| 6.3 | 66.9 |
| 8.8 | 13.7 |
| 10.4 | 18.7 |
| 11.1 | 14.1 |
| 12.3 | 21.4 |
| 12.7 | 35.5 |

TABLE 4-continued

Main PXRD Peaks for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide

| Angle 2-Theta (°) | Relative Intensity (%) |
|---|---|
| 16.8 | 82.0 |
| 17.7 | 84.3 |
| 17.9 | 47.4 |
| 18.3 | 21.3 |
| 18.9 | 100.0 |
| 19.1 | 76.5 |
| 20.0 | 35.2 |
| 20.1 | 56.7 |
| 20.3 | 19.8 |
| 20.7 | 47.6 |
| 20.8 | 61.6 |
| 21.1 | 48.0 |
| 22.8 | 27.7 |
| 24.3 | 21.0 |
| 25.0 | 17.8 |
| 25.5 | 41.3 |
| 26.7 | 29.7 |
| 26.9 | 28.4 |
| 27.2 | 19.3 |
| 27.8 | 33.9 |
| 28.4 | 12.5 |
| 29.5 | 22.7 |
| 31.4 | 12.2 |
| 31.9 | 17.9 |
| 32.5 | 14.3 |
| 32.8 | 15.1 |
| 33.5 | 14.2 |
| 34.7 | 15.8 |
| 36.3 | 18.1 |
| 36.6 | 13.2 |
| 37.5 | 14.1 |
| 38.3 | 15.6 |
| 39.5 | 13.2 |

TABLE 5

FT-IR Peaks for (2R-trans)-5-(4-fluorophenyl)-2(1-methylethyl)--N,4-diphenyl-1-[2-(tetrahydro-4-hydroxy-6-oxo-2H-pyran-2-yl)ethyl]-1H-pyrrole-3-carboxamide Wavenumber (cm$^{-1}$)

| | | | |
|---|---|---|---|
| 3431w* | 1497w | 1161w | 851s |
| 2961w | 1485m | 1153m | 804m |
| 2937w | 1433s | 1097w | 795w |
| 2927w | 1387m | 1083m | 775w |
| 1699s | 1349w | 1069m | 75Th |
| 1662s | 1312m | 1047m | 736m |
| 1591m | 1269w | 996w | 710s |
| 1559w | 1235m | 988w | 691s |
| 1524m | 1220s | 885w | 664m |
| 1509s | 1172m | 869w | |

Experimental error is ± 2 cm$^{-1}$.
(w: weak, m: medium, s: strong)

TABLE 6

FT-Raman Peaks for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide Wavenumber (cm$^{-1}$)

| | | | |
|---|---|---|---|
| 3433w* | 1531s | 997m | 411w |
| 3064m | 1514m | 902w | 391w |
| 3049m | 1482m | 861w | 371w |
| 2984w | 1414m | 836w | 231w |

TABLE 6-continued

FT-Raman Peaks for (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide Wavenumber (cm$^{-1}$)

| | | | |
|---|---|---|---|
| 2963w | 1401w | 824w | 198w |
| 2940w | 1368w | 805w | 172w |
| 2929w | 1315w | 731w | 157m |
| 2908w | 1301w | 701w | 114vs |
| 1701w | 1239m | 638w | 99vs |
| 1664s | 1178w | 618w | 67vs |
| 1605s | 1155w | 524w | 61vs |
| 1559w | 1036w | 504w | |

Experimental error is ± 2 cm$^{-1}$.
(w: weak, m: medium, s: strong, vs: very strong)

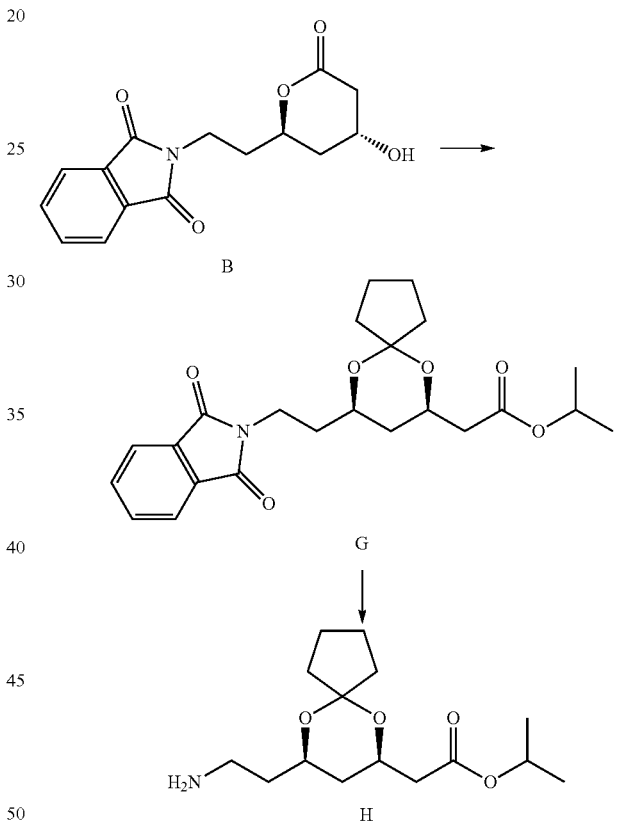

Scheme 2

As set forth in Scheme 2, the cyclopentylidene phthalimido isopropyl ester (G) may be prepared by reacting 2-[2-(4-hydroxy-6-oxo-tetrahydro-pyran-2-yl]-isoindole-1,3-dione (B) with cyclopentanone and isopropyl alcohol in the presence of magnesium sulfate and methanesulfonic acid (MSA). The reaction mixture is stirred at room temperature at a pH between about 1 to about 2, preferably about 1.5, for a time period between about 20 hours to about 28 hours, preferably about 24 hours.

The cyclopentylidene phthalimido isopropyl ester (G) is deprotected to give the corresponding amino cyclopentylidene isopropyl ester (H) by treating (G) with a base, such as primary amine, i.e. an alkylamine, diamine such as ethylene diamine or an hydroxyamine, in the presence of a polar protic solvent, such as methanol. The reaction mixture is stirred at room temperature for a time period between about 30 minutes to about 4 hours, preferably about 2 hours.

The amino cyclopentylidene isopropyl ester (H) so formed can be further reacted with 4-fluoro-alpha-[2-methyl-1-oxo-propyl]-gamma-oxo-N, beta-diphenylbenzenebutanamide of formula II

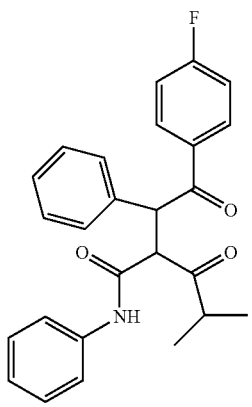

to give the corresponding pyrrole ring containing cyclopentylidene isopropyl ester of formula IV below

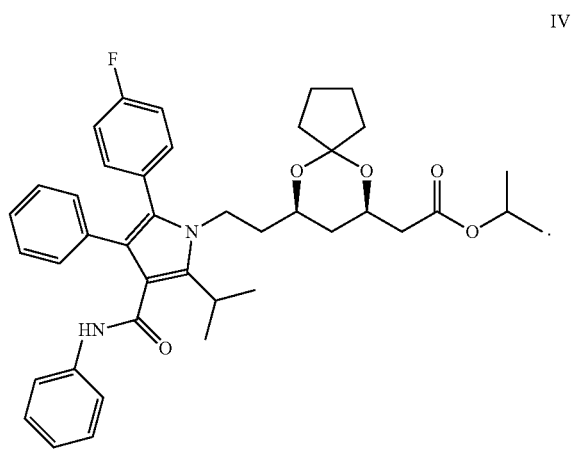 [SMILES: CC(C)OC(=O)C[C@H]1C[C@@H](CCn2c(-c3ccc(F)cc3)c(-c3ccccc3)c(C(=O)Nc3ccccc3)c2C(C)C)OC2(CCCC2)O1]

Scheme 3 describes in general a process encompassed by the present invention. As set forth in Scheme 3, a DERA aldolase catalyzes two sequential aldol condensation reactions between an N-protected aminopropionaldehyde substrate (i.e. R1=protecting group) selected from the group consisting of N-formyl-3-aminopropionaldehyde, 3-succinimido-propionaldehyde, N-diBoc-3-aminopropionaldehyde, N-Boc-3-aminopropionaldehyde, aminoacetaldehyde, N—CBz-3-aminopropionaldehyde, N-acetyl-3-aminopropionaldehyde, N-Fmoc-3-aminopropionaldehyde or N-Fmoc-aminoacetaldehyde, and 2 mol of acetaldehyde in the presence of a suitable co-solvent such as methyl tert-butyl ether (MTBE) and water to yield the protected desired amino-lactol (I). Suitable DERA aldolases include, but are not limited to, DERA 04, DERA 06, DERA 101, DERA 102, DERA 104, DERA 105, DERA 106, DERA107 and DERA 108, preferably DERA 04 and DERA 102. The acetaldehyde is added to a mixture of the N-protected aminoaldehyde and DERA aldolase over a time period between about 7 hours to about 12 hours, preferably about 10 hours. The mixture so formed is further stirred at a temperature between about 15° C. to about 30° C., preferably about 22° C., for a time period between about 20 hours to about 60 hours, preferably about 48 hours.

The amino-lactol (I) can undergo catalytic (e.g. Pt/C, Pd/C) dehydrogenation to form carboxylic acid (K), which can then undergo lactonization to form (J).

Any catalytic dehydrogenation means known in the art to convert (I) to (K) are encompassed by the present invention. Examples of suitable catalysts include, but are not limited to, Pt/C, Pd/C, Pt/Bi/C, Pd/Bi/C and any other dehydrogenation catalysts. In one embodiment of the invention, the catalytic dehydrogenation is performed at about pH 7 to about pH 10 using air or oxygen as terminal oxidant.

Any lactonization means known in the art to convert carboxylic acid (K) to lactone (J) are encompassed by the present invention including, but not limited to, the use of acid catalysts such as, but not limited to, hydrochloric acid, sulfuric acid, methanesulfonic acid (MSA), p-toluenesulfonic acid (TSA) and any other lactonization acids known in the art.

Alternatively, oxidation of the lactol (I) to lactone (J) or carboxylic acid (K) can be performed by use of any oxidation means known in the art that will achieve the desired transformation.

Scheme 3

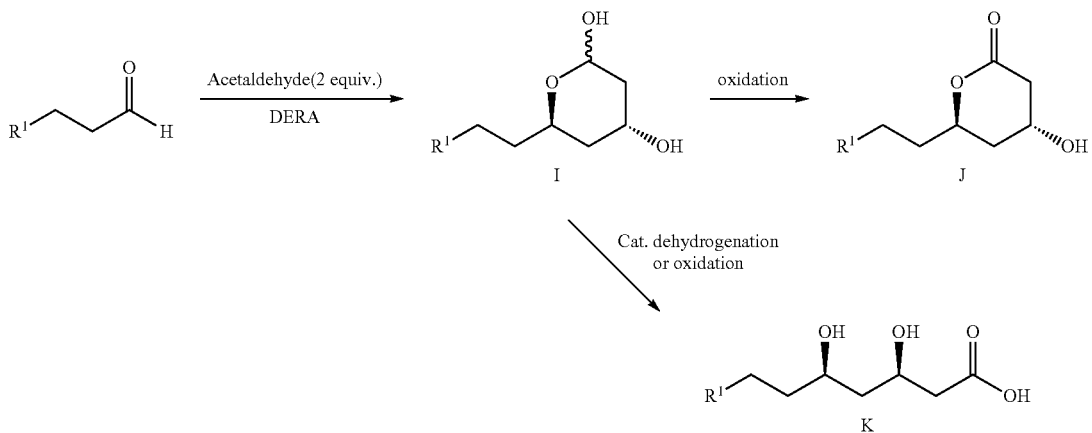

Scheme 4

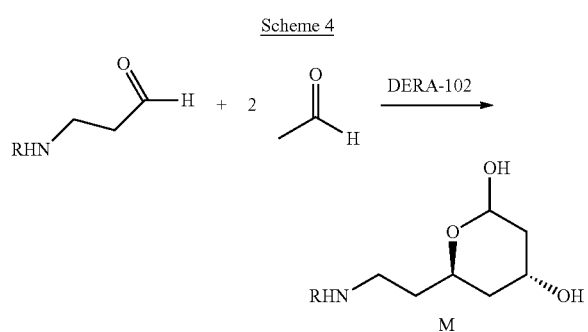

R = H, CBz, Boc, Fmoc, benzyl, or dibenzyl

As set forth in Scheme 4, a DERA aldolase catalyzes an aldol condensation reaction between an aminoaldehyde or an N-protected aminoaldehyde and 2 mol of acetaldehyde to give the desired amino-lactol (M).

The following non-limiting examples illustrate the invention.

Example 1

2-[2-(4,6-Dihydroxy-tetrahydro-pyran-2-yl]-isoindole-1,3-dione

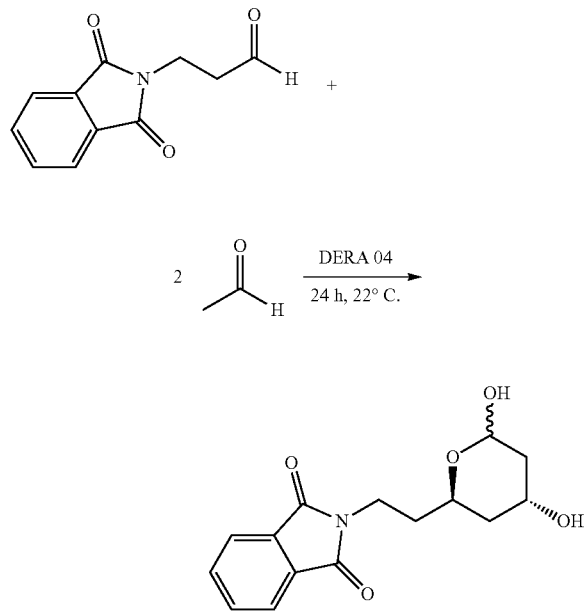

To a suspension of 3-phthalimido-propionaldehyde (10.0 grams, 49.2 mmol) in 20 mL of tert-butyl methyl ether (MTBE) was added a solution of DERA 04 lysate (52.0 mL, 10,400 units, prepared from 13.0 grams of wet cells of DERA 04 in phosphate buffer, pH 7.0, 0.01 M) and phosphate buffer (102 mL, pH 7.0, 0.01 M) with vigorous stirring at 22° C. Acetaldehyde (4.8 grams, 108.2 mmol, Aldrich) dissolved in water (10 mL) was continuously added into the reaction mixture by a programmed pump for 10 hours. The pH of the reaction mixture was kept 7.0 by titration with 1.0 N sodium hydroxide. The reaction mixture was further stirred at 22° C. for 10 hours and the conversion was monitored by high pressure liquid chromatography (HPLC). After 20 hours, about 95% of the starting material was consumed and 50-55% of the desired lactol was produced based on high pressure liquid chromatography analysis, and the resulting reaction mixture was used directly in the subsequent oxidation step. LC-ESIMS of lactol: m/z [M+H]$^+$ 292.3.

Example 2

2-[2-(4-Hydroxy-6-oxo-tetrahydro-pyran-2-yl]-isoindole-1,3-dione

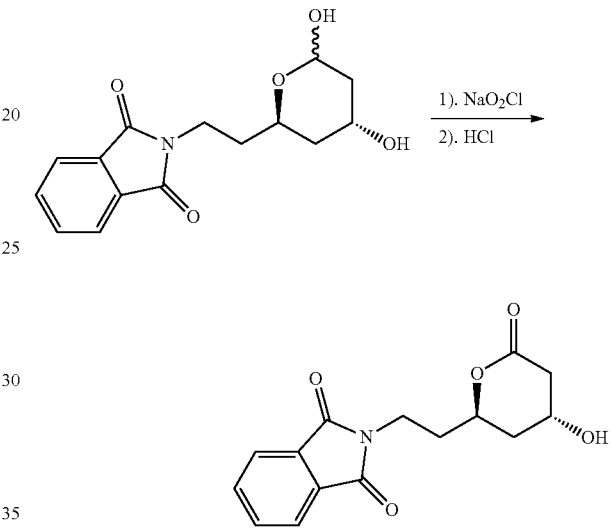

To a suspension of crude lactol (200 mL; prepared according to Example 1) was added dimethyl sulfoxide (10 mL) with stirring. Then a solution of sodium chlorite (1.5 eq., 8.3 grams, Aldrich) in water (18 mL) was added dropwise over 30 minutes. The temperature was controlled in the range of 20-25° C. The pH of the reaction mixture should be kept above 4.0. After 4 hours, acetone (200 mL) was added. The reaction mixture was stirred at 0-5° C. for 1 hour and then filtered through a celite pad (10 grams) in a buchel funnel. The filtered cake was washed with acetone (50 mL twice). The combined acetone filtrate was concentrated to remove acetone and tert-butyl methyl ether (MTBE) under vacuum. The remaining aqueous solution was adjusted to pH of approximately 4.0 and extracted with ethyl acetate (100 mL three times). The combined ethyl acetate solution was dried over magnesium sulfate and concentrated to about 100 mL in vacuum, which was treated with dry hydrochloric acid (0.6 mL, 4M in dioxane) in presence of magnesium sulfate (2 grams) and stirred at room temperature for 4 hours. Then the reaction mixture was washed with saturated sodium bicarbonate/brine and dried over sodium sulfate. The solution of ethyl acetate was concentrated to 50 mL to which was then added 50 mL of heptane. The formed solid was filtered and washed with heptane (20 mL), and dried in oven to afford lactone as a white solid (40%-45% for three steps, 95% chemical purity, ee>99%, de>86%). LC-ESIMS [M+Na]$^+$ m/z 312.0. $^1$H NMR (CDCl$_3$, 400 MHz): δ 7.82 (m, 2H), 7.68 (m, 2H), 4.78 (m, 1H), 4.41 (m, 1H), 3.84 (m, 2H), 2.65 (m, 2H), 1.94-2.14 (m, 3H), 1.81 (m, 1H). $^{13}$C NMR (CDCl$_3$, 100

MHz) δ 170.15, 168.61 (2), 134.32 (2), 132.20 (2), 123.58 (2), 73.82 (2), 62.85, 38.63, 35.70, 34.47, 34.40.

Example 3

2-[2-(4,6-Dihydroxy-tetrahydro-pyran-2-yl]-isoindole-1,3-dione

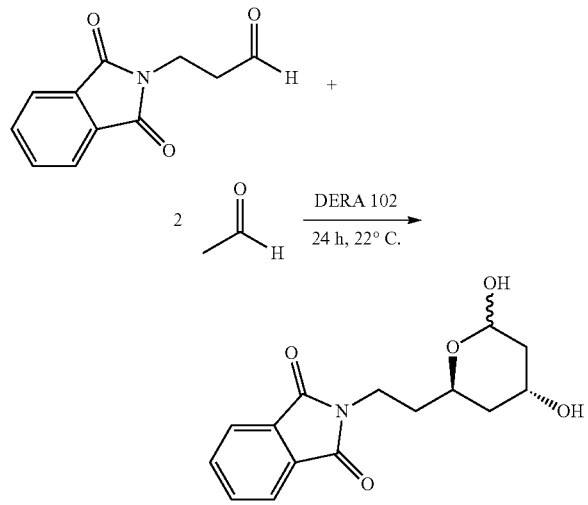

To a suspension of *E. coli* cells containing DERA 102 (4 grams wet cells suspended in 190 mL of phosphate buffer, pH 7.0, 0.01 M) was added a mixture of 3-phthalimido-propionaldehyde (2.0 grams, 9.8 mmol) and acetaldehyde (0.96 grams, 21.8 mmol, Aldrich) in dimethyl sulfoxide (15 mL) by a programmed pump over 10 hours. The reaction mixture was further stirred at 22° C. for 14 hours. The progress of the reaction was monitored by high pressure liquid chromatography (HPLC). After 24 hours, the reaction mixture was extracted with ethyl acetate (100 mL twice). After the separation of two layers by centrifugation, the organic layer was dried and evaporated to give the crude lactol (1.6 grams, 45-50%) as a solid, which was directly submitted to next oxidation step. LC-ESIMS of lactol: m/z [M+H]$^+$ 292.3.

Example 4

7-(1,3-Dioxo-1,3-dihydro-isoindo-2-yl)-3,5-dihydroxy-heptanoic acid

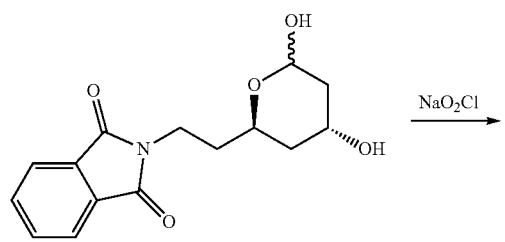

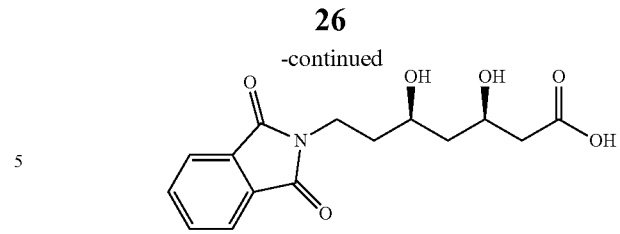

To a mixture of crude lactol (1.6 grams; prepared according to Example 3) in isopropanol (4.8 mL) and dimethyl sulfoxide (1.0 mL) and 26 mL of phosphate buffer (pH 6.0, 0.01 M) was added a solution of sodium chlorite (0.9 grams, Aldrich) in water (2 mL) at room temperature. The pH of the reaction mixture was kept between 5.0 and 6.0. After 4 hours, the reaction mixture was neutralized to pH 7.0 with 1 N sodium hydroxide and extracted with ethyl acetate (30 mL). After removal of the organic layer, the aqueous layer was acidified to pH 4.0 with 1 N hydrochloric acid and extracted with ethyl acetate (30 mL three times). The combined organic layer containing crude acid was treated with dicyclohexylamine (1.5 mL) to afford the corresponding dicyclohexylamine salt (1.5 grams, approximately 90% purity) at cold temperature (5-10° C.). LC-ESIMS m/z [M+Na]$^+$ 330.0. $^1$H NMR (CDCl$_3$, 400 MHz): δ 7.59 (m, 4H), 3.88 (m, 1H), 3.58 (m, 1H), 3.56 (m, 2H), 3.03 (m, 2H), 2.07-2.19 (m, 2H), 1.40-1.82 (m, 14H), 0.80-1.20 (m, 10H). $^{13}$C NMR (CDCl$_3$, 100 MHz) δ 180.22, 170.82, 134.65 (2), 131.52 (2), 123.32 (2), 67.36, 67.31, 53.23 (2), 44.87, 43.14, 34.82, 34.57, 29.14 (4), 24.64 (2), 24.04 (4).

Example 5

2-[2-(4-Hydroxy-6-oxo-tetrahydro-pyran-2-yl]-isoondole-1,3-dione

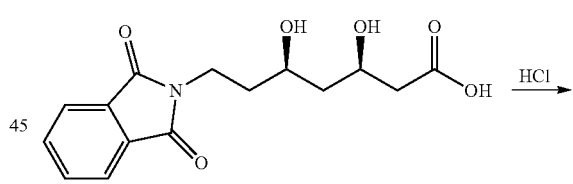

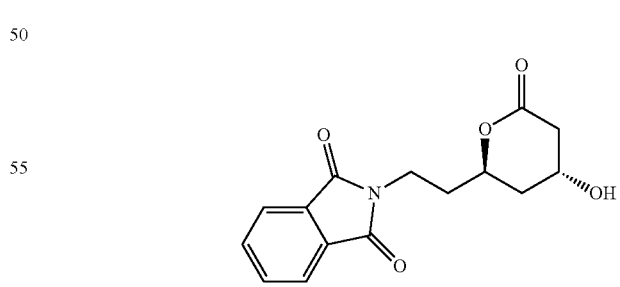

The crude acid (1.0 grams, prepared according to Example 4) in ethyl acetate (20 mL) was treated with anhydrous hydrocholic acid in dioxane (4 M, 50 μL) and the reaction mixture was stirred at room temperature for 2-3 hours. The reaction mixture was washed with water (pH 7.0, 50 mL twice). The organic layer was dried over Na$_2$SO$_4$ and evaporated to give the desired lactone as a white solid (0.94 grams, approximately 94% chemical purity, >99% ee, >93% de).

Example 6

Phthalimido Acetonide Isopropyl Ester

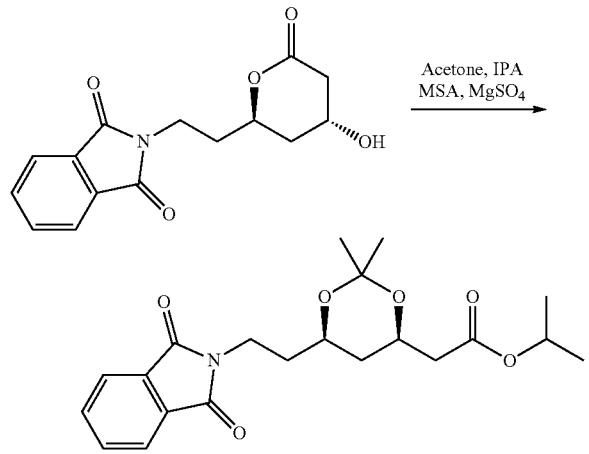

Phthalimido lactone (5.0 grams, 17.3 mmol) was suspended in toluene (100 mL). IPA (6.6 mL, 86.0 mmol, 5 eq.), acetone (6.3 mL, 86.0 mmol, 5 eq.), magnesium sulfate (5.0 grams) and methanesulfonic acid (0.4 mL, 6.0 mmol, 0.35 eq.) were added. pH=1.5 (required <2). The mixture was stirred at room temperature for 24 hours. The reaction was quenched with triethylamine (0.9 mL, 6.5 mmol) and the mixture was filtered through a grade 4 sinter funnel, washing with toluene (20 mL). The filtrate was washed with sat. aq. NaHCO$_3$ (20 mL), dried over magnesium sulfate, filtered and concentrated in vacuo to give a colourless oil, 6.88 grams, 100%.

Example 7

Amino Acetonide Isopropyl Ester

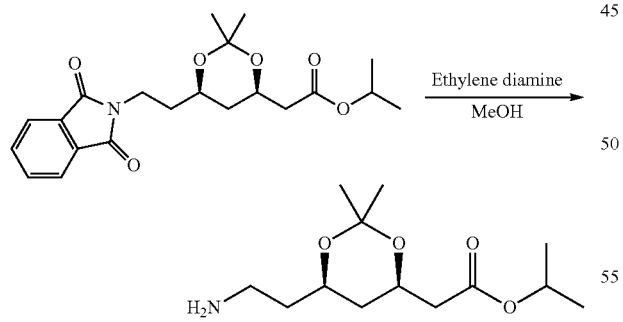

Phthalimido acetonide isopropyl ester (6.55 g, 16.8 mmol) was dissolved in methanol (65 mL, 10 volumes). Ethylene diamine (10.1 grams, 168 mmol, 10 eq.) was added dropwise and the solution was stirred at room temperature.

HPLC analysis after 1 hour indicated no starting material. After 2 hours the reaction mixture was concentrated in vacuo on a rotavap. The residue was partitioned between toluene (65 mL, 10 volumes) and water (65 mL, 10 volumes)—agitated for 15 minutes then allowed to stand for 15 minutes. The cloudy aqueous phase was re-extracted with toluene (65 mL)—agitated for 15 minutes then allowed to stand for 15 minutes. The combined toluene extracts were washed with water (65 mL)—agitated for 15 minutes then allowed to stand for 15 minutes. The toluene extracts were concentrated in vacuo to give an oil product, 2.85 grams, 65.0% yield.

Example 8

Pyrrolyl Acetonide Isopropyl Ester (AIE)

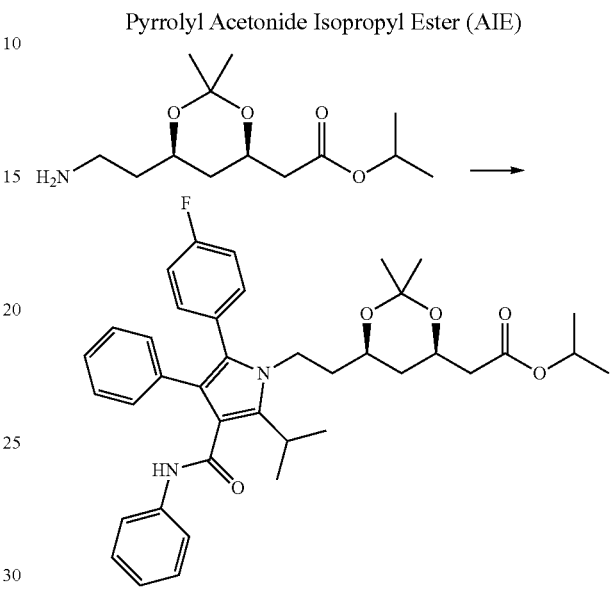

4-fluoro-alpha-[2-methyl-1-oxopropyl]-gamma-oxo-N, beta-diphenylbenzenebutanamide (4.64 grams, 11.1 mmol, 1.03 eq.) was weighed into a one-neck 50 mL rbf. Amino acetonide isopropyl ester (2.80 grams, 10.8 mmol) in tert-butyl methyl ether (MTBE; 11 mL) was added followed by a tetrahydrofuran flush (4.2 mL). Triethylamine (1.09 grams, 10.8 mmol, 1 eq.) was added and the slurry was heated to 50° C. Pivalic acid (1.10 grams, 10.8 mmol, 1 eq.) was added and the mixture was heated at reflux (67-68° C.) for 88 hours. On cooling, the volatiles were removed in vacuo and the residue was taken up in isopropyl alcohol (IPA; 17.5 mL) and heated to 80° C. Further IPA (10 mL) was required to give a clear solution. The solution was allowed to cool to room temperature—no crystallisation occurred. The solution was seeded with authentic product and crystallisation occurred. The slurry was cooled to 0° C. and held for 30 minutes. The product was collected on a grade 2 sinter funnel and washed with isopropyl alcohol (i.e, IPA; 3 times with 10 mL). The product was dried in a vacuum oven at 40-50° C. for 18 hours to give a pale yellow solid (4.15 grams, 60.0% yield).

Example 9

Cyclopentylidene-Phthalimido-Isopropyl Ester

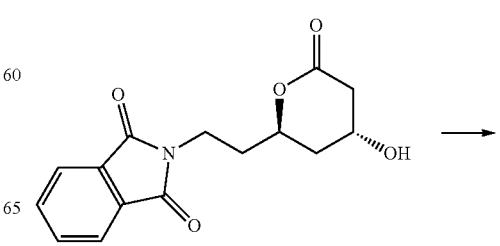

-continued

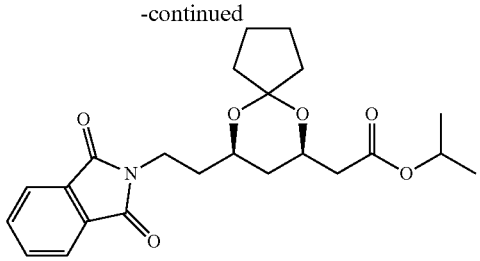

Phthalimido lactone (5.0 grams, 17.3 mmol) was suspended in toluene (50 mL). IPA (6.6 mL, 86.0 mmol, 5 eq.), cyclopentanone (3.0 grams, 34.8 mmol, 2 eq.), magnesium sulfate (5.0 grams) and methanesulfonic acid (0.4 mL, 6.0 mmol, 0.35 eq.) were added. pH of 1.5 (less than pH of 2 required). The mixture was stirred at room temperature for 24 hours. The reaction was quenched with triethylamine (0.9 mL, 6.5 mmol) and the mixture was filtered through a grade 4 sinter funnel, washing with toluene (20 mL). The filtrate was washed with sat. aq. NaHCO$_3$ (20 mL), dried over magnesium sulfate, filtered and concentrated in vacuo to give a colourless oil, 7.18 grams, 100%.

Example 10

Amino Cyclopentylidene Isopropyl Ester

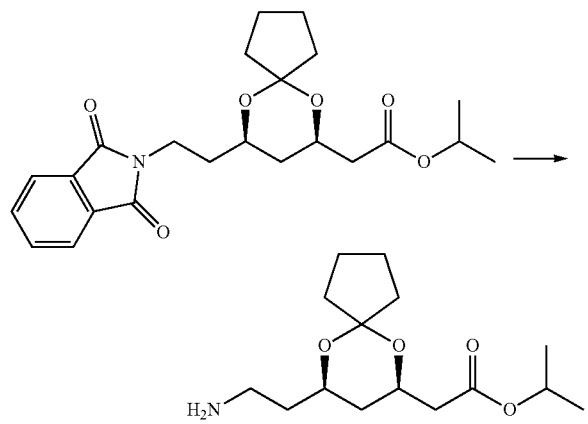

Cyclopentylidene phthalimido isopropyl ester (10.0 grams, 24.1 mmol) was dissolved in methanol (50 mL, 5 volumes). Ethylene diamine (2.9 grams, 48.2 mmol, 2 eq.) was added dropwise and the solution was stirred at room temperature.

High pressure liquid chromatography (HPLC) analysis after 1 hour indicated no starting material. After 2 hours the reaction mixture was concentrated in vacuo on a rotavap. The residue was partitioned between toluene (100 mL, 10 volumes) and water (100 mL, 10 volumes)—agitated for 15 minutes then allowed to stand for 15 minutes. The cloudy aqueous phase was re-extracted with toluene (65 mL)—agitated for 15 minutes then allowed to stand for 15 minutes. The combined toluene extracts were washed with water (65 mL)—agitated for 15 minutes then allowed to stand for 15 minutes. The toluene extracts were concentrated in vacuo to give the product as an oil, 6.45 grams, 94.0% yield. It is important to ensure absence of ethylenediamine from the crude product as it leads to the formation of an impurity (bispyrrole) in the subsequent Paal-Knorr reaction.

Example 11

Pyrrolyl Cyclopentylidene Isopropyl Ester (CIE)

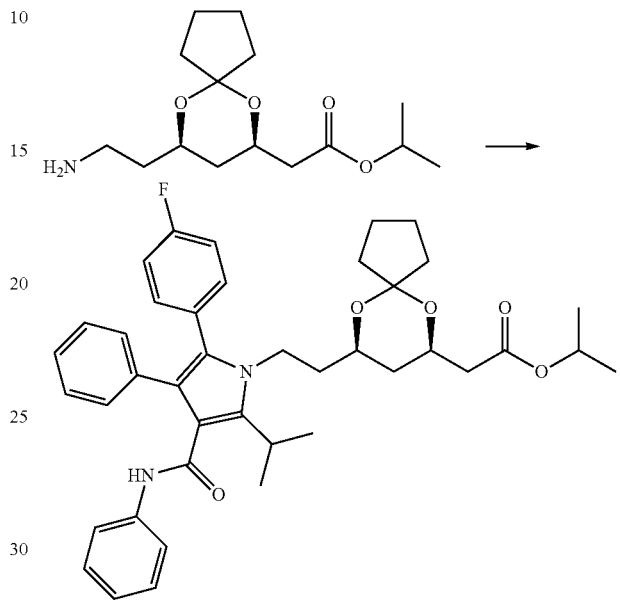

4-fluoro-alpha-[2-methyl-1-oxopropyl]-gamma-oxo-N,beta-diphenylbenzenebutanamide (4.64 grams, 11.1 mmol, 1.03 eq.) was weighed into a one-neck 50 mL rbf. Amino cyclopentylidene isopropyl ester (3.08 grams, 10.8 mmol) in MTBE (11 mL) was added followed by a tetrahydrofuran flush (4.2 mL). Triethylamine (1.09 grams, 10.8 mmol, 1 eq.) was added and the slurry was heated to 50° C. Pivalic acid (1.10 grams, 10.8 mmol, 1 eq.) was added and the mixture was heated at reflux (67-68° C.) for 88 hours. On cooling, the volatiles were removed in vacuo and the residue was taken up in isopropyl alcohol (17.5 mL) and heated to 80° C. Further isopropyl alcohol (10 mL) was required to give a clear solution. The solution was seeded with authentic product and crystallisation occurred. The slurry was cooled to 0° C. and held for 30 minutes. The product was collected on a grade 2 sinter funnel and washed with isopropyl alcohol (3 times 10 mL). The product was dried in a vacuum oven at 40-50° C. for 18 hours to give a pale yellow solid (4.31 grams, 60.0% yield). Purity by high pressure liquid chromatography was greater than 99% pure.

Example 12

4-fluoro-alpha-[2-methyl-1-oxopropyl]-gamma-oxo-N,beta-diphenylbenzene butanamide A reaction vessel is inerted using at least 4 cycles of vacuum, releasing the vacuum each time with nitrogen. 250 liters of tetrahydrofuran is charged to the reaction vessel via spray nozzles. Spray ball nozzles ensure that all areas of the reaction vessel are penetrated in particular the top inner surface of the vessel and the agitator device also present inside the reaction vessel. The tetrahydrofuran washings are drained off and collected for waste recycling.

When the reaction vessel is dry 480 kgs 2-benzylidine isobutyrylacetamide (BIBEA), 60 kgs ethyl hydroxyethylmethyl thiazolium bromide (MTB or ethyl hydroyethyl MTB), 200 liters, 216 kgs of 4-fluorobenzaldehyde and 120 kgs of triethylamine are charged to the reaction vessel and heated with agitation to between 60 and 70° C. The reaction mixture is aged for 16 to 24 hours maintaining the temperature at 65+/−5° C. The contents re then cooled to 60+/−5° C. for 54 to 66 minutes. 600 liters of isopropanol is charged to the reaction mixture and the mixture is heated to about 100° C. to achieve a solution.

600 liters of deionised water is charged to the reaction vessel over 30 minutes while maintaining the temperature at 60+/−5° C. The batch is aged for 54 to 66 minutes and the contents cooled to between 25+/−5° C. over a 2 to 4 hour period at a rate of 15/20° C. per hour. The batch is aged at this temperature for at least 1 hour and the contents cooled further to 0+/−5° C. and aged for at least 1 hour.

The batch is isolated on a filter and washed with isopropanol. The product is dried under vacuum at 50+/−5° C. to a water content of less than 0.5%. The contents are then cool to approximately less than 30° C. before discharging.

Example 13

PXRD of 4-fluoro-alpha-[2-methyl-1-oxopropyl]-gamma-oxo-N, beta-diphenylbenzene butanamide The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha$_1$ X-rays (wavelength=1.5406 Angstroms) with the X-ray tube operated at 40 kV/30 mA. The analyses were performed with the goniometer running in continuous mode set for a 0.2 second count per 0.018° step over a two theta range of 2° to 55°. Peaks were selected using Bruker-AXS Ltd. Evaluation software with a threshold of 1 and a peak width of 0.3° 2-theta. The data were collected at 21° C.

As will be appreciated by the skilled person, the relative intensities of the various peaks within Table 1 given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Table.

Example 14

DSC of 4-fluoro-alpha-[2-methyl-1-oxopropyl]-gamma-oxo-N, beta-diphenylbenzene butanamide 3.117 mg of 4-fluoro-alpha-[2-methyl-1-oxopropyl]-gamma-oxo-N, beta-diphenylbenzene butanamide was heated from 10 to 250° C. at 20° C. per minute using a Perkin Elmer Diamond DSC with autosampler and a 4 hole side wall vented aluminium pan and lid with nitrogen flow gas.

Example 15

FT-IR of 4-fluoro-alpha-[2-methyl-1-oxopropyl]-gamma-oxo-N, beta-diphenylbenzene butanamide The IR spectrum was acquired using a ThermoNicolet Nexus FTIR spectrometer equipped with a 'DurasampIIR' single reflection ATR accessory (diamond surface on zinc selenide substrate) and d-TGS KBr detector. The spectrum was collected at 2 cm$^{-1}$ resolution and a co-addition of 256 scans. Happ-Genzel apodization was used. Because the FT-IR spectrum was recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$. Peaks were picked using ThermoNicolet Omnic 6.0a software. Intensity assignments are relative to the major band in the spectrum, so are not based on absolute values measured from the baseline.

Example 16

FT-Raman IR of 4-fluoro-alpha-[2-methyl-1-oxopropyl]-gamma-oxo-N, beta-diphenylbenzene butanamide The Raman spectrum was collected using a Bruker Vertex70 with RamII module FT-Raman spectrometer equipped with a 1064 nm NdYAG laser and LN-Germanium detector. All spectra were recorded using 2 cm$^{-1}$ resolution and Blackman-Harris 4-term apodization. The spectrum was collected using laser power of 300 mW and 4096 co-added scans. The sample was placed in a glass vial and exposed to the laser radiation. The data is presented as intensity as a function of Raman shift (cm$^{-1}$) and is corrected for instrument response and frequency dependent scattering using a white light spectrum from a reference lamp. The Bruker Raman Correct function was used to do the correction. (Bruker software—OPUS 6.0). Experimental error, unless otherwise noted, was ±2 cm$^{-1}$. Peaks were picked using ThermoNicolet Omnic 6.0a software. Intensity assignments are relative to the major band in the spectrum, so are not based on absolute values measured from the baseline.

Example 17

(2R-trans)-5-(4-fluorophenyl)-2-(1-methylethyl)-N, 4-diphenyl-1-[2-(tetrahydro-4-hydroxy-6-oxo-2H-pyran-2-yl)ethyl]-1H-pyrrole-3-carboxamide 50 grams tert-butyl isopropylidene (TBIN), prepared as described in Tetrahedron Letters, 2279 (1992), 13.25 grams wet sponge nickel catalyst, 28% ammonia solution (137.5 ml) and 375 ml isopropyl alcohol (IPA) are added to a pressure vessel. The mixture is reduced with 50 psi of hydrogen, then filtered and concentrated in vacuo. The resulting oil is dissolved in 250 ml warm toluene, water washed and again concentrated in vacuo to give an amino ester. The amino ester, 85 grams 4-fluoro-alpha-[2-methyl-1-oxopropyl]-gamma-oxo-N, beta-diphenylbenzene butanamide (U.S. Pat. No. 5,155,251 and Bauman K. L., Butler D. E., Deering C. F. et al Tetrahedron Letters 1992; 33:2283-2284 both references incorporated by reference in their entirety), 12.5 grams pivalic acid, 137.5 ml tetrahydrofuran and 137.5 ml hexanes are charged to an argon inerted pressure vessel which is sealed and heated to 75° C. for 96 hours. After cooling, the solution is diluted with 400 ml methyl tert-butyl ether (MTBE) and washed firstly with dilute aqueous sodium hydroxide followed by dilute aqueous hydrochloric acid. The mixture is then concentrated in vacuo to give an acetonide ester.

The acetonide ester is dissolved in 275 ml warm methanol and aqueous hydrochloric acid (5 grams of 37% hydrochloric acid in 75 ml of water) is added. The mixture is stirred at 30° C. to produce a diol ester. 100 ml methyl tert-butyl ether and aqueous sodium hydroxide (150 ml of water and 25 grams of 50% aqueous sodium hydroxide) are then added and the mixture stirred at 30° C. to produce the sodium salt. 600 ml water is added and the mixture washed twice with 437.5 ml methyl tert-butyl ether.

In this case, the mixture is distilled under atmospheric pressure to a batch temperature of 99° C. Distillation is continued until the methanol content of the mixture is reduced to 0.4 w/v. The batch is stirred at 75-85% for 18 hours, then cooled, acidified and extracted into 875 ml toluene. The mixture is heated at reflux for 4 hours and water is removed azeotropically. After cooling, the mixture is filtered, washed with toluene and dried directly. The titled compound is isolated as a white solid (Yield: 37.9 grams).

Example 18

PXRD of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha$_s$ X-rays (wavelength=1.5406 Angstroms) with the X-ray tube operated at 40 kV/30 mA. The analyses were performed with the goniometer running in continuous mode set for a 0.2 second count per 0.018° step over a two theta range of 2° to 55°. Peaks were selected using Bruker-AXS Ltd. Evaluation software with a threshold of 1 and a peak width of 0.3° 2-theta. The data were collected at 21° C.

As will be appreciated by the skilled person, the relative intensities of the various peaks within Table 1 given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in given Table.

Such further PXRD patterns generated by use of alternative wavelengths are considered to be alternative representations of the PXRD patterns of the crystalline materials of the present invention and as such are within the scope of the present invention.

Example 19

DSC of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide 2.893 mg of the sample was heated from 10 to 300° C. at 20° C. per minute using a Perkin Elmer Diamond Differential Scanning calorimetry (DSC) with autosampler and a 4 hole side wall vented aluminium pan and lid with nitrogen flow gas.

Example 20

FT-IR of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide The IR spectrum was acquired using a ThermoNicolet Nexus FTIR spectrometer equipped with a 'DurasampIIR' single reflection ATR accessory (diamond surface on zinc selenide substrate) and d-TGS KBr detector. The spectrum was collected at 2 cm$^{-1}$ resolution and a co-addition of 256 scans. Happ-Genzel apodization was used. Because the FT-IR spectrum was recorded using single reflection ATR, no sample preparation was required. Using ATR FT-IR will cause the relative intensities of infrared bands to differ from those seen in a transmission FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$. Peaks were picked using ThermoNicolet Omnic 6.0a software. Intensity assignments are relative to the major band in the spectrum, so are not based on absolute values measured from the baseline.

Example 21

FT-Raman of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide The Raman spectrum was collected using a Bruker Vertex70 with RamII module FT-Raman spectrometer equipped with a 1064 nm NdYAG laser and LN-Germanium detector. The spectrum was recorded using 2 cm$^{-1}$ resolution and Blackman-Harris 4-term apodization. The spectrum was collected using laser power of 300 mW and 4096 co-added scans. The sample was placed in a glass vial and exposed to the laser radiation. The data is presented as intensity as a function of Raman shift and is corrected for instrument response and frequency dependent scattering using a white light spectrum from a reference lamp. The Bruker Raman Correct function was used to do the correction. (Bruker software—OPUS 6.0). Experimental error, unless otherwise noted, was ±2 cm$^{-1}$. Peaks were picked using ThermoNicolet Omnic 6.0a software. Intensity assignments are relative to the major band in the spectrum, so are not based on absolute values measured from the baseline.

Example 22

Phthalimide Acetal

Example 23

3-phthalimido-propionaldehyde

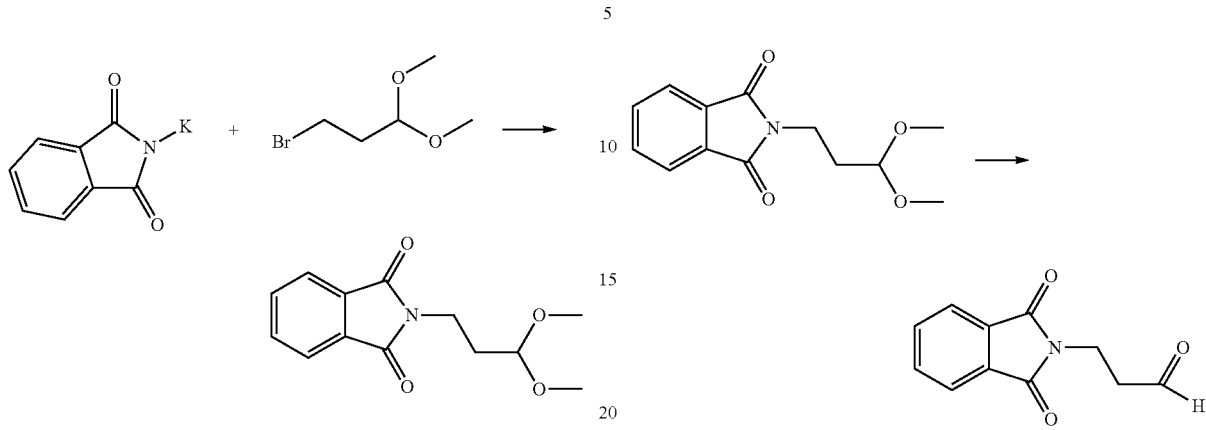

Slurry 50.0 gm of Potassium Phthalimide (1 eq.) in 400 mls (8 vol.) of N,N dimethylormamide at room temperature, a slurry. 3-Bromopropionaldehyde dimethyl acetal 54.4 grams (1.1 eq.) was added dropwise at room temperature, a slurry. The reaction was held for approximately 15 hours and called complete. 2-Methyltetrahydrofuran 250 mls, and water 250 mls, were added and stirred, allowed to settle and separated. The aqueous layer was rewashed twice with 100 mls 2-MTHF, the organic layers combined and washed with 70% saturated brine to remove water. The organic layer was then dried over sodium sulfate, distilled at atmospheric pressure to a slurry. The white slurry granulated at reduced temp 0-5° C. for 1 hr., filtered on a paper covered Buckner funnel and washed with 2-MTHF. The white solids were vac oven dried at less than 40° C., resulting in a yield of 46.5% of the titled product.

15.0 grams of Phthalimide Acetal (1 eq.) were added to 700 mls (approximately 47 vol.) glacial acetic acid and 70 mls (approximately 5 vol.) water. This reaction was held for 48 hours at room temperature up to 30° C., and called complete. Saturated sodium bicarbonate was added to a pH of 7, and extracted with 500 mls 2-MTHF, reextracted with 500 mls 2-MTHF. The organic layer was then dried over sodium sulfate, vacuum distilled to a slurry. The white slurry granulated at reduced temperature 0-5° C. for 1 hour, filtered on a paper covered Buckner funnel and washed with 2-MTHF. The white solids were vac oven dried at room temperature, resulting in a yield of 47% of the titled product.

Example 24

SEQ ID NO: 1

- Nucleotide sequence of DERA03

```
atgactgatctgaaagcaagcagcctgcgtgcactgaaattgatggacctgaccaccctgaatgacgacgacaccgacgagaa agtgatcgccctgtgtcatcaggccaaaactccggtcggcaataccgccgctatctgtatctatcctcgctttatcccgattgctcgca aaactctgaaagagcagggcaccccggaaatccgtatcgctacggtaaccaacttcccacacggtaacgacgacatcgacatc gcgctggcagaaacccgtgcggcaatcgcctacggtgctgatgaagttgacgttgtgttcccgtaccgcgcgctgatggcgggtaa cgagcaggttggttttgacctggtgaaagcctgtaaagaggcttgcgcggcagcgaatgtactgctgaaagtgatcatcgaaacc ggcgaactgaaagacgaagcgctgatccgtaaagcgtctgaaatctccatcaaagcgggtgcggacttcatcaaaacctctacc ggtaaagtggctgtgaacgcgacgccggaaagcgcgcgcatcatgatggaagtgatccgtgatatgggcgtagaaaaaaccgt tggtttcaaaccgcgggcggcgtgcgtactgcggaagatgcgcagaaatatctcgccattgcagatgaactgttcggtgctgact gggcagatgcgcgtcactaccgctttggcgcttccagcctgctggcaagcctgctgaaagcgctgggtcacggcgacggtaaga gcgccagcagctactaa
```

Example 25

SEQ ID NO: 2

- Nucleotide Sequence of DERA04

```
atgggtaatatcgcgaaaatgattgatcacaccctcttaaaacccgaagcaaccgaacaacaaattgtacaattatgcacggaag cgaaacaatatggctttgcagcagtatgcgtaaatccgacatgggttaaaaccgccgcacgtgaattaagcgggacagacgttcg tgtgtgtactgtaattggatttcccttgggcgctacgactccagaaactaaagcattcgaaactactaacgcgattgaaaatggagca
```

-continued cgggaagtagatatggtaattaatattggtgcattgaaatctggacaagatgaactggtggaacgtgatattcgtgccgttgttgaag ctgcagcaggccgcgcgcttgtgaaagtaattgtagaaacagcccttcttactgatgaagaaaaagttcgcgcttgtcaattagcag taaaagcgggtgccgattatgtgaagacgtcgacaggatttagcggtggtggtgcaacggtggaagatgtggctttaatgcggaa aacggttggtgatcgtgcaggggtcaaagcaagcggcggagtacgtgactggaaaacagcagaagcaatgattaacgcagga gcaacgcgcattggcacaagttctggagtagcaatcgtaacaggtggaaccggccgggcagactattaa Example 26

SEQ ID NO: 3

- Nucleotide Sequence of DERA06
atgggactcgcctcctacatcgaccacacgctgcttaaggccaccgccacgctcgccgacatccgcacgctgtgtgaggaagcc cgcgagcactcgttctacgcggtgtgcatcaacccggtctttattccccacgcccgcgcctggctcgaaggcagcgacgtgaaggt cgccaccgtctgcggctttcccctcggcgccatcagctccgagcagaaagctctggaagcccgcctgagcgccgaaacgggcg ccgacgaaatcgatatggtcatccacatcggctcggcgcttgccggcgactgggacgcggtggaagccgacgtgcgggcagtg cgccgcgcggtgcccgagcaggtgctcaaggtgattatcgaaacctgctacctgaccgacgagcaaaagcgcttggcgactga ggtcgccgtacagggcggcgccgacttcgtgaagacgagcacaggcttcggcaccggcggcgccaccgtggacgacgtgcgc ctgatggcggaagtgatcggggccgcgccggactcaaggcggcgggcggcgtccgcactcctgccgacgcgcaagccatg atcgaggcgggcgcgacccggctgggcacctcgggcggcgtgggtctggtgtcgggcggcgaaaacggagccggctactga Example 27      30

SEQ ID NO: 4

- Nucleotide Sequence of DERA08
atgggaattgctaaaatgatcgatcacactgctttaaaaccagacacaacgaaagaacaaattttaacactaacaaaagaagca agagaatacggttttgcttccgtatgcgtaaatccaacttgggtaaaactatccgctgaacaacttgctggagcagaatctgtagtat gtactgttatcggtttcccactaggagcgaatacccctgaagtaaaagcatttgaagtaaaagatgctatccaaaacggtgcaaaa gaagtggatatggttattaatatcggcgcactaaaagacaaagacgacgaactagtagaacgtgatattcgcgctgtagtcgatgc tgccaaaggaaaagcattagtaaaagtaattatcgaaacttgcctattaacagacgaagaaaaagttcgcgcatgtgaaatcgct gtaaaagcgggaacagacttcgttaaaacatccactggattctccacaggtggcgcaactgccgaagatatcgccttaatgcgta aaactgtaggaccaaacatcggcgtaaaagcatctggtggggttcgtacgaaagaagacgtagaaaaaatgatcgaagcagg cgcaactcgtattggcgcaagtgcaggtgtcgcaattgtttccggcgaaaaaccagccaaaccagataattactaa Example 28

SEQ ID NO: 5

- Nucleotide Sequence of DERA11
atgacatcaaatcaacttgctcaatatatcgatcacaccgcacttaccgcagaaaaaaatgaacaagatatttcgacactctgtaat gaagcgattgaacacggatttttattctgtatgtatcaattctgcttatattccactcgctaaagaaaaacttgctggctcaaatgtaaaa atttgcaccgtagtttggattcccctttgggggcgaatttaacctcagtcaaagcatttgaaacgcaagaatctattaaagcgggtgcaa atgaaattgatatggtgattaatgtaggttggataaaatcgcaaaaatgggatgaagtaaaacaagatattcaagcggtatttaatg cttgtaatggcacgccattaaaagtgattttagaaacttgtttgctcactaaagatgaaatagtgaaagcctgcgaaatttgtaaaga aatcggtgtagcttttgttaaaacatcaacaggctttaataaaggtggtgcgaccgtagaagatgttgcattgatgaaaaacacggtc ggcaatattggtgttaaagcatcaggtggtgtgcgtgatactgaaactgcacttgcaatgattaaggcgggtgcgactcgcattggtg caagcgctggcattgcgattattagcggtactcaagacactcaaagcacttactaa

Example 29

SEQ ID NO: 6
- Nucleotide Sequence of DERA12
atgatagagtacaggattgaggaggcagtagcgaagtacagagagttctacgaattcaagcccgtcagagaaagcgcaggtatt gaagatgtgaaaagtgctatagagcacacgaatctgaaaccgtttgccacaccagacgatataaaaaaaactctgtcttgaagca agggaaaatcgtttccatggagtctgtgtgaatccgtgttatgtgaaactggctcgtgaagaactcgaaggaaccgatgtgaaagtc gtcaccgttgttggttttccactgggagcgaacgaaactcggacgaaagcccatgaggcgattttcgctgttgagagtggagccgat gagatcgatatggtcatcaacgttggcatgctcaaggcaaaggagtgggagtacgtttacgaggatataagaagtgttgtcgaatc ggtgaaaggaaaagttgtgaaggtgatcatcgaaacgtgctatctggatacggaagagaagatagcggcgtgtgtcatttccaaa cttgctggagctcatttcgtgaagacttccacgggatttggaacaggaggggcgaccgcagaagacgttcatctcatgaaatggat cgtgggagatgagtgggtgtaaaagcttccggagggatcagaaccttcgaggacgctgttaaaatgatcatgtacggtgctgata gaataggaacgagttcgggagttaagatcgttcagggggagaagagagatatggaggttga

Example 30

SEQ ID NO: 7
- Nucleotide Sequence of DERA15
atgccgtcggccagggatatactgcagcagggtctagacaggctagggagccctgaggacctcgcctcgaggatagactctacg ctactaagccctagggctacggaggaggacgttaggaatcttgtgagagaggcgtcggactacgggtttagatgcgcggttctga ctccagtgtacacagtaaagatttctgggctggctgagaagcttggtgtgaagctatgtagcgttataggctttcccctgggccaggc cccgctcgaggtaaagctagttgaggcacaaactgttttagaggctggggctactgagcttgatgttgtccccatctctcactaggc cccgaagctgtttacagggaggtctcagggatagtgaagttggcgaaaagctatggagccgttgtgaaagtaatattagaagcgc cactctgggatgacaaaacgctctccctcctggtggactcgtcgaggagggcggggcggatatagtgaagacaagcaccggg gtctatacaaagggtggtgatccagtaacggtcttcaggctggccagtcttgccaagcccctggtatgggtgtaaaggcaagcgg cggtataaggagtggcatcgacgccgtcctcgccgtaggagctggcgcggatatcatagggacaagcagtgctgtaaaggttttg gagagcttcaaatccctagtctaa

Example 31

SEQ ID NO: 8
- Nucleotide Sequence of DERA 101
atggctgcaaacaaatatgaaatggccttcgcacagttcgatccagctgaaagcgaagaacgcatcctg ctgaaaactgaccagatcattcgtgaccactattcccgtttcgacactccagaaactaaaaagttcctg catggcgttatcgatctgacgtctctgaacgccaccgactctgaggaatctatcactaaattcaccgaa tctgtaaacgatttcgaagataccgacccgactatccctagcgttgcggcgatctgcgtttatccgaac tttgtcagcaccgtgcgtgaaaccctgactgccgagaatgtgaaagttgcaagcgtcagcggttgcttc ccggcctcccagagcttcatcgaagtgaaactggcagaaaccgcactggcggttagcgacggtgcggat gaaattgacattgttctgaacatgggtaaattcctgtccggtgattacgaggccgcagccactgagatc gaggaacagatcgctgcggcgaagggtgcgaccgtaaaagttatcctggagactggtgctctgaagacg ccggaaaacattcgccgcgcaaccatcctgtctctgttttgtggcgcccatttcgttaaaacctctact ggcaaaggctacccgggcgcctctctggaagcagcttacactatgtgtaaagtcctgaaacagtactac ggcctgttcggtgaagttcgtggcatcaagctgagcggcggtatccgtaccaccgaagacgcggttaag tactactgcctgatcgaaacgctgctgggcaaagaatggctgaccccggcgtacttccgcatcggcgcc tcctctctggtttgatgctctgcgccaggatattatggtttaa

Example 32

SEQ ID NO: 9
- Nucleotide Sequence of DERA 102
Atggaactgaaccgcatgattgaccacactattctgaaaccggaagccaccgaggcggctgtgcagaaa
attatcgatgaagctaaagaatacaacttcttcagcgtctgtatcaacccgtgttgggttgcttttgcc
tccgagcagctggctgatactgatgttgccgtctgtaccgtaatcggtttcccgctgggcgcgaacacg
ccggaggttaaagcgtacgaagcagctgacgccattaaaaacggtgctaatgaggtggatatggtgatc
aatattggtgctctgaaatcccaacagtacgactacgtgcgccaagacatccagggtgtggttgacgcc
gcaaaaggtaaagcactggttaaagttatcatcgaaactgccctgctgaccgatgaagagaaagttaag
gcttgcgaactggcgaaagaagcaggcgctgatttcgtgaaaaccagcaccggttttttccactggcggt
gcaaaagttgctgacattcgtctgatgcgcgaaaccgtgggtccggatatgggcgttaaagcatccggt
ggcgtacacaacgcagaagaagcactggccatgatcgaagcgggcgcaactcgtatcggcgcttccacc
ggtgtagccatcgtaagcggtgctactggtgagggtaccaaatggtaa

Example 33

SEQ ID NO: 10
- Nucleotide Sequence of DERA 103
atgactattgaatccgctatcgcgctggcacctgcagaacgtgctgttaacctgattggtagcgacctg
accgaaaaatctctgaaactgcacctggaaggcctgtctggtgtcgacgcggttggtctggaacagcgt
gctgccggtctgtccacccgctctatcaaaaccacctccaaagcttgggccctggacaccatcatcaaa
ctgatcgatctgactactctggagggcgcagatactccgggcaaggttcgttctctggctgcgaaagca
atgctgccggacgcctctgatgtgtccgctccgcaggtggcagctgtgtgcgtttacggtgatatggtg
ccatacgcggcggaagcactgggctcctcttggtctaatggttctgacaacggcattaacgttgctgcg
gtggcaactgcgttcccatccggtcgcagctccctgccaatcaaaatcgctgacaccaaggaagccgtt
gcccacggtgctgacgaaatcgacatggtaatcgatcgtggtgcgttcctgagcggcaaatacggtgtt
gtgttcgaccagatcgtagctgtgaaagaagcttgccgccgcgaaaacggcacttacgcgcacctgaaa
gttatcctggaaaccggcgaactgaacacctatgacaacgtccgccgtgcctcctggctggcgatcctg
gcgggtggtgactttgtgaaaacctctaccggcaaggttagcccggccgcaaccctgccggttacgctg
ctgatgctggaagtcgttcgcgattggcatgtgctgactggcgagaaaatcggtgtgaaaccagccggt
ggtatccgctcctccaaagacgcgattaaatacctggtcaccgtggcggaaaccgtaggtgaagagtgg
ctgcaaccgcacctgtttcgctttggcgcctcctccctgctgaacgacgttctgatgcagcgtcagaag
ctgtctaccggccactactccggcccagattacgtgaccatcgactaa

Example 34

SEQ ID NO: 11
- Nucleotide Sequence of DERA 104
atgtcttctactccaactattctggatccggcgtttgaggacgttacccgttctgaagcatctctgcgc
cgtttcctgcacggcctgccgggtgtcgatcaggtgggcgcagaggcccgtgccgctggtctggcaacc
cgttccattaaaaacgtccgcaaaagaatttgcactggacctggcgattcgtatggttgacctgaccacg
ctggagggccaggatacgccgggtaaggttcgtgccctgagcgcgaaagcaatgcgtccggatccgtct
gatccaacctgtcctgctactgctgctgtatgtgtttacccggacatggttggcatcgcgaaacaggcg
ctgggtactagcggcgtacacgtagctgctgtggctactgctttcccgtctggccgtgccgctctggac -continued atcaaactggcggacgttcgtgatgcggtggacgcaggcgctgacgaaatcgatatggttatcgaccgc ggtgcttttctggctggtcgttaccaacacgtatacgacgaaattgttgcggtgcgcgaagcctgccgc cgtgaaaacggtgaaggcgctcacctgaaggtaatcttcgagactggtgagctgcagacctacgacaac gttcgccgtgcgagctggctggcgatgatggctggtgcacacttcgttaaaacgtccaccggcaaagtc cagccggcagctaccctgccggttaccctggttatgctgcaggccgtacgtgactttcgtggcgcaacg ggccgtatggttggcgttaaacctgctggcggtatccgtaccgccaaggacgcaatcaaatacctggtt atggtaaacgaggtagcgggcgaagattggctggacccggactggtttcgttttggtgcatctactctg ctgaacgacctgctgatgcagcgtacgaagatgaaaaccggccgttacagcggcccagactactttacc ctggactaa Example 35

SEQ ID NO: 12

- Nucleotide Sequence of DERA 105
atggaactgatcactcagccgtcttgttgggtattttccgtcttttccgccgtcagtacggctggctg gttttgtggaaggtgcttggtacgatggtcgccgtcaaactttccacctggatggtaacggccgcaaa ggcttcctgcgcatgactatgaatatcgcaaaaatgatcgatcacaccctgctgaaaccggaagcgact gagcagcagatcgtacaactgtgcaccgaagctaaacagtatggttttgcttccgtttgtgtgaaccct acgtgggtgaaaaccgccgcacgcgaactgtctggtaccgacgttcgtgtttgtaccgtaattggcttc ccgctgggcgcgactaccccagaaaccaaagcgttcgaaactaccaacgcgatcgaaaacgcgctcgt gaagtcgacatggtaatcaacattggcgctctgaaatctggtcaggacgaactggtagagcgtgacatc cgcgccgtcgtagaagctgcggcaggccgtgcactggtaaaagtaatcgttgaaaccgctctgctgact gatgaagagaaagttcgtgcgtgtcagctggcggttaaagctggtgcagattacgtgaaaacgagcact ggtttctccggtggtggcgctactgtcgaagacgtggcgctgatgcgtaaaaccgtaggcgatcgcgca ggcgttaaagcgagcggcggtgttcgtgattggaagactgccgaagctatgattaacgcaggcgcgact cgtatcggcacttctagcggcgtggcaattgttactggcggcaccggtcgcgctgacactaaatggtaa Example 36

SEQ ID NO: 13

- Nucleotide Sequence of DERA 106
atgactatcgctaaaatgattgatcacacggcgctgaagccagataccaccaaagaacaaatcctgacg ctgaccaaagaagcacgtgaatatggctttgctagcgtctgtgtgaatccgacttgggtgaaactgtct gcggaacagctgagcggcgctgaatctgtggtgtgcaccgtcatcggttttccgctgggcgcgaatact ccggaagtgaaggcattcgaagtaaaaaacgctatcgaaaacggcgcgaaggaagtagatatggttatc aacattggtgctctgaaggataaggacgacgaactggtgaacgtgatatccgtgccgtcgtggatgct gctaaaggtaaagcgctggtgaaagtcattatcgaaacctgcctgctgaccgatgaagagaaggtccgt gcttgcgaaatcgccgtgaaagctggcactgatttcgttaaaacttctactggcttttctactggtggc gcgactgcagaagacatcgcactgatgcgtaagactgtcggtccgaacatcggtgtaaaagcgtccggt ggtgttcgtactaaagaagacgttgagaagatgatcgaagcgggtgccacccgtatcggcgcttctgca ggtgtggcaatcgtatccggtgaaaaaccggcgaaacctgacaacaccaagtggtaa

Example 37

SEQ ID NO: 14
- Nucleotide Sequence of DERA 107 atgtctcgctctattgcacaaatgatcgatcacaccctgctgaaacctaataccaccgaagaccagatc gtgaaactgtgcgaagaggctaaagaatactctttcgcctccgtatgcgtcaacccaacgtgggtcgcg ctggcagcgcagctgctgaaagacgctcctgatgtgaaagtgtgcactgttatcggcttcccactgggt gcaaccacgcctgaagtaaaagcgtttgaaaccactaacgcaatcgagaacggcgcaacggaggttgat atggttatcaacatcggtgccctgaaggacaaacagtacgaactggttggtcgtgatatccaggctgtt gtgaaggcagcagaaggcaaagccctgaccaaagtgattatcgaaacctccctgctgaccgaagaagaa aagaaggcggcttgtgaactggcggtaaaagcaggtgctgatttcgtcaaaacgtctaccggtttctct ggtggcggtgcaaccgcagaagacattgccctgatgcgtaaggttgttggtcctaacctgggcgttaag gccagcggcggtgtgcgtgacctgtctgacgcgaaggcgatgattgacgcgggcgcgactcgtatcggc gcttccgcaggtgttgcgatcgttaatggtgaacgctctgaaggttccacgaaatggaccgcagctggt gcggcgacgacgtgcgcttgtacgggcggctaa

Example 38

SEQ ID NO: 15
- Nucleotide Sequence of DERA 108 atgaaactgaacaaatacatcgatcacaccatcctgaaaccggaaacgactcaggaacaggtggagaaa atcctggctgaagcgaaagaatacgatttcgcgtccgtctgcgttaacccgacgtgggtagctctggca gctgaaagcctgaaagatagcgacgtcaaagtctgcactgtcatcggcttcccgctgggcgctaacact ccggcagtgaaggcgttcgaaactaaagacgctattagcaacggcgcggatgaaatcgacatggtgatt aacatcggcgcactgaaaacgggtaactacgatctggttctggaagatattaaggctgtcgttgcagca agcggcgataaactggtaaaggtaatcatcgaagcgtgcctgctgaccgacgatgaaaaggttaaagcg tgccagctgtctcaggaagcgggcgctgactacgtcaagacgagcactggcttctctaccggcggtgcg acggtcgcagatgttgctctgatgcgtaaaactgttggcccggacatgggcgtaaaagcgtctggcggt gcgcgctcttacgaagacgctatcgcgttcattgaagctggcgcaagccgtattggcgccagctctggc gtggcgatcatgaatggtgcgcaggctgatggcgacaccaagtggtaa

Example 39

SEQ ID NO: 16
- Amino Acid Sequence of DERA03

Mtdlkasslralklmdlttlndddtdekvialchqaktpvgntaaiciyprfipiarktlkeqgtpeir iatvtnfphgnddidialaetraaiaygadevdvvfpyralmagneqvgfdlvkackeacaaanvllkv iietgelkdealirkaseisikagadfiktstgkvavnatpesarimmevirdmgvektvgfkpaggvr taedaqkylaiadelfgadwadarhyrfgassllasllkalghgdgksassy.

Example 40

SEQ ID NO: 17
- Amino Acid Sequence of DERA04
Mgniakmidhtllkpeateqqivqlcteakqygfaavcvnptwvktaarelsgtdvrvctvigfplgattpetkafettnaiengarev dmvinigalksgqdelverdiravveaaagralvkvivetalltdeekvracqlavkagadyvktstgfsgggatvedvalmrktvgd ragvkasggvrdwktaeaminagatrigtssgvaivtggtgrady.

Example 41

SEQ ID NO: 18
- Amino Acid Sequence of DERA06
Mglasyidhtllkatatladirticeearehsfyavcinpvfipharawlegsdvkvatvcgfplgaisseqkalearlsaetgadeidm vihigsalagdwdaveadvravrravpeqvlkviietcyltdeqkrlatevavqggadfvktstgfgtggatvddvrlmaeviggragl kaaggvrtpadaqamieagatrlgtsggvglvsggengagy.

Example 42

SEQ ID NO: 19
- Amino Acid Sequence of DERA08
Mgiakmidhtalkpdttkeqiltitkeareygfasvcvnptwvklsaeqlagaesvvctvigfplgantpevkafevkdaiqngakev dmvinigalkdkddelverdiravvdaakgkalvkviietclltdeekvraceiavkagtdfvktstgfstggataedialmrktvgpnig vkasggvrtkedvekmieagatrigasagvaivsgekpakpdny.

Example 43

SEQ ID NO: 20
- Amino Acid Sequence of DERA11
Mtsnqlaqyidhtaltaekneqdistlcneaiehgfysvcinsayiplakeklagsnvkictvvgfplganitsvkafetqesikagane idmvinvgwiksqkwdevkqdiqavfnacngtplkviletclltkdeivkaceickeigvafvktstgfnkggatvedvalmkntvgni gvkasggvrdtetalamikagatrigasagiaiisgtqdtqsty.

Example 44

SEQ ID NO: 21
- Amino Acid Sequence of DERA12
Mieyrieeavakyrefyefkpvresagiedvksaiehtnlkpfatpddikklclearenrfhgvcvnpcyvklareelegtdvkvvtvv gfplganetrtkaheaifavesgadeidmvinvgmlkakeweyvyedirsvvesvkgkvvkviietcyldteekiaacvisklagah fvktstgfgtggataedvhlmkwivgdemgvkasggirtfedavkmimygadrigtssgvkivqggeerygg.

Example 45

SEQ ID NO: 22
- Amino Acid Sequence of DERA15
Mpsardilqqgldrlgspedlasridstllsprateedvrnlvreasdygfrcavltpvytvkisglaeklgvklcsvigfplgqaplevklv eaqtvleagateldvvphlslgpeavyrevsgivklaksygavvkvileaplwddktlsllvdssrragadivktstgvytkggdpvtvf rlaslakplgmgvkasggirsgidavlavgagadiigtssavkvlesfkslv.

Example 46

SEQ ID NO: 23
- Amino Acid Sequence of DERA101
maankyemafaqfdpaeseerillktdqiirdhysrfdtpetkkflhgvidltslnatdseesitkfte svndfedtdptipsvaaicvypnfvstvretltaenvkvasvsgcfpasqsfievklaetalaysdgad eidivlnmgkflsgdyeaaateieeqiaaakgatvkviletgalktpenirratilslfcgahfvktst gkgypgasleaaytmckvlkqyyglfgevrgiklsggirttedavkyyclietllgkewltpayfriga sslvdalrqdimv.

Example 47

SEQ ID NO: 24
- Amino Acid Sequence of DERA102
melnrmidhtilkpeateaavqkiideakeynffsvcinpcwvafaseqladtdvavctvigfplgant pevkayeaadaiknganevdmvinigalksggydyvrgdiqgvvdaakgkalvkviietalltdeekvk acelakeagadfvktstgfstggakvadirlmretvgpdmgvkasggvhnaeealamieagatrigast gvaivsgatgegtkw.

Example 48

SEQ ID NO: 25
- Amino Acid Sequence of DERA103
mtiesaialapaeravnligsdltekslklhleglsgvdavglewraaglstrsikttskawaldtiik lidlttlegadtpgkvrslaakamlpdasdvsapqvaavcvygdmvpyaaealgsswsngsdnginvaa vatafpsgrsslpikiadtkeavahgadeidmvidrgaflsgkygvvfdqivavkeacrrengtyahlk viletgelntydnvrraswlailaggdfvktstgkvspaatlpvtllmlevvrdwhvltgekigvkpag girsskdaikylvtvaetvgeewlqphlfrfgasslindvlmqrqklstghysgpdyvtid.

Example 49

SEQ ID NO: 26
- Amino Acid Sequence of DERA104
msstptildpafedvtrseaslrrflhglpgvdqvgaearaaglatrsiktsakefaldlairmvdltt legqdtpgkvralsakamrpdpsdptcpataavcvypdmvgiakqalgtsgvhvaavatafpsgraald ikladvrdavdagadeidmvidrgaflagryqhvydeivavreacrrengegahlkvifetgelqtydn vrraswlammagahfvktstgkvqpaatlpvtlvmlqavrdfrgatgrmvgvkpaggirtakdaikylv mvnevagedwldpdwfrfgastllndllmqrtkmktgrysgpdyftld.

Example 50

SEQ ID NO: 27
- Amino Acid Sequence of DERA105
melitqpscwvfsvffrrqygwlvfvegawydgrrqtfhldgngrkgflrmtmniakmidhtllkpeat eqqivqlcteakqygfasvcvnptwvktaarelsgtdvrvctvigfplgattpetkafettnaiengar evdmvinigalksgqdelverdiravveaaagralvkvivetalltdeekvracqlavkagadyvktst gfsggatvedvalmrktvgdragvkasggvrdwktaeaminagatrigtssgvaivtggtgradtkw.

Example 51

SEQ ID NO: 28
- Amino Acid Sequence of DERA106
mtiakmidhtalkpdttkeqiltltkeareygfasvcvnptwvklsaeqlsgaesvvctvigfplgant pevkafevknaiengakevdmvinigalkdkddelverdiravvdaakgkalvkviietclltdeekvr aceiavkagtdfvktstgfstggataedialmrktvgpnigvkasggvrtkedvekmieagatrigasa gvaivsgekpakpdntkw.

Example 52

SEQ ID NO: 29
- Amino Acid Sequence of DERA107
msrsiaqmidhtllkpnttedwivklceeakeysfasvcvnptwvalaaqllkdapdvkvvtvigfplg attpevkafettnaiengatevdmvinigalkdkwyelvgrdiwavvkaaegkaltkviietsllteee kkaacelavkagadfvktstgfsgggataedialmrkvvgpnlgvkasggvrdlsdakamidagatrig asagvaivngersegstkwtaagaattcactgg.

Example 53

SEQ ID NO: 30
- Amino Acid Sequence of DERA108
mklnkyidhtilkpettqeqvekilaeakeydfasvcvnptwvalaaeslkdsdvkvctvigfplgant pavkafetkdaisngadeidmvinigalktgnydlvledikavvaasgdklvkviieaclltddekvka cqlsqeagadyvktstgfstggatvadvalmrktvgpdmgvkasggarsyedaiafieagasrigassg vaimngaqadgdtkw.

All publications, including but not limited to, issued patents, patent applications, and journal articles, cited in this application are each herein incorporated by reference in their entirety.

Although the invention has been described above with reference to the disclosed embodiments, those skilled in the art will readily appreciate that the specific experiments detailed are only illustrative of the invention. Accordingly, the invention is limited only by the following claims.

---

The claimed invention is:

1. 2-[2-(4,6-Dihydroxy-tetrahydro-pyran-2-yl)ethyl]-isoindole-1,3-dione.

2. A compound according to claim 1, wherein said compound is

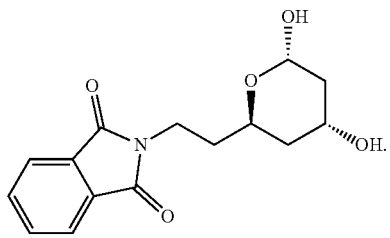 [SMILES: O=C1c2ccccc2C(=O)N1CC[C@@H]1C[C@@H](O)C[C@@H](O)O1]

3. A compound according to claim 1, wherein said compound is

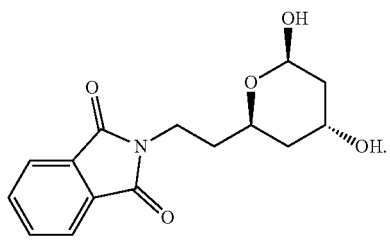 [SMILES: O=C1c2ccccc2C(=O)N1CC[C@@H]1C[C@@H](O)C[C@H](O)O1]

4. A compound of the formula

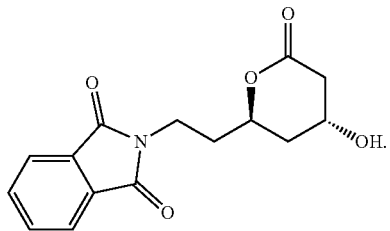 [SMILES: O=C1C[C@H](O)C[C@@H](CCN2C(=O)c3ccccc3C2=O)O1]

5. A compound of the formula

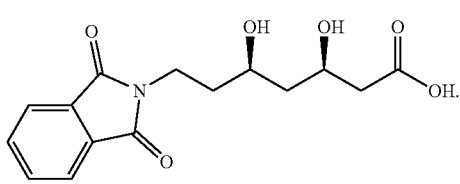 [SMILES: O=C(O)C[C@H](O)C[C@H](O)CCN1C(=O)c2ccccc2C1=O]

6. A compound of the formula

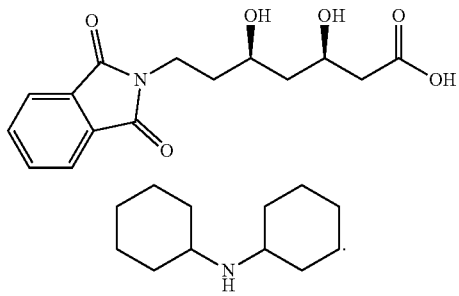

7. A compound of the formula

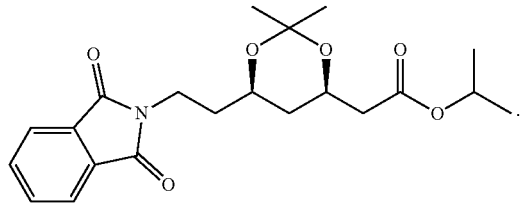 [SMILES: CC(C)OC(=O)C[C@H]1C[C@@H](CCN2C(=O)c3ccccc3C2=O)OC(C)(C)O1]

8. A compound of the formula

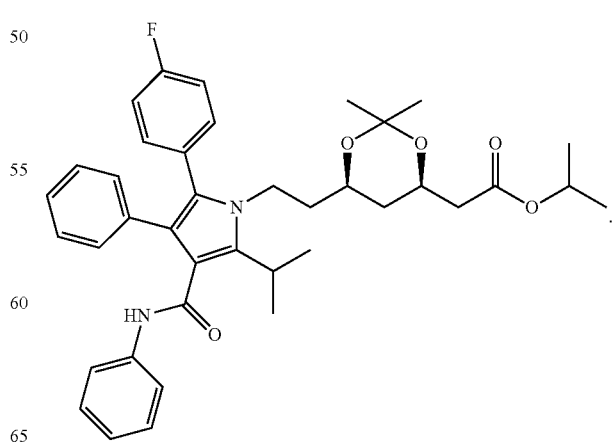

9. A compound of the formula

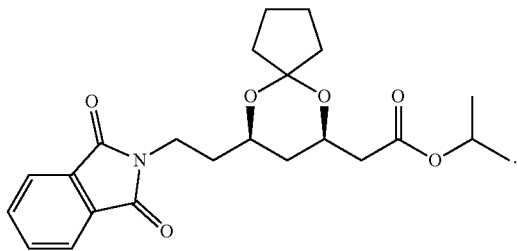 [SMILES: CC(C)OC(=O)C[C@H]1C[C@@H](CCN2C(=O)c3ccccc3C2=O)OC2(CCCC2)O1]

10. A compound of the formula

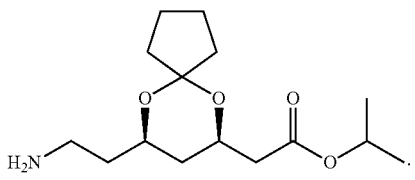 [SMILES: CC(C)OC(=O)C[C@H]1C[C@@H](CCN)OC2(CCCC2)O1]

11. A compound of the formula

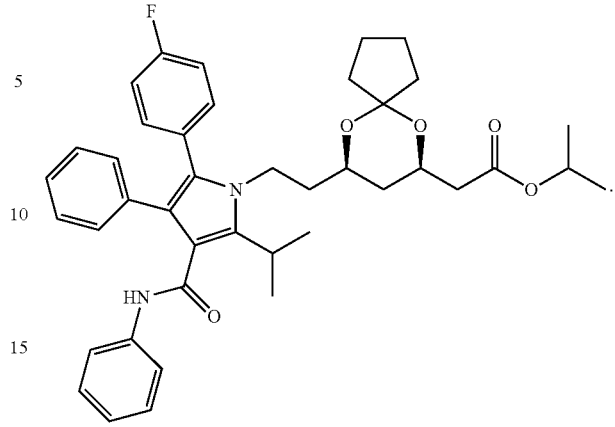

12. A crystalline form of 4-fluoro-alpha-[2-methyl-1-oxo-propyl]-gamma-oxo-N, beta-diphenylbenzenebutanamide characterized as having powder X-ray diffraction peaks of about 9.0, 12.7, 20.2, 22.6, and 25.2 degrees two theta.

13. A crystalline form of (2R-trans)-5-(4-fluorophenyl)-2-(1-methylethyl)-N, 4-diphenyl-1-[2-(tetrahydro-4-hydroxy-6-oxo-2H-pyran-2-yl)ethyl]-1H-pyrrole-3-carboxamide characterized as having powder X-ray diffraction peaks of about 6.3, 12.7, 16.8, 21.1 and 25.5 degrees two theta.

* * * * *